US011364276B2

(12) United States Patent
Gabere et al.

(10) Patent No.: US 11,364,276 B2
(45) Date of Patent: Jun. 21, 2022

(54) ANTIVIRAL PEPTIDES FOR TREATMENT OF THE MIDDLE EAST RESPIRATORY SYNDROME

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventors: Musa Nur Gabere, Riyadh (SA); Sabeena Mustafa, Riyadh (SA); Hanan Balkhy, Riyadh (SA); Mohamed Hussein, Riyadh (SA); Ibraheem Abdulaziz Bushnak, Riyadh (SA)

(73) Assignees: National Guard Health Affairs, Riyadh (SA); King Abdullah International Medical Research Center, Riyadh (SA); King Saud bin Abdulaziz University for Health Sciences, Riyadh (SA)

(*) Notice: Subject to any disclaimer, the term of this patent is extended or adjusted under 35 U.S.C. 154(b) by 0 days.

(21) Appl. No.: 16/831,187

(22) Filed: Mar. 26, 2020

(65) Prior Publication Data
US 2020/0306338 A1 Oct. 1, 2020

Related U.S. Application Data

(60) Provisional application No. 62/823,912, filed on Mar. 26, 2019.

(51) Int. Cl.
A61K 38/08 (2019.01)
A61P 31/14 (2006.01)
A61K 9/00 (2006.01)

(52) U.S. Cl.
CPC ............ A61K 38/08 (2013.01); A61K 9/0029 (2013.01); A61K 9/0078 (2013.01); A61P 31/14 (2018.01)

(58) Field of Classification Search
CPC ................................ A61K 38/08; A61P 31/14
See application file for complete search history.

(56) References Cited

U.S. PATENT DOCUMENTS

| 2010/0316643 | A1* | 12/2010 | Eckert | A61P 31/12 424/134.1 |
| 2014/0221278 | A1* | 8/2014 | Hillman | A61K 38/1729 514/4.8 |
| 2015/0152149 | A1* | 6/2015 | Zheng | C07K 14/4723 514/3.7 |
| 2017/0247672 | A1* | 8/2017 | Chen | C12N 9/00 |
| 2017/0340728 | A1 | 11/2017 | Kyratsous et al. | |

FOREIGN PATENT DOCUMENTS

| WO | WO 2015/057942 A1 | 4/2015 |
| WO | WO 2016/046734 A2 | 3/2016 |
| WO | WO 2016/090345 A1 | 6/2016 |

OTHER PUBLICATIONS

Mustafa et al., epub Aug. 31, 2017, Current treatment options and the role of peptides as potential therapeutic components for Middle Est Respiratory Syndrome (MERS): A review, Journal of Infection and Public Health, 11: 9-17.*
Chaparro et al., 2016, Lacrain: the first antimicrobial peptide from the body extract of the Brazilian centipede *Scolopendra viridicornis*, International Journal of Antimicrobial Agents, 48: 277-285.*
Channappanavar et al., 2015, Protective Effect of Intranasal Regimens Containing Peptidic Middle East Respiratory Syndrome Coronavirus Fusion Inhibitor Against MERS-CoV Infection, The Journal of infectious Diseases, 212: 1894-1903.*
Gao et al., 2013, Structure of the Fusion Core and Inhibition of Fusion by a Heptad Repeat Peptide Derived from the S Protein of Middle East Respiratory Syndrome Coronavirus, Journal of Virology, 87(24): 13134-13140.*
Lu et al., 2014, Structure-based discovery of Middle East respiratory syndrome coronavirus fusion inhibitor, Nature Communications, 5: 3067 (12 pages).*
Alraddadi et al., 2016, Risk Factors for Primary Middle East Respiratory Syndrome Coronavirus Illness in Humans, Saudi Arabi, 2014, Emerging Infectious Diseases, 22(1): 49-55.*
Halim et al., 2016, Clinical characteristics and outcome of ICU admitted MERS corona virus infected patients, Egyptian Journal of Chest Diseases and Turburculosis, 65: 81-87.*
Shuai Xia, et al., "Middle East respiratory syndrome coronavirus (MERS-CoV) entry inhibitors targeting spike protein", Virus Research, vol. 194, 2014, pp. 200-210.
Sabeena Mustafa, et al., "Current treatment options and the role of peptides as potential therapeutic components for Middle East Respiratory Syndrome (MERS): A review", Journal of Infection and Public Health, vol. 11, 2018, pp. 9-17.
Elisa Chaparro-Aguirre, "Bioactive molecules in Quilopods", Masters Thesis, Biology of Pathogen-Host Relation—Instituto De Ciências Biomédicas, 2011, 28 pages (with English Abstract).
Hanjun Zhao, et al., "A novel peptide with potent and broad-spectrum antiviral activities against multiple respiratory viruses", Scientific Reports, vol. 6, Issue 22008, 2016, pp. 1-13.
Nianshuang Wang, et al., "Structure of MERS-CoV spike receptor-binding domain complexed with human receptor DPP4", Cell Research, vol. 23, No. 8, Aug. 2013, pp. 986-993.
Elisa Chaparro, et al., "Lacrain: The first antimicrobial peptide from the body extract of the Brazilian centipede *Scolopendra viridicornis*", International Journal of Antimicrobial Agents, Jul. 2016, pp. 1-9.
Thanigaimalai Pillaiyar, et al., "Middle East Respiratory Syndrome-Coronavirus (MERS-CoV): An Updated Overview and Pharmacotherapeutics", Medicinal Chemistry, vol. 5, No. 8, 2015, pp. 361-372.

(Continued)

*Primary Examiner* — Amber D Steele
(74) *Attorney, Agent, or Firm* — Oblon, McClelland, Maier & Neustadt, L.L.P.

(57) ABSTRACT

A peptide that binds to the Si spike protein of Middle East Respiratory syndrome coronavirus or MERS-CoV and a method for inhibiting infection of a subject exposed to or having MERS-CoV by administering the peptide.

19 Claims, 27 Drawing Sheets
Specification includes a Sequence Listing.

(56) References Cited

OTHER PUBLICATIONS

Xiaojuan Yu, et al., "Structural basis for the neutralization of MERS-CoV by a human monoclonal antibody MERS-27", Scientific Reports, vol. 5, Issue 13133, 2015, pp. 1-11.
Tianlei Ying, et al., "Exceptionally Potent Neutralization of Middle East Respiratory Syndrome Coronavirus by Human Monoclonal Antibodies", Journal of Virology, vol. 88, No. 14, Jul. 2014, pp. 7796-7805.

* cited by examiner

AWKLFDDGV (SEQ ID NO: 21)

○ Charged (negative)
○ Charged (positive)
⊙ Glycine
⊗ Hydrophobic
⊘ Metal
○ Polar
⊘ Unspecified residue
○ Water
○ Hydration site
⊘ Hydration site (displaced)
--- Distance
→ H-bond
--- Metal coordination
▭ Pi-Pi stacking
◇ Pi-cation
--- Salt bridge
··· Solvent exposure

SMSGFSKPHD (SEQ ID NO: 23)

SEQUENCE LISTING

```
<160> NUMBER OF SEQ ID NOS: 50

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Tyr Pro Ala Val Gly Tyr Thr
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Tyr Pro Ala Val Gly Tyr Asn
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Tyr Pro Ala Gln Gly Tyr Thr
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Tyr Pro Ala Trp Gly Tyr Thr
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Tyr Pro Ala Lys Gly Tyr Thr
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 6

Arg Arg Pro Ala Val Gly Tyr Asp Thr
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Tyr Pro Ala Val Gly Tyr Thr Lys
1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Tyr Pro Arg Val Gly Tyr Thr
1               5

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asn Ala Gly Ser Leu Leu Ser Gly Trp Gly
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Pro Phe Lys Leu Ser Leu His Leu
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Leu Gly Asp Gly Cys Thr Arg
1               5

<210> SEQ ID NO 12

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Thr Gln Ser His Gln
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asp Glu Lys Gly Pro Lys Trp Lys Arg
1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence:
      Synthetic peptide

<400> SEQUENCE: 14

Thr Cys Ser Tyr Thr Met Glu Ala
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Gly Gly Gln Ala Asn Gln
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Phe Phe Phe Leu Ser Arg Ile Phe
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17
```

Asp Asp Asp Asp Asp Asp Asp
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Ser Glu Ile Gln Pro Arg
1               5

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Lys Thr Cys Glu Asn Leu Ala Asp Thr Tyr
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Ala Asp Asp Asp Asp Asp
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence:
      Synthetic peptide

<400> SEQUENCE: 21

Ala Trp Lys Leu Phe Asp Asp Gly Val
1               5

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence:
      Synthetic peptide

<400> SEQUENCE: 22

Ala Ala Gly Met Gly Phe Phe Gly Ala Arg
1               5                   10

<210> SEQ ID NO 23
<211> LENGTH: 10
<212> TYPE: PRT
<213> ORGANISM: Artificial Sequence
<220> FEATURE:

-continued

```
<223> OTHER INFORMATION: Description of Artificial Sequence:
      Synthetic peptide

<400> SEQUENCE: 23

Ser Met Ser Gly Phe Ser Lys Pro His Asp
1               5                   10

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence:
      Synthetic peptide

<400> SEQUENCE: 24

Arg Gly Ser Ala Leu Thr His Leu Pro
1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence:
      Synthetic peptide

<400> SEQUENCE: 25

Asn Arg Trp Cys Phe Ala Gly Asp Asp
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence:
      Synthetic peptide

<400> SEQUENCE: 26

Asp Glu Asp Asp Asp
1               5

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence:
      Synthetic peptide

<400> SEQUENCE: 27

Lys Ile Ala Lys Val Ala Leu Lys Ala Leu
1               5                   10

<210> SEQ ID NO 28
<211> LENGTH: 1353
<212> TYPE: PRT
<213> ORGANISM: Human betacoronavirus

<400> SEQUENCE: 28

Met Ile His Ser Val Phe Leu Leu Met Phe Leu Leu Thr Pro Thr Glu
1               5                   10                  15

Ser Tyr Val Asp Val Gly Pro Asp Ser Val Lys Ser Ala Cys Ile Glu
            20                  25                  30

Val Asp Ile Gln Gln Thr Phe Phe Asp Lys Thr Trp Pro Arg Pro Ile
```

```
              35                  40                  45
Asp Val Ser Lys Ala Asp Gly Ile Ile Tyr Pro Gln Gly Arg Thr Tyr
 50                  55                  60

Ser Asn Ile Thr Ile Thr Tyr Gln Gly Leu Phe Pro Tyr Gln Gly Asp
 65                  70                  75                  80

His Gly Asp Met Tyr Val Tyr Ser Ala Gly His Ala Thr Gly Thr Thr
                     85                  90                  95

Pro Gln Lys Leu Phe Val Ala Asn Tyr Ser Gln Asp Val Lys Gln Phe
                100                 105                 110

Ala Asn Gly Phe Val Val Arg Ile Gly Ala Ala Ala Asn Ser Thr Gly
                115                 120                 125

Thr Val Ile Ile Ser Pro Ser Thr Ala Thr Ile Arg Lys Ile Tyr
    130                 135                 140

Pro Ala Phe Met Leu Gly Ser Ser Val Gly Asn Phe Ser Asp Gly Lys
145                 150                 155                 160

Met Gly Arg Phe Phe Asn His Thr Leu Val Leu Leu Pro Asp Gly Cys
                    165                 170                 175

Gly Thr Leu Leu Arg Ala Phe Tyr Cys Ile Leu Glu Pro Arg Ser Gly
                180                 185                 190

Asn His Cys Pro Ala Gly Asn Ser Tyr Thr Ser Phe Ala Thr Tyr His
                195                 200                 205

Thr Pro Ala Thr Asp Cys Ser Asp Gly Asn Tyr Asn Arg Asn Ala Ser
    210                 215                 220

Leu Asn Ser Phe Lys Glu Tyr Phe Asn Leu Arg Asn Cys Thr Phe Met
225                 230                 235                 240

Tyr Thr Tyr Asn Ile Thr Glu Asp Glu Ile Leu Glu Trp Phe Gly Ile
                    245                 250                 255

Thr Gln Thr Ala Gln Gly Val His Leu Phe Ser Ser Arg Tyr Val Asp
                260                 265                 270

Leu Tyr Gly Gly Asn Met Phe Gln Phe Ala Thr Leu Pro Val Tyr Asp
    275                 280                 285

Thr Ile Lys Tyr Tyr Ser Ile Ile Pro His Ser Ile Arg Ser Ile Gln
    290                 295                 300

Ser Asp Arg Lys Ala Trp Ala Ala Phe Tyr Val Tyr Lys Leu Gln Pro
305                 310                 315                 320

Leu Thr Phe Leu Leu Asp Phe Ser Val Asp Gly Tyr Ile Arg Arg Ala
                325                 330                 335

Ile Asp Cys Gly Phe Asn Asp Leu Ser Gln Leu His Cys Ser Tyr Glu
                340                 345                 350

Ser Phe Asp Val Glu Ser Gly Val Tyr Ser Val Ser Ser Phe Glu Ala
                355                 360                 365

Lys Pro Ser Gly Ser Val Val Glu Gln Ala Glu Gly Val Glu Cys Asp
                370                 375                 380

Phe Ser Pro Leu Leu Ser Gly Thr Pro Pro Gln Val Tyr Asn Phe Lys
385                 390                 395                 400

Arg Leu Val Phe Thr Asn Cys Asn Tyr Asn Leu Thr Lys Leu Leu Ser
                    405                 410                 415

Leu Phe Ser Val Asn Asp Phe Thr Cys Ser Gln Ile Ser Pro Ala Ala
                420                 425                 430

Ile Ala Ser Asn Cys Tyr Ser Ser Leu Ile Leu Asp Tyr Phe Ser Tyr
                435                 440                 445

Pro Leu Ser Met Lys Ser Asp Leu Ser Val Ser Ser Ala Gly Pro Ile
                450                 455                 460
```

```
Ser Gln Phe Asn Tyr Lys Gln Ser Phe Ser Asn Pro Thr Cys Leu Ile
465                 470                 475                 480

Leu Ala Thr Val Pro His Asn Leu Thr Thr Ile Thr Lys Pro Leu Lys
                485                 490                 495

Tyr Ser Tyr Ile Asn Lys Cys Ser Arg Leu Leu Ser Asp Asp Arg Thr
            500                 505                 510

Glu Val Pro Gln Leu Val Asn Ala Asn Gln Tyr Ser Pro Cys Val Ser
        515                 520                 525

Ile Val Pro Ser Thr Val Trp Glu Asp Gly Asp Tyr Arg Lys Gln
530                 535                 540

Leu Ser Pro Leu Glu Gly Gly Gly Trp Leu Val Ala Ser Gly Ser Thr
545                 550                 555                 560

Val Ala Met Thr Glu Gln Leu Gln Met Gly Phe Gly Ile Thr Val Gln
                565                 570                 575

Tyr Gly Thr Asp Thr Asn Ser Val Cys Pro Lys Leu Glu Phe Ala Asn
            580                 585                 590

Asp Thr Lys Ile Ala Ser Gln Leu Gly Asn Cys Val Glu Tyr Ser Leu
        595                 600                 605

Tyr Gly Val Ser Gly Arg Gly Val Phe Gln Asn Cys Thr Ala Val Gly
610                 615                 620

Val Arg Gln Gln Arg Phe Val Tyr Asp Ala Tyr Gln Asn Leu Val Gly
625                 630                 635                 640

Tyr Tyr Ser Asp Asp Gly Asn Tyr Tyr Cys Leu Arg Ala Cys Val Ser
            645                 650                 655

Val Pro Val Ser Val Ile Tyr Asp Lys Glu Thr Lys Thr His Ala Thr
        660                 665                 670

Leu Phe Gly Ser Val Ala Cys Glu His Ile Ser Ser Thr Met Ser Gln
675                 680                 685

Tyr Ser Arg Ser Thr Arg Ser Met Leu Lys Arg Arg Asp Ser Thr Tyr
        690                 695                 700

Gly Pro Leu Gln Thr Pro Val Gly Cys Val Leu Gly Leu Val Asn Ser
705                 710                 715                 720

Ser Leu Phe Val Glu Asp Cys Lys Leu Pro Leu Gly Gln Ser Leu Cys
                725                 730                 735

Ala Leu Pro Asp Thr Pro Ser Thr Leu Thr Pro Arg Ser Val Arg Ser
            740                 745                 750

Val Pro Gly Glu Met Arg Leu Ala Ser Ile Ala Phe Asn His Pro Ile
        755                 760                 765

Gln Val Asp Gln Leu Asn Ser Ser Tyr Phe Lys Leu Ser Ile Pro Thr
770                 775                 780

Asn Phe Ser Phe Gly Val Thr Gln Glu Tyr Ile Gln Thr Thr Ile Gln
785                 790                 795                 800

Lys Val Thr Val Asp Cys Lys Gln Tyr Val Cys Asn Gly Phe Gln Lys
                805                 810                 815

Cys Glu Gln Leu Leu Arg Glu Tyr Gly Gln Phe Cys Ser Lys Ile Asn
            820                 825                 830

Gln Ala Leu His Gly Ala Asn Leu Arg Gln Asp Asp Ser Val Arg Asn
        835                 840                 845

Leu Phe Ala Ser Val Lys Ser Ser Gln Ser Ser Pro Ile Ile Pro Gly
850                 855                 860

Phe Gly Gly Asp Phe Asn Leu Thr Leu Leu Glu Pro Val Ser Ile Ser
865                 870                 875                 880
```

```
Thr Gly Ser Arg Ser Ala Arg Ser Ala Ile Glu Asp Leu Leu Phe Asp
            885                 890                 895

Lys Val Thr Ile Ala Asp Pro Gly Tyr Met Gln Gly Tyr Asp Asp Cys
            900                 905                 910

Met Gln Gln Gly Pro Ala Ser Ala Arg Asp Leu Ile Cys Ala Gln Tyr
            915                 920                 925

Val Ala Gly Tyr Lys Val Leu Pro Pro Leu Met Asp Val Asn Met Glu
930                 935                 940

Ala Ala Tyr Thr Ser Ser Leu Leu Gly Ser Ile Ala Gly Val Gly Trp
945                 950                 955                 960

Thr Ala Gly Leu Ser Ser Phe Ala Ala Ile Pro Phe Ala Gln Ser Ile
            965                 970                 975

Phe Tyr Arg Leu Asn Gly Val Gly Ile Thr Gln Gln Val Leu Ser Glu
            980                 985                 990

Asn Gln Lys Leu Ile Ala Asn Lys Phe Asn Gln Ala Leu Gly Ala Met
            995                 1000                1005

Gln Thr Gly Phe Thr Thr Thr Asn Glu Ala Phe Gln Lys Val Gln
    1010                1015                1020

Asp Ala Val Asn Asn Asn Ala Gln Ala Leu Ser Lys Leu Ala Ser
    1025                1030                1035

Glu Leu Ser Asn Thr Phe Gly Ala Ile Ser Ala Ser Ile Gly Asp
    1040                1045                1050

Ile Ile Gln Arg Leu Asp Val Leu Glu Gln Asp Ala Gln Ile Asp
    1055                1060                1065

Arg Leu Ile Asn Gly Arg Leu Thr Thr Leu Asn Ala Phe Val Ala
    1070                1075                1080

Gln Gln Leu Val Arg Ser Glu Ser Ala Ala Leu Ser Ala Gln Leu
    1085                1090                1095

Ala Lys Asp Lys Val Asn Glu Cys Val Lys Ala Gln Ser Lys Arg
    1100                1105                1110

Ser Gly Phe Cys Gly Gln Gly Thr His Ile Val Ser Phe Val Val
    1115                1120                1125

Asn Ala Pro Asn Gly Leu Tyr Phe Met His Val Gly Tyr Tyr Pro
    1130                1135                1140

Ser Asn His Ile Glu Val Val Ser Ala Tyr Gly Leu Cys Asp Ala
    1145                1150                1155

Ala Asn Pro Thr Asn Cys Ile Ala Pro Val Asn Gly Tyr Phe Ile
    1160                1165                1170

Lys Thr Asn Asn Thr Arg Ile Val Asp Glu Trp Ser Tyr Thr Gly
    1175                1180                1185

Ser Ser Phe Tyr Ala Pro Glu Pro Ile Thr Ser Leu Asn Thr Lys
    1190                1195                1200

Tyr Val Ala Pro Gln Val Thr Tyr Gln Asn Ile Ser Thr Asn Leu
    1205                1210                1215

Pro Pro Pro Leu Leu Gly Asn Ser Thr Gly Ile Asp Phe Gln Asp
    1220                1225                1230

Glu Leu Asp Glu Phe Phe Lys Asn Val Ser Thr Ser Ile Pro Asn
    1235                1240                1245

Phe Gly Ser Leu Thr Gln Ile Asn Thr Thr Leu Leu Asp Leu Thr
    1250                1255                1260

Tyr Glu Met Leu Ser Leu Gln Gln Val Val Lys Ala Leu Asn Glu
    1265                1270                1275

Ser Tyr Ile Asp Leu Lys Glu Leu Gly Asn Tyr Thr Tyr Tyr Asn
```

```
                1280                1285                1290
Lys Trp Pro Trp Tyr Ile Trp Leu Gly Phe Ile Ala Gly Leu Val
    1295                1300                1305
Ala Leu Ala Leu Cys Val Phe Phe Ile Leu Cys Cys Thr Gly Cys
1310                1315                1320
Gly Thr Asn Cys Met Gly Lys Leu Lys Cys Asn Arg Cys Cys Asp
    1325                1330                1335
Arg Tyr Glu Glu Tyr Asp Leu Glu Pro His Lys Val His Val His
    1340                1345                1350

<210> SEQ ID NO 29
<211> LENGTH: 251
<212> TYPE: PRT
<213> ORGANISM: Human betacoronavirus

<400> SEQUENCE: 29

Ala Asp Gly Ile Gln Glu Ala Lys Pro Ser Gly Ser Val Val Glu Gln
1               5                   10                  15
Ala Glu Gly Val Glu Cys Asp Phe Ser Pro Leu Leu Ser Gly Thr Pro
                20                  25                  30
Pro Gln Val Tyr Asn Phe Lys Arg Leu Val Phe Thr Asn Cys Asn Tyr
            35                  40                  45
Asn Leu Thr Lys Leu Leu Ser Leu Phe Ser Val Asn Asp Phe Thr Cys
        50                  55                  60
Ser Gln Ile Ser Pro Ala Ala Ile Ala Ser Asn Cys Tyr Ser Ser Leu
65                  70                  75                  80
Ile Leu Asp Tyr Phe Ser Tyr Pro Leu Ser Met Lys Ser Asp Leu Ser
                85                  90                  95
Val Ser Ser Ala Gly Pro Ile Ser Gln Phe Asn Tyr Lys Gln Ser Phe
            100                 105                 110
Ser Asn Pro Thr Cys Leu Ile Leu Ala Thr Val Pro His Asn Leu Thr
        115                 120                 125
Thr Ile Thr Lys Pro Leu Lys Tyr Ser Tyr Ile Asn Lys Cys Ser Arg
130                 135                 140
Leu Leu Ser Asp Asp Arg Thr Glu Val Pro Gln Leu Val Asn Ala Asn
145                 150                 155                 160
Gln Tyr Ser Pro Cys Val Ser Ile Val Pro Ser Thr Val Trp Glu Asp
                165                 170                 175
Gly Asp Tyr Tyr Arg Lys Gln Leu Ser Pro Leu Glu Gly Gly Gly Trp
            180                 185                 190
Leu Val Ala Ser Gly Ser Thr Val Ala Met Thr Glu Gln Leu Gln Met
        195                 200                 205
Gly Phe Gly Ile Thr Val Gln Tyr Gly Thr Asp Thr Asn Ser Val Cys
    210                 215                 220
Pro Lys Leu Glu Phe Ala Asn Asp Thr Lys Ile Ala Ser Gln Leu Gly
225                 230                 235                 240
Asn Cys Val Glu Tyr His His His His His
                245                 250

<210> SEQ ID NO 30
<211> LENGTH: 9
<212> TYPE: PRT
<213> ORGANISM: Artificial Sequence
<220> FEATURE:
<223> OTHER INFORMATION: Peptide interacting with 4NJL

<400> SEQUENCE: 30
```

Asn Arg Trp Cys Phe Ala Gly Asp Asp
1               5

<210> SEQ ID NO 31
<211> LENGTH: 9
<212> TYPE: PRT
<213> ORGANISM: Artificial Sequence
<220> FEATURE:
<223> OTHER INFORMATION: Peptide interacting with 4NJL

<400> SEQUENCE: 31

Arg Pro Pro Gly Phe Ser Pro Phe Arg
1               5

<210> SEQ ID NO 32
<211> LENGTH: 10
<212> TYPE: PRT
<213> ORGANISM: Artificial Sequence
<220> FEATURE:
<223> OTHER INFORMATION: Peptide interacting with 4NJL

<400> SEQUENCE: 32

Ala Ala Gly Met Gly Phe Phe Gly Ala Arg
1               5                   10

<210> SEQ ID NO 33
<211> LENGTH: 9
<212> TYPE: PRT
<213> ORGANISM: Artificial Sequence
<220> FEATURE:
<223> OTHER INFORMATION: Peptide interacting with 4NJL

<400> SEQUENCE: 33

Ser Val Ala Gly Arg Ala Gln Gly Met
1               5

<210> SEQ ID NO 34
<211> LENGTH: 9
<212> TYPE: PRT
<213> ORGANISM: Artificial Sequence
<220> FEATURE:
<223> OTHER INFORMATION: Peptide interacting with 4NJL

<400> SEQUENCE: 34

Lys Ile Lys Phe Leu Lys Val Leu Thr
1               5

<210> SEQ ID NO 35
<211> LENGTH: 10
<212> TYPE: PRT
<213> ORGANISM: Artificial Sequence
<220> FEATURE:
<223> OTHER INFORMATION: Peptide interacting with 4NJL

<400> SEQUENCE: 35

Phe Phe Cys Phe Lys Gly Thr Pro Cys Gly
1               5                   10

<210> SEQ ID NO 36
<211> LENGTH: 9
<212> TYPE: PRT
<213> ORGANISM: Artificial Sequence
<220> FEATURE:
<223> OTHER INFORMATION: Peptide interacting with 4NJL

<400> SEQUENCE: 36

Val Gly Val Gly Gly Gly Phe Gly Arg
1               5

<210> SEQ ID NO 37
<211> LENGTH: 7
<212> TYPE: PRT
<213> ORGANISM: Artificial Sequence
<220> FEATURE:
<223> OTHER INFORMATION: Peptide interacting with 4NJL

<400> SEQUENCE: 37

Asn Gly Val Gln Pro Lys Tyr
1               5

<210> SEQ ID NO 38
<211> LENGTH: 9
<212> TYPE: PRT
<213> ORGANISM: Artificial Sequence
<220> FEATURE:
<223> OTHER INFORMATION: Peptide interacting with 4NJL

<400> SEQUENCE: 38

Asp Glu Lys Gly Pro Lys Trp Lys Arg
1               5

<210> SEQ ID NO 39
<211> LENGTH: 9
<212> TYPE: PRT
<213> ORGANISM: Artificial Sequence
<220> FEATURE:
<223> OTHER INFORMATION: Peptide interacting with 4NJL

<400> SEQUENCE: 39

Glu Pro Phe Lys Leu Ser Leu His Leu
1               5

<210> SEQ ID NO 40
<211> LENGTH: 10
<212> TYPE: PRT
<213> ORGANISM: Artificial Sequence
<220> FEATURE:
<223> OTHER INFORMATION: Peptide interacting with 4NJL

<400> SEQUENCE: 40

Asn Ala Gly Ser Leu Leu Ser Gly Trp Gly
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Peptide interacting with 4NJL

<400> SEQUENCE: 41

Glu Val Ala Ser Phe Asp Lys Ser Lys Leu Lys
1               5                   10

<210> SEQ ID NO 42
<211> LENGTH: 7
<212> TYPE: PRT
<213> ORGANISM: Artificial Sequence
<220> FEATURE:
<223> OTHER INFORMATION: Peptide interacting with 4NJL

<400> SEQUENCE: 42

Met Arg Thr Gly Asn Ala Asp

```
<210> SEQ ID NO 43
<211> LENGTH: 10
<212> TYPE: PRT
<213> ORGANISM: Artificial Sequence
<220> FEATURE:
<223> OTHER INFORMATION: Peptide interacting with 4NJL

<400> SEQUENCE: 43

Leu Arg Pro Ala Ile Leu Val Arg Ile Lys
1               5                   10

<210> SEQ ID NO 44
<211> LENGTH: 5
<212> TYPE: PRT
<213> ORGANISM: Artificial Sequence
<220> FEATURE:
<223> OTHER INFORMATION: Peptide interacting with 4NJL

<400> SEQUENCE: 44

Ile Ile Gly Gly Arg
1               5

<210> SEQ ID NO 45
<211> LENGTH: 11
<212> TYPE: PRT
<213> ORGANISM: Artificial Sequence
<220> FEATURE:
<223> OTHER INFORMATION: Peptide interacting with 4NJL

<400> SEQUENCE: 45

Glu Asp Gly Leu His Pro Arg Leu Cys Ser Cys
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Peptide interacting with 4NJL

<400> SEQUENCE: 46

Phe Cys Lys Ser Leu Pro Leu Pro Leu Ser Val Lys
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Peptide interacting with 4NJL

<400> SEQUENCE: 47

Ser Arg Ser Glu Leu Ile Val His Gln Arg
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Peptide interacting with 4NJL

<400> SEQUENCE: 48

Glu Gln Cys Arg Glu Glu Glu Asp Asp Arg
1               5                   10
```

```
<210> SEQ ID NO 49
<211> LENGTH: 11
<212> TYPE: PRT
<213> ORGANISM: Artificial Sequence
<220> FEATURE:
<223> OTHER INFORMATION: Peptide interacting with 4NJL

<400> SEQUENCE: 49

Leu Arg Pro Ala Val Ile Arg Pro Lys Gly Lys
1               5                   10

<210> SEQ ID NO 50
<211> LENGTH: 7
<212> TYPE: PRT
<213> ORGANISM: Artificial Sequence
<220> FEATURE:
<223> OTHER INFORMATION: Peptide interacting with 4NJL

<400> SEQUENCE: 50

Asp Asp Asp Asp Asp Asp Asp
1               5
```

ANTIVIRAL PEPTIDES FOR TREATMENT OF THE MIDDLE EAST RESPIRATORY SYNDROME

CROSS-REFERENCE TO RELATED APPLICATION

This application claims priority to U.S. Provisional Application No. 62/823,912, filed Mar. 26, 2019, which is hereby incorporated by reference for all purposes.

SEQUENCE LISTING

This application contains a Sequence Listing which has been submitted electronically in ASCII format and is hereby incorporated by reference in its entirety. Said ASCII copy, created on Mar. 25, 2020, is named 521589US_ST25.txt and is 23.9 kb in size.

BACKGROUND OF THE INVENTION

Field of the Invention

The present invention relates to the fields of structural bioinformatics and virology and to a peptide-based treatment of Middle East Respiratory Syndrome (MERS) caused by the Middle East Respiratory Syndrome Coronavirus (MERS-CoV).

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

Middle East Respiratory Syndrome (MERS) is a respiratory disease caused by MERS coronavirus (MERS-CoV); Petersen et al. *Middle East Respiratory Syndrome-advancing the public health and research agenda on MERS-lessons from the South Korea outbreak.* Int J Infect Dis 2015; 36:54-5; and Zaki et al. *Isolation of a Novel Coronavirus from a Man with Pneumonia in Saudi Arabia.* New England Journal of Medicine 2012; 367(19):1814-20.

While MERS-CoV shares similarity with bat coronaviruses HKU4 and HKU5, unlike many zoonotic viruses it can be transmitted in humans person-to-person; Assiri et al. "Hospital Outbreak of Middle East Respiratory Syndrome Coronavirus." The New England Journal of Medicine 2013; 369(5):407-16.

MERS was first reported in Saudi Arabia in 2012 and has spread to other countries in or near the Arabian Peninsula including the United Arab Emirates, Qatar, Oman, Jordan, Kuwait, Yemen, and Lebanon AlMutairi et al. *Look at the Middle Eastern Respiratory Syndrome (MERS-CoV) Outbreak in Saudi Arabia.* Journal of Nursing & Care 2015; 4:2167-11683. The World Health Organization (WHO) estimated in December, 2017 that MERS-CoV caused 740 deaths and reported 2121 confirmed cases of MERS-CoV infection in 27 countries. While the MERS virus has been contained, it has not been eradicated, for example, three years after the identification of the virus in Saudi Arabia it reemerged in a South Korean outbreak.

The global spread of MERS-CoV infection to many countries and the associated costs in human lives and care have made the development of an effective therapeutic against MERS-CoV infection a high priority.

Currently, there is no effective treatment or vaccine against the MERS-CoV virus. Treatment is now substantially limited to palliative care by relieving the symptoms of the disease, boosting immune function, or by administering antiviral drugs. Additionally, preventive measures are taken to reduce the risk of infection of non-infected people or re-infection of previously infected patients; Liu et al. *Testing of Middle East respiratory syndrome coronavirus replication inhibitors for the ability to block viral entry.* Antimicrob Agents Chemother 2015; 59(1):742-4.

Some current treatment options for MERS consist of administering intravenous immunoglobulin (IVIG), interferon, and/or Ribavirin. However, there is no evidence that IVIG has anti-MERS-CoV activity and while Ribavirin may exert an antiviral effect, it has many adverse side effects. Accordingly, there is a need for the development of additional therapeutic agents with increased efficacy to treat MERS and overcome the adverse side effects observed in the current modes of therapy for MERS.

In view of the numerous adverse effects of chemically-based drugs, there is a growing interest in treatment alternatives including vaccines, neutralizing monoclonal antibodies, and peptide-based therapies, including antimicrobial peptide (AMP) therapy; Albericio et al. Therapeutic peptides. Future Medicinal Chemistry 2012; 4(12):1527-316Qureshi et al, *AVPdb: a database of experimentally validated antiviral peptides targeting medically important viruses.* Nucleic Acids Research 2014; 42 (Database issue): D1147-D53.7.

Various antimicrobial peptides have been characterized including synthetic anti-lipopolysaccharide peptides (SALPs) that inhibit influenza A virus replication by blocking cellular attachment; Hoffman et al., Antiviral Res. (2014) 104, 23-33. The P9 peptide, which comprises a 30 residue long segment of the mammalian β-defensin-4 peptide has been reported to have a broad-spectrum antiviral activity against multiple respiratory viruses; Zhao et al., SciRep (2016) 6, 22008, published on line Feb. 15, 2016, doi: 10.1038/srep22008; and the lacrain peptide RYPAVGYT (SEQ ID NO: 1) has been described as antibacterial peptide by Chaparro, et al., J. Antimicrob. Agents 48(3):277-285 (2016).

MERS-CoV spike protein represents a possible target for peptide-based therapy because this protein participates in entry and infection of host cells by MERS-CoV and the virus binds to dipeptidyl peptidase-4 (DDP4) on host cells via a spike protein receptor binding domain (RBD); Raj et al., Nature (2013) 495, 251-256; Lu et al. Nature (2013) 500, 227-231 and WO2014/045254.

In view of the limitations and drawbacks of existing MERS therapies, the present disclosure describes new peptide compounds that bind to and interact with the MERS-CoV spike protein, especially the RBD, competitively inhibit MERS-CoV binding to its host cell receptors such as DPP4, and/or otherwise disable the interaction between the viral spike protein and the cellular DPP4 receptor, to thereby provide a method to treat and prevent progression of a viral infection.

SUMMARY OF THE INVENTION

One aspect of the present disclosure is to provide a method for preventing, inhibiting, reducing the severity of, or otherwise treating, an infection caused by MERS-CoV by administering one or more peptides or other peptidomimetics that bind to the MERS-CoV spike protein or its receptor binding domain (RBD) and other determinants like heptad repeats 1 and 2 (HR1, HR2) involved in viral infection thereby inhibiting the interaction of the virus with its host cells.

A related aspect of the invention includes a peptide analog, covalently-modified peptide, or peptidomimetic that binds to the MERS-CoV spike protein or its RBD and which chemically differs from a conventional peptide having an N and C terminal and comprising unmodified L-amino acid residues.

Another aspect of the invention is a pharmaceutical composition, including inhalable compositions, comprising one or more peptides, peptide analogs, modified peptides, or peptidomimetics that bind to MERS-CoV spike protein, its RBD or the HR1 or HR2. These include the peptides comprising the amino acid sequences of SEQ ID NOS: 1-27 and 30-50, their analogs, modified peptides, and peptidomimetics based on these sequences.

Yet another aspect of the invention is a method for modifying a peptide or peptidomimetic that binds to the MERS-CoV spike protein or its RBD using structural data in Protein Data Bank (PDB) ID number 4KQZ, which depicts the 3D structure of the receptor binding domain (RBD) of MERS-CoV spike protein or PDB ID number 4NJL, to obtain a peptide or peptidomimetic that has increased antiviral activity relative to that its unmodified, parent form.

BRIEF DESCRIPTION OF THE DRAWINGS

A more complete appreciation of the disclosure and many of the attendant advantages of the subject matter disclosed therein will be readily obtained and better understood by reference to the following detailed description when considered in connection with the accompanying drawings, wherein.

Figure 1:
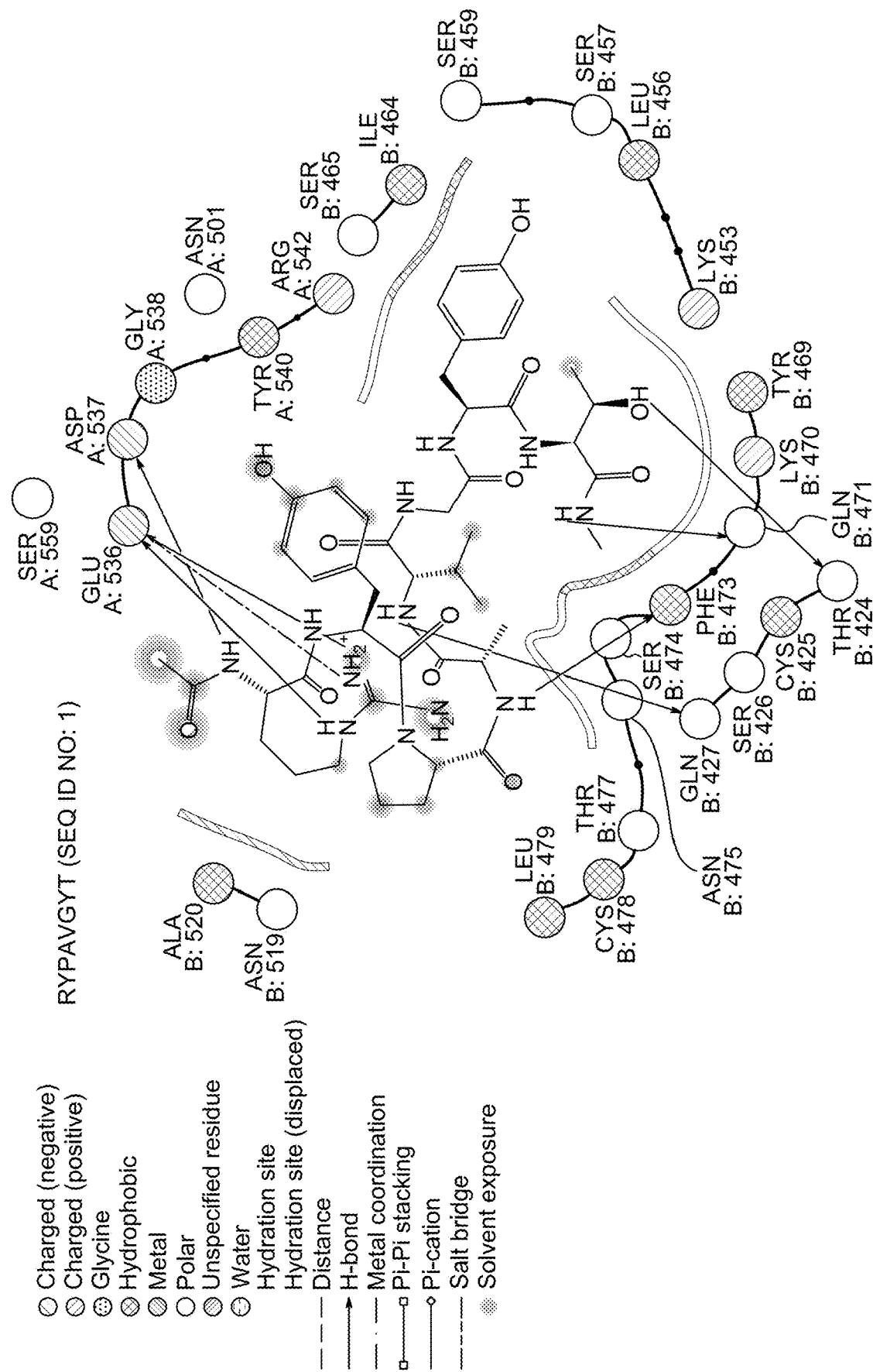
FIG. 1 shows the interactions of a peptide of SEQ ID NO: 1 with MERS-CoV receptor binding domain of spike protein of SEQ ID NO: 28. The peptide forms seven hydrogen bonds with Thr-424, Gln-427, Phe-473, Glu-536, Asp-537, and Gln-471 and exhibits three aromatic hydrogen interactions. Glu-536 forms two hydrogen bonds and one salt bridge interaction.

Additional peptides and peptide interactions with MERS S protein are disclosed by, and incorporated by reference to, the priority document U.S. Provisional Application No. 62/823,912. In some embodiments, one or more of these peptides may be used instead of, or in addition to, the peptides described by SEQ ID NOS: 1 to 27 or SEQ ID NOS: 30 to 50. Analysis of the peptides of SEQ ID NOS: 1-27 is provided in the figures using PDB 4NJL as a target.

DETAILED DESCRIPTION

MERS Spike Protein (S Protein) is a glycoprotein that forms a trimer in the virus envelop. S protein can be cleaved by host proteases into an N-terminal S1 subunit and a membrane-bound C-terminal S2 region. S protein is involved in recognition of host cells by the MARS virus. The S1 subunit of the Spike protein comprises the RBD or receptor binding domain. The S2 subunit comprises the HR1 and HR2 regions. The S1 subunit is responsible for the binding of the virion via its receptor binding domain (RBD) to the its host cell receptor, dipeptidyl peptidase-4 (DPP4), while the S2 subunit mediates the fusion between viral and cellular membranes through the interaction between its HR1 and HR2 domains and entry of the viral genetic materials into the host cell. The Spike (S) protein of MERS-CoV plays important roles in virus attachment, fusion, and entry into the target cell. Peptides, modified peptides and peptidomimetics as disclosed herein can bind to or otherwise interact with the MERS S protein and inhibit infectivity of MERS virus.

Embodiments of the invention include, but are not limited to the following.

One embodiment of the invention is a method for treating Middle East respiratory syndrome-related coronavirus (MERS-CoV), comprising contacting the virus with a composition comprising a peptide that binds to the S1 subunit of the MERS-CoV spike protein or to its RBD or to other S protein determinants such as HR1 and HR2.

Typically a composition containing a peptide that targets the S protein of MERS-CoV is administered to a subject at risk of MERS infection, such as a family member or co-worker of a MERS patient, or to a patient who has been exposed to MERS, diagnosed with MERS, or has the symptoms of MERS. Treatment may commence at the time of exposure or infection with MERS-CoV and can be continued until the virus is no longer present or active in the respiratory tract. For prophylaxis of a non-infected subject, treatment may continue for as long as there is a risk of exposure to the virus. A peptide-based therapy such as that disclosed herein can reduce the risk of infection, reduce passage of the virus between viral hosts, lessen fever, cough and respiratory symptoms, nausea, vomiting and diarrhea of an infection, reduce the risk of kidney failure, speed recovery of an infected subject, and shorten the duration of illness for example, by 1, 2, 3, 4, or more days.

This method may involve selecting a particular type of patient, for example, a patient at higher risk of infection, morbidity, or mortality from MERS-CoV. In some embodiments, the patient is a smoker, a vaper, has chronic obstructive pulmonary disease, bronchial asthma, allergy, cystic fibrosis, influenza, rhinovirus infection, or another respiratory infection other than MERS-CoV. In some embodiments, a patient who expresses cellular receptors for MERS-CoV at a higher than normal level may be selected. For example, the MERS-CoV receptor dipeptidyl peptidase-4 (DPP4, CD26) is often upregulated in smokers and patients having COPD. In other embodiments, the patient does not have any of these conditions and is a substantially normal, healthy person.

Advantageously the subject is a human, male or female, child (at least 0, 0.25, 0.5, 0.75, 1, 2, 3, 4, 5, 6, 7, 8, 9, 10, 11, 12, 13, 14, 15, 16, 17, <18 years of age) or adult (at least 18, 21, 30, 40, 50, 60, 70, 80, or 90 years of age) especially a human subject at a high risk of infection, morbidity or mortality due to MERS (e.g. traveler to area where MERS is prevalent, a smoker or person with COPD) or an already infected person.

Subjects can also include non-human animals that can be infected by MERS or which can act as carriers of MERS-CoV. These include camels, dromedaries, llamas, alpacas, sheep, horses, and swine, and other members of the families Suidae or Camelidae. Animals which express a MERS-CoV receptor dipeptidyl peptidase, such as one that has at least 90, 95, or 99% sequence identity with the human dipeptyl peptidase 4 (NCBI Reference Sequence: NP_001926.2, incorporated by reference) and which bind to MERS-CoV S protein are also included.

Inhibiting, ameliorating, reducing the severity of, treating, or preventing a disease, disorder or condition.

"Inhibiting" refers blocking of interfering with the full development of a disease, disorder or condition, for example, in a subject who is at risk for a disease, disorder or condition associated with, or caused by, MERS-CoV, such as MERS or MERS related conditions. Inhibiting includes reducing the risk of being infected, for example, down to 10, 20, 30, 40, 50, 60, 70, 80, or 90% of the risk of infection of an untreated subject or control subject.

"Treatment" refers to a therapeutic intervention that ameliorates a sign or symptom of a disease, disorder or condition, such as MERS and MERS related conditions, after it has begun to develop.

The terms "ameliorating" or "reducing the severity of" with reference to a disease, disorder, or pathological condition, refer to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, reduction in transmission rate, an improvement in the overall health or well-being of the subject, or by other parameters well known in the art that are specific to the particular disease. In some embodiments, MERS infection is ameliorated to the extent that its symptoms are barely detectable or not detectable at all. A subject may also have the severity of MERS infection reduced to an extent that renders it virtually asymptomatic but which results in a degree of immunity to the MERS virus.

"Preventing" a disease means inhibiting development of a disease in a subject who would normally be expected to develop the disease or be at increased risk for the disease. Upon MERS-CoV infection or exposure, even though the patient does not have symptoms of disease, administration of the compounds may be started before symptoms appear, and treatment may be continued indefinitely to prevent or delay onset or recurrence of disease.

Administration. The peptide, modified peptide, or peptidomimetic as disclosed herein, may be contacted with MERS-CoV by administering the peptide locally, regionally, or systemically to a subject in need thereof. It may be administered orally, intranasally, or intraocularly to a subject, administered to upper or lower respiratory system of a subject, or administered parenterally. Thus, the peptides, modified peptides, and peptidomimetics as disclosed herein can be administered by a variety of routes including oral, topical, parenteral (including subcutaneous, intravenous, intramuscular and intraperitoneal), vaginal, rectal, dermal, transdermal, intrathoracic, intraocular, or intranasal routes, or into the respiratory system or parts thereof, such as the upper respiratory system, lower respiratory system or lungs.

Respiratory system administration. In humans, MERS-CoV mainly replicates in the lower respiratory tract, particularly in the bronchiolar and alveolar epithelia and in alveolar epithelia cells. Advantageously a composition as disclosed herein will be formulated to direct it to a tissue to which MERS-CoV is trophic, such as to bronchiolar and alveolar epithelia and alveolar epithelia cells.

For inhalation therapy or prophylaxis, the composition may be formulated as droplets of a respirable size, such as within the range of 1, 2, 3, 4, to 5 µm. In some embodiments of the method disclosed herein a composition comprising a peptide, modified peptide or peptidomimetic that binds to MERS-CoV S protein or its RBD may be administered via an inhaler or nebulizer, preferably, so as to contact the respiratory tissues susceptible to, or infected with, MERS-CoV. Excipients, aerosol sizes, dosages and modes of respiratory administration may be formulated or selected by those skilled in the art of pharmacology taking into account the present disclosure.

Therapeutically effective amount or effective amount is an amount of an agent, such as a peptide which binds to MERS-CoV S protein, that is sufficient to prevent, inhibit, treat (including prophylaxis), reduce the severity of and/or ameliorate the symptoms and/or underlying causes of any of a disorder or disease, for example to prevent, inhibit, and/or treat MERS-CoV infection. In some embodiments, an "effective amount" is sufficient to reduce or eliminate a symptom of a disease, such as MERS or a MERS associated disorder or condition. For instance, this can be the amount necessary to inhibit viral replication or to measurably alter outward symptoms of the viral infection, such induction of T cells or antibodies. In general, this amount will be sufficient to measurably inhibit virus, such as MERS-CoV replication or infectivity. An "anti-viral agent" or "anti-viral drug" is an agent that exhibits virucidal or virustatic activity or which inhibits the lifecycle of the virus, for example, by preventing it from binding or entry into host cells or otherwise preventing its replication and transmission.

Dosage. The amount of a pharmaceutical composition administered to a subject varies and is dependent on the age and weight of the subject, the severity of the infection, and on pharmacokinetic factors like the half-life or rate at which the peptide is cleared from the respiratory system or other sites of viral attachment or infection. The dosage may be titrated based on patient status, half-life of the peptide or modified peptide, and route of administration so as to administer a dose that inhibits the symptoms of MERS or its transmission, attachment to host cells, host cell invasion, replication or release.

In some embodiments, a peptide or modified peptide may be administered in an amount of at least about 0.01, 0.02, 0.05, 0.1, 0.2, 0.5, 1, 2, 5, 10, 20, 50, 100, 120, 150, 200, 300, 400, 500, 600 or >600 mg/kg of patient weight (or any intermediate value within these values) although other dosages may provide beneficial results. The concentration of a dosage may be adjusted depending on route of administration. For example, when administered to the respiratory system, the concentration may be adjusted to maximize contact and binding between the peptide and MERS-CoV. Dosages and concentrations of peptides as disclosed herein may be determined by those skilled in the art.

A dosage may be administered as a single dose or as divided doses. In one embodiment, a dose is given 1, 2, 3, or 4 times daily and continued for 3-10 days, and typically 3, 4, 5, 6, 7 or 8 days post infection.

Additional Antiviral Ingredients.

In some embodiments, the method of treatment or prophylaxis disclosed herein may further comprise administering one, two or more additional antiviral agents, such as type I interferon, which can inhibit MERS-CoV replication in susceptible cells or which prevent or treat a secondary viral or bacterial infection. Advantageously, a combination of one or more peptides which target MERS-CoV S protein or its RBD, may exhibit an additive or synergistic antiviral effect, for example, on viral attachment, internalization, replication, or release. Other drugs include Ribivarin, Remdesivir (GS-5734), Actemra, Galidesivir (BCX4430), and/or REGN3048-3051, or with passive or active immune therapy, such as with MERS-CoV specific monoclonal or polyclonal antibodies, intravenous immunoglobulin (IVIG), MERS-CoV specific T cells, or with a MERS-CoV vaccine. Other antiviral drugs include, but not limited to, oseltamivir (Tamiflu), zanamivir (Relenza®), permivir (Rapivab®), dideoxynucleosides, azidothymidine, interferons and the like.

Peptide: Any compound composed of amino acids or amino acid analogs which are chemically bound together typically by peptide bonds. This term includes oligomers of amino acids, amino acid analog, or small and large peptides, including proteins.

Any chain of amino acids, regardless of length or post-translational modification (such as glycosylation or phosphorylation), is referred to as a peptide. In some embodiments, a peptide will have only L-amino acid residues covalently linked with normal peptide bonds and a conventional amino (N) and carboxy (C) terminals. In others this natural peptide structure will be modified by one or more covalent bounds not normally found in natural proteins or peptides.

The term peptide applies to amino acid polymers including naturally occurring amino acid polymers and non-naturally occurring amino acid polymers as well as polymers in which one or more amino acid residue is a non-natural amino acid, for example an artificial chemical mimetic of a corresponding naturally occurring amino acid. In some preferred embodiments, the peptides of the invention are no more than 4, 5, 6, 7, 8, 9, 10, 11, 12, 13, 14, 15, 20, 25 or 30 amino acid residues in length.

In some instances, the peptides or modified peptides described herein conforming to SEQ ID NOS: 1-27 or 30-50 are identified as "peptides", "antiviral peptides" or "MERS-CoV-binding" peptides instead of by direct reference to their structures or to their sequence identifiers.

Peptides, peptide analogs, modified peptides, peptidomimetics. Advantageously, the method as disclosed herein administers or uses a peptide comprising an amino acid sequence of that is at least 80, 85, 90, 95, 96, 97, 98, 99, or 100% identical to any one of SEQ ID NOS: 1 to 27, or to any one of SEQ ID NOS: 30-50, or to a fragment thereof having 4 to 20 amino acid residues of said amino acid sequence. The method may also employ a variant peptide or peptide analog based on any one of those described by SEQ ID NOS: 1-27 or 30-50 which can be produced by inserting, substituting or deleting 1, 2, 3, 4 or 5 amino acid residues described by SEQ ID NOS: 1-27 or 30-50, preferably no more than 1 or 2 residues. A variant peptide may also incorporate one or more D-amino acid residues, for example, it may replace a L-amino acid residue with the corresponding D-amino acid residue.

Modified peptides. In some embodiments, the peptide is covalently modified, thus producing a modified peptide. As used herein "modified peptide" means any structural modification to a peptide as disclosed herein.

Many peptide modifications are known in the art. In some embodiments one or more amino acid residues of the peptides of SEQ ID NO: 1-27 or 30-50 are substituted with an enantiomeric amino acid, e.g. replacing Ala with D-Ala, in other embodiments, an organic molecular may replace an amino or acidic group.

Unusual & Non-natural Amino Acids. Apart from the 20 natural L-amino acids, there is a multitude of non-natural or unusual amino acids available that can be built into synthetic peptides. There are many different reasons to incorporate non-natural amino acids, such as for example to enhance affinity, selectivity of stability of peptide drug leads. Another application is the use of non-natural amino acids for induction or stabilization of secondary structures (α-helices, β-sheets, β-turns). A large number of different non-natural amino acids can be incorporated into a peptide as disclosed herein. These include D-amino acids, homo amino acids, beta-homo amino acids, N-methyl amino acids, alpha-methyl amino acids, non-natural side chain variant amino acids and other unusual amino acids.

Replacement with organic groups. In some other embodiments, an amino acid residue of the peptide may be replaced with any organic molecule having an amino group and acidic group including, but not limited to β-alanine, fluorinated amino acid such as, but not limited to, L- and D-alanine, L- and D-phenylalanine, L- and D-hexylalanine, L- and D-phenylglycine, L- and D-cyclopropylalanine, substituted L- and D-phenyl alanine, L- and D-tyrosine, o-, m-, or p-aminobenzoic, o-, m-, or p-aminobenzine sulfonic acid, all isomers of aminonaphthoic acid, and the like.

Another well-established method is to replace amido nitrogen of a peptide bond with $CR_1R_2$, wherein $R_1$ and $R_2$ are independently hydrogen, optionally substituted alkyl, optionally substituted cycloalkyl, optionally substituted heterocycloalkyl, optionally substituted aryl, optionally substituted hetroaryl. In a preferred embodiment, $CR_1R_2$ is $CH_2$. Such substitutions preserve the shape of the molecule and most of the interactions of the peptide with its target biomolecule, but render the resulting molecule resistant to hydrolysis by proteolytic enzymes. Resistance to proteolytic degradation or cleavage can increase the half-life of a peptide, such as those described by SEQ ID NOS: 1-27 or 30-50, in a biological system, for example, in the blood or respiratory fluids of a subject.

In other embodiments, the N or C terminal of the peptide may be covalently modified, an internal amino acid or its side-chain may be covalently modified, or another covalent modification such as the conjugation of one or more terminal D or L amino acids, proteins, carbohydrates, lipids or other chemical structures.

N and C terminal modifications. A peptide according to the invention may be in substantially the form found in nature or as synthesized using L-amino acids, for example, it may comprise all L-amino acid residues and an unmodified N-terminal and C-terminal. Alternatively, the peptide may be further engineered or modified. For example, the N or C-terminal may be chemically modified or derivatized to improve pharmacokinetic properties such as solubility and stability. The N-terminus may be acylated by any acyl group of a carboxylic acid including amino acids and carbonic acid derivatives. A suitable acyl group includes, but not limited to, formyl, acetyl, propanyl, oxalate and succinyl. Similarly, the carboxyl terminus of the peptide may be amidated or esterified. Ammonia or any primary or secondary amine may be used to modify the carboxyl terminus. In particular, amines such as, but not limited to, methyl amine, ethyl amine, propyl amine, isopropyl amine, butyl amine, isobutyl amine, t-butyl amine, dimethyl amine, diethyl amine, dipropyl amine, diisopropyl amine, dibutyl amine, diisobutyl amine, di-t-butyl amine, aniline, metylanaline, and the like. Any alcohol may be used to form an ester at the C-terminus of a peptide including, but not limited to, methanol, ethanol, propanol, isopropanol, butanol, isobutanol, t-butanol, ascorbic acid, and the like. The C-terminus of a peptide may also be esterified with a phenolic compound including, but not limited to phenol, o-, m-, or p-hydroxyanisol, o-, m-, or p-cresol, and the like.

Sulphation. Tyrosine 0-sulfation is a posttranslational protein modification that often occurs among proteins of multicellular eukaryotic organisms. It has been estimated that as much as 1% of an organism's total proteins may be subjected to tyrosine sulfation. Tyrosine-sulfated proteins can enhance protein-protein interactions.

Protein phosphorylation is a posttranslational modification of proteins in which a serine, a threonine or a tyrosine residue is phosphorylated by a protein kinase by the addition of a covalently bound phosphate group. Protein kinases share a conserved catalytic domain, which catalyzes the transfer of the gamma-phosphate of ATP to a serine, threonine or tyrosine residue in protein substrates. Phosphorylation occurs mainly on the hydroxyl side chain of serine and threonine residues and, to a lesser extent, on the phenolic side chain of tyrosine residues. Biotinylation of peptides can be performed either at the N- or C-terminus.

Biotinylation at the N-terminus can be performed directly to the primary-terminal amino group, whereas biotinylation is usually performed at the ε-amino group of an (extra) C-terminal lysine. An important consideration when making a biotinylated peptide is to ensure there is a sufficient spacer arm between the biotin group and the amino acids in the peptide which are expected to interact with a macromolecule (such as an antibody). To avoid steric hindrance, a linker can be inserted between biotin and the peptide sequence. A hydrophobic straight chain spacer such as the 6-carbon ε-aminohexanoic (Ahx) is frequently applied or a hydrophilic tetrapeptide such as -SGSG- can be inserted.

Peptide conjugation. The N and C terminals of a peptide as disclosed herein may also be modified by the addition of one or more L-amino acid residues or D-amino acid residues or by the addition of other chemical moieties. For example, one or more additional amino acid residue(s) may be added to the N-terminus to improve the solubility of the peptide or enhance their bioavailability and increase their biological half-life time. The amino acid may be any molecule having an amino group and acidic group such as, but not limited to, a carboxyl group, sulfonic group, sulfate group, or phosphate having any chemical structure or configuration. Such amino acid include, but not limited to, enantiomeric D-amino acid of the amino found in proteins, β-alanine, L- and D-phenylglycine, substituted L- and D-phenyl alanine, L- and D-tyrosine, o-, m-, or p-aminobenzoic, o-, m-, or p-aminobenzine sulfonic acid, all isomers of aminonaphthoic acid, and the like. A peptide or peptidomimetic as disclosed herein, which binds to MERS-CoV S protein or its RBD, may be conjugated or crosslinked to another peptide or protein or other carrier at either or both terminals or via an internal amino acid residue.

Constrained peptides. In some embodiments, the peptide, modified peptide or peptidomimetic may be constrained so as to maintain a particular configuration efficient for binding or interaction with the S protein. Methods for producing constrained peptides include chemical crosslinking, cyclization, and substitution or a peptide with unnatural conformation-favoring amino acids. Methods for design of constrained peptides are described by, and incorporated by reference to, Bhardwaj, et al., Accurate de novo design of hyperstable constrained peptides, Nature volume 538, pages 329-335(2016).

Cell penetrating peptide. Cell-penetrating peptides (CPPs) are short peptides that facilitate cellular intake/uptake of various molecular components ranging from nano-sized particles to small chemical molecules and large fragments of DNA. The "cargo" is associated with the peptides either through chemical linkage via covalent bonds or through non-covalent interactions. Many CPPs are known in the art including those described by and incorporated by reference to Milletti F (August 2012). *Cell-penetrating peptides: classes, origin, and current landscape*. Drug Discovery Today. 17 (15-16): 850-60. doi:10.1016/j.drudis.2012.03.002. PMID 22465171; Stalmans S, et al. (2013). *Chemical-functional diversity in cell-penetrating peptides*. PLOS ONE. 8 (8): e71752. Bibcode:2013PLoSO. 871752S. doi:10.1371/journal.pone.0071752. PMC 3739727. PMID 23951237; Wagstaff K M, et al. (2006). *Protein transduction: cell penetrating peptides and their therapeutic applications*. Current Medicinal Chemistry. 13 (12): 1371-87. doi:10.2174/092986706776872871. PMID 16719783; and Okuyama M, et al. (February 2007). Small-molecule mimics of an alpha-helix for efficient transport of proteins into cells. Nature Methods. 4 (2): 153-9. In some embodiments of the invention one or more peptides that bind to MERS-CoV as disclosed herein may be combined with or conjugated to a CPP to facilitate binding of the peptide with virus, such as virus internalized in a host cell.

Modifications to the peptides disclosed herein may be carried out include, but are not limited to, pegylation (covalent attachment of one or more molecules of polyethylene glycol "PEG", or derivatives thereof); glycosylation (e.g., N-glycosylation), polysialylation and hesylation (with a hydroxyethyl starch); albumin fusion; albumin binding through, acylation (e.g. with a conjugated fatty acid chain); Fc-fusion; and fusion with a PEG mimetic. In some embodiments, linkers are used in such modifications. In some embodiments, the peptide as disclosed herein is covalently bound to at least one lipid or carbohydrate component, covalently bound to polyethylene glycol or PEG or to a dendritic polymer, or to an immunogenic carrier protein or to a scaffold protein.

Fatty acid conjugation. To improve peptide pharmacokinetics, conjugating the peptide to a lipid is a favored approach. It prolongs the half-life of the peptide in the circulation significantly. The most typical derivatization involves long-chain fatty acids. Fatty acid conjugated peptides can also be used for a number of different applications, e.g. for increasing their antibacterial activity or eukaryotic cell toxicity. For fatty acid conjugation various approaches are available. Synthesis can be performed where fatty acids are either conjugated to the N-terminus, or to the side-chain of a lysine. Also the cysteine residues in peptides can be modified with fatty acids, giving the corresponding thioester derivatives. The fatty acids that are most commonly used are: caprylic acid (C8), capric acid (C10), lauric acid (C12), myristic acid (C14), palmitic acid (C16) or stearic acid (C18).

PEGylation is the process of covalently attaching polyethylene glycol (PEG) chains to peptides, proteins or other biomolecules. PEGs are polymers that are nonionic, non-toxic, biocompatible and highly hydrophilic. PEGylation of peptides can enhance therapeutic properties due to their increased solubility (for hydrophobic peptides), prolonged half-life through reduced renal clearance, and masked antigenicity for minimum immune response in the host. PEGylated peptides can overcome many of the challenges for peptide drugs such as the peptides disclosed herein by improving the stability and bioavailability of peptides. Regulatory authorities have approved PEGylated drugs of varying PEG chain lengths and with MWs ranging from 5-40 kDa. Since small peptides, such as peptides ranging from 4 to 50 amino acid residues, may have short half-lives in many biological environments, the peptide may be conjugated to a protein or polymer. In particular, polyethylene glycol (PEG) has many known advantages in formulating peptides and proteins pharmaceuticals. Conjugation of peptides and proteins to PEG increases the half-life time of the peptide or protein in a biological system and also minimizes the immune response to the peptide or protein. The peptides of the invention may be conjugated by well-known methods in the art to an appropriate PEG preparation.

Peptidomimetics. The term "peptidomimetics" refers to any chemical compound whose essential elements mimic a natural peptide or protein in three dimensional space. Thus, peptidomimetics of the peptides described by SEQ ID NOS: 1-27 and 30-50 would retain the ability of these peptides to bind to the MERS-CoV S protein and to functionally inhibit attachment, internalization, or release of the MERS-CoV or to allow the host immune system to more effectively recognize the virus.

The method as disclosed herein is typically performed using a peptide, peptide analog, modified peptide, or peptidomimetic as disclosed herein in combination with a pharmaceutically acceptable excipient, carrier, or adjuvant.

The term "active ingredient", as used herein, refers to an ingredient in the composition that is biologically active, for example, the peptides of SEQ ID NOS: 1-27 or 30-50 which bind to MERS-CoV S protein or otherwise interfere with viral infection, as well as to their various forms disclosed herein such as covalently-modified peptides, peptidomimetics, etc. In some embodiments a MERS-CoV-binding peptide may be in the form of a salt, a solvate, or a mixture thereof. This term may also refer to other active, antiviral ingredients incorporated into a composition, such as other antiviral peptides or drugs.

A composition typically contains an amount of MERS-CoV-binding peptide or peptides sufficient to inhibit virus attachment or infection or to reduce the severity of a viral infection. A dosage may be selected by those skilled in the art based on a patient's background, the stage or severity of viral infection, stability and other pharmacokinetics of the peptide, and affinity or avidity of the antiviral peptide for its target on the S protein. In some embodiments, the composition will contain a range from about 0.005, 0.01, 0.02, 0.05, 0.1, 0.2, 0.5, 1.0, 2.0, 5.0, 10, 20, or >20 wt. % of the peptide(s), based on the total weight of the composition. In some embodiments, a dosage of about 25, 50, 75, 100, 200, 300, 400, 500, 600, 700, 800, 900, 1,000, 1,500, 2,000 or >2,000 µg/day of the peptide may be administered once, twice or more than twice per day. In other embodiments, a peptide may be administered as a depot, for example, by intramuscular (e.g., intragluteal), subcutaneous or intradermal injection of 1, 2, 5, 10, 20, or 50 mg. In one embodiment, a pharmaceutical composition comprises the antiviral peptide(s) as disclosed herein at a concentration in the range of 1.0, 2.0, 5.0, 10.0 to >10.0 µM.

Compositions and pharmaceutically acceptable carriers. A composition as disclosed herein will contain at least one peptide that binds to MERS-CoV S protein, to its RBD, or to other segments associated with the virus life cycle or infection of a host cell, such as HR1 and HR2. The peptide may be non-covalently or covalently associated with other components of the composition. A composition comprising a MERS-CoV-binding peptide that is non-covalently associated with other ingredients in the composition may comprise a one or more peptides which bind to MERS-CoV S protein which have been dissolved or suspended in a physiologically acceptable buffer. A composition comprising one or more peptides that are covalently associated with another ingredient or ingredients in the composition could comprise a MERS-CoV-binding peptide covalently bound to a carrier or linker moiety, such as PEG crosslinker or to another MERS-CoV-binding peptide. A composition may contain two, three, four or more different MERS-CoV-binding peptides which bind to or interfere with different portions of the MERS-CoV S protein, for example, one peptide that binds to the RBD on the S1 protein and peptides that bind to or interfere with the function of the HR1 and HR2 regions on the S2 peptide. In some embodiments, two or more peptides may be linked together and spaced apart so as to efficiently bind to different determinants of the S protein such as to the RBD and to HR1 and/or HR2 or so that more than one peptide moiety bind to the same determinant, such as a peptide conjugate comprising two copies of an RBD-binding peptide and having a higher avidity for the RBD of the S protein that individual peptides.

One purpose of a composition is to stabilize the peptide during storage, facilitate safe and effective administration of the peptides that bind to MERS-CoV S protein or its RBD to a patient, to enhance stability, targeting, or other pharmacokinetic properties of these peptides after administration to a patient, and/or improve the pharmacodynamics properties of the peptide by maintaining it in a configuration that efficiently binds to or associated with the MERS-CoV S protein. Typically, a composition is formulated to be in a non-toxic and physiologically acceptable form and in a form that permits a MERS-CoV-binding peptide to efficient bind to MERS-CoV S protein or exhibit other antiviral properties. A composition is usually formulated with the route of their administration in mind, for example, it may be formulated for administration to, or targeting to a tissue for which MERS-CoV is trophic, such as respiratory system tissues. In many embodiments, a pharmaceutically acceptable carrier is selected from those conventionally used to administer peptides, drugs or vaccines in vivo. Such formulations are described by and incorporated by reference to *Remington: The Science and Practice of Pharmacy*, The University of the Sciences in Philadelphia, Editor, Lippincott, Williams, & Wilkins, Philadelphia, Pa., 21st Edition (2005).

Examples of physiologically acceptable carriers include antioxidants including ascorbic acid; low molecular weight (less than about 10 residues) peptides; proteins, such as serum albumin, gelatine, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrin; chelating agents such as EDTA; sugar alcohols such as mannitol or sorbitol; salt-forming counter ions such as sodium; and/or non-ionic surfactants such as TWEEN® (ICI, Inc.; Bridgewater, N.J.), polyethylene glycol (PEG), and PLURONICS™ (BASF; Florham Park, N.J.). An "excipient" refers to an inert substance added to a composition to further facilitate administration of a compound. Examples, without limitation, of excipients include calcium carbonate, calcium phosphate, various sugars and types of starch, cellulose derivatives, gelatine, vegetable oils, and polyethylene glycols. In some embodiments, the pharmaceutical composition comprises one or more carriers and/or excipients selected from the group consisting of a buffer, an inorganic salt, a fatty acid, a vegetable oil, a synthetic fatty ester, a surfactant, a sugar, a polymer, and combination thereof. In some embodiments, the pharmaceutical composition may further comprise pharmaceutically acceptable binders, such as sucrose, lactose, glucose, fructose, galactose, mannitol, xylitol, and pharmaceutically acceptable excipients such as calcium carbonate and calcium phosphate.

In some embodiments, the pharmaceutically acceptable carrier and/or excipient is at least one selected from the group consisting of a buffer, an inorganic salt, a fatty acid, a vegetable oil, a synthetic fatty ester, a surfactant, and a polymer.

Exemplary buffers include, without limitation, phosphate buffers, citrate buffer, acetate buffers, borate buffers, carbonate/bicarbonate buffers, and buffers with other organic acids and salts.

Exemplary inorganic salts include, without limitation, calcium carbonate, calcium phosphate, disodium hydrogen phosphate, potassium hydrogen phosphate, sodium chloride, zinc oxide, zinc sulfate, and magnesium trisilicate.

Exemplary fatty acids include, without limitation, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, without limitation, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), $C_{12}$-$C_{16}$ fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to a monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide.

Surfactants may act as detergents, wetting agents, emulsifiers, foaming agents, and dispersants. Surfactants that may be present in the compositions of the present disclosure include zwitterionic (amphoteric) surfactants, e.g., phosphatidylcholine, and 34(3-cholamidopropyl)-dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltrimethyl-ammonium bromide, tetradecyltrimethylammonium bromide, tetradecyltrimethylammonium chloride, and dodecylammonium chloride, and combinations thereof.

Exemplary polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphos-phazenes, polyhydroxybutyrates, polyhydroxyvalerates, polyalkylene oxalates, polyalkylene succinates, poly(malic acid), poly(maleic anhydride), a polyvinyl alcohols, and copolymers, terpolymers, or combinations or mixtures therein. The copolymer/terpolymer may be a random copolymer/terpolymer, or a block copolymer/terpolymer.

Depending on the route of administration e.g. oral, parental, or topical, the composition may be in the form of solid dosage form such as tablets, caplets, capsules, powders, and granules, semi-solid dosage form such as ointments, creams, lotions, gels, pastes, and suppositories, liquid dosage forms such as solutions, and dispersions, inhalation dosage form such as aerosols, and spray, or transdermal dosage form such as patches.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatine, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavouring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids, such as oleic acid, find use in the preparation of injectable. Dimethylacetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug.

Topical administration may involve the use of transdermal administration such as transdermal patches or iontophoresis devices. Formulation of drugs is discussed in, for example, Hoover, J. E. Remington's pharmaceutical sciences, Mack Publishing Co., Easton, Pa., 1975; and Liberman, H. A.; Lachman, L., Eds. Pharmaceutical dosage forms, Marcel Decker, New York, N.Y., 1980, which are incorporated herein by reference in their entirety.

In other embodiments, the composition comprising the antiviral peptides disclosed herein has different release rates categorized as immediate release and controlled- or sustained-release.

As used herein, immediate release refers to the release of an active ingredient substantially immediately upon administration. In another embodiment, immediate release occurs when there is dissolution of an active ingredient within 1-20 minutes after administration. Dissolution can be of all or less than all (e.g. about 70%, about 75%, about 80%, about 85%, about 90%, about 91%, about 92%, about 93%, about 94%, about 95%, about 96%, about 97%, about 98%, about 99%, about 99.5%, 99.9%, or 99.99%) of the active ingredient. In another embodiment, immediate release results in complete or less than complete dissolution within about 1 hour following administration. Dissolution can be in a subject's stomach and/or intestine. In one embodiment, immediate release results in dissolution of an active ingredient within 1-20 minutes after entering the stomach. For example, dissolution of 100% of an active ingredient can occur in the prescribed time. In another embodiment, immediate release results in complete or less than complete dissolution within about one hour following rectal administration. In some embodiments, immediate release is through inhalation, such that dissolution occurs in a subject's lungs.

Controlled-release, or sustained-release, refers to a release of an active ingredient from a composition or dosage form in which the active ingredient is released over an extended period of time. In one embodiment, controlled-release results in dissolution of an active ingredient within 20-180 minutes after entering the stomach. In another embodiment, controlled-release occurs when there is dissolution of an active ingredient within 20-180 minutes after being swallowed. In another embodiment, controlled-release occurs when there is dissolution of an active ingredient within 20-180 minutes after entering the intestine. In another embodiment, controlled-release results in substantially complete dissolution after at least 1 hour following administration. In another embodiment, controlled-release results in substantially complete dissolution after at least one hour following oral administration. In another embodiment, controlled-release results in substantially complete dissolution after at least one hour following rectal administration. In one embodiment, the composition is not a controlled-release composition.

Topical compositions. A peptide or modified peptide or petidomimetic as disclosed herein may be incorporated into a composition for topical or external use, for example, into a hand sanitizer in an amount that inhibits transmission or infectivity of MERS-CoV virus to which a subject is externally exposed. One or more peptides as disclosed herein may be formulated as is known in the art for direct application to a target area, for example nails and skin. Forms chiefly conditioned for topical application take the form, for example, of lacquers, creams, milks, gels, powders, dispersion or microemulsions, lotions thickened to a greater or lesser extent, impregnated pads, ointments or sticks, aerosol formulations (e.g. sprays or foams), soaps, detergents, lotions or cakes of soap. Other conventional forms for this purpose include ointments, creams, lotions and polymer coverings.

A peptide may be covalently or non-covalently associated with a porous or particulate substrate so that MERS-CoV S protein can bind to it. The substrate may be a mask, nasal plug, bandage, wound dressing, air filter, diaper, gloves, hat, hood, surgical gown or other clothing. In some embodiments, the peptide will be embedded in a material, such as a resin or fabric, in others it will be sprayed, soaked into, coated, or otherwise associated with a porous material, such as an exposed surface of the material.

Pharmaceutical compositions as contemplated herein may be manufactured by processes well-known in the art, e.g., by means of conventional mixing, dissolving, granulating, dragee-making, levigating, emulsifying, encapsulating, entrapping or lyophilizing processes. Depending on the intended mode of administration (oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage.

Physical forms. In some embodiments the peptide as disclosed herein is in the form of a particle having an average diameter ranging from 0.1, 0.2, 0.5, 1, 2, 3, 4 to 5 µm. In other embodiments, the peptide will be in a form of a particle having particle having an average diameter of >5, 6, 7, 8, 9 to 10 µm or any intermediate subrange or value. An average particle size may be selected to facilitate deposition of a particle in a particular part of the respiratory system or to control its pharmacokinetic properties including rate of dissolution. In one embodiment, the peptide is in the form of a liposome that has an average diameter ranging from 0.1, 0.2, 0.5, 1, 2, 3, 4 to 5 µm or any intermediate subrange or value.

In another embodiment peptide as disclosed herein is in the form of a powder comprising at least one solid excipient and the peptide and which has an average diameter ranging from 0.1, 0.2, 0.3, 0.4, 0.5, 1, 2, 3, 4, to 5 µm or any intermediate subrange or value.

Peptide Synthesis: The peptides disclosed herein which bind to MERS-CoV S protein or its RBD may be obtained by well-known biological and chemical synthetic methods. Peptides comprising up to 4, 5, 6, 7, 8, 9, 10, 11, 12, 13, 14, 15, 20, 25, 30, 35, 40 or 50 amino acid residues may be prepared by chemical synthesis. One advantage of chemical synthesis is that any chemical compound having an amino group and a carboxyl group may be incorporated into any peptide. The chemical methods for peptide synthesis are well-known in the art and taught in many standard text books such as Creighton, T. E., Proteins; Structures and molecular properties, second edition (1993) W. H. Freeman and Company, incorporated herein by reference. The peptide may be synthesized in solution or on solid support. Solution methods may be used to prepare short peptides (less than 5-6 amino acid residue) by coupling two appropriately protected amino acids, one of which having a free amino group and the other having free carboxyl group using a coupling reagent including but not limited to dicyclohexylcarbodiimide (DCC) in any suitable solvent such as methylene chloride to produce a dipeptide with protected carboxyl and amino termini. One of the termini is selectively unprotected and the resulting peptide is coupled to another amino acid and the process is repeated until the desired sequence is made. Once the peptide is made, all the protecting group can be removed by well-known methods in the art such as acid treatment, catalytic hydrogenation, and mild base hydrolysis. In the 1960's, Bruce Merrifield developed the method of solid support synthesis of peptides which became the method of choice of making peptides of up to 60 amino acid in length and even longer. This method and its application are described in details in the prior art, see Merrifield, B. Solid phase synthesis Science (1986) 232, 241-247, incorporated herein by reference in its entirety, and Sheppard, R. C. Modern Methods of solid phase peptide synthesis, Science Tools (1986) 33, 9-16, incorporated herein by reference in its entirety. The method utilizes polymeric resins functionalized with amino groups or hydroxyl groups to which a properly protected amino acid is attached followed by deprotecting an amino or carboxyl group. The resulting amino or carboxyl group can be coupled to another amino acid residue using a coupling reagent such as DCC. The process is fully automated and can produce peptides efficiently especially in the range 4 to 60 amino acid residues in large quantities. Once the peptide is assembled on the solid phase, the peptide is liberated from the solid phase by hydrogen fluoride treatment to produce the peptide without any protecting groups.

All natural amino acid properly protected and other reagents for use in automated peptide synthesis systems are commercially available. The structure of the resulting peptide can be verified by amino acid composition analysis and spectroscopic methods such as NMR spectroscopy and mass spectrometry.

A peptide targeting MERS-CoV S protein or its RBD may be obtained by biological methods in a host cell or cell free system. Such biological methods are well-known to one of ordinary skill in the art. For example, DNA encoding the peptide or a longer protein containing the peptide may be inserted into an expression vector which is expressed by a host cell to produce the protein or peptide of interest. In cases, where the peptide sequence of interest is expressed as part of a longer protein, the protein may be designed to be cleaved with a protease, thus liberating the peptide of interest. Details of peptide and protein expression in host cell are fully described in Sambrook et al. Molecular Cloning: a laboratory manual (1989) Second Edition, Cold Spring Harbor Laboratory, Cold Spring Harbor, N.Y., incorporated herein by reference in its entity.

Once the peptides of the invention are synthesized or otherwise obtained, purified as necessary or desired, they can be preferably lyophilized and/or stabilized. Prior to administration the concentration of a peptide can then be adjusted to a suitable concentration based on route of administration, other pharmacokinetic factors, and patient status.

Method of Identifying Antiviral Compounds. Another aspect of the invention is directed a method of designing, identifying, selecting, and optimizing an antimicrobial and antiviral peptide selected from the group consisting of SEQ ID NO: 1-27 or 30-50 to obtain a chemical compound having increased antiviral activity relative to the parent peptide. In some embodiments the method comprises (a) retrieving a three dimensional structure of the MERS-CoV receptor binding domain of spike protein in silico using the PDB atomic coordinates of accession number 4KQZ or 4NJL; in one embodiment, chain A and B or PDB 4KQZ is used; (b) selecting a peptide from SEQ ID NO: 1-27 or 30-50 to the binding site of the model; (c) modifying the structure of the peptide sequence to enhance and optimize the interactions between the peptide and the receptor binding domain of spike protein; (d) synthesizing a peptide or compound using the modified structure of (c); and (d) measuring the binding of the peptide or compound to MERS-CoV receptor binding domain of spike protein.

The three dimensional structure of MERS-CoV receptor binding domain (RBD) is described by PDG entry 4KQZ, which is incorporated by reference; which is also described and incorporated by reference to Lu et al., Molecular basis of binding between novel human coronavirus MERS-CoV and its receptor CD26 (2013) Nature 500: 227-231, which reports the three dimensional structure of MERS-CoV receptor binding domain in the 51 subunit of the spike protein (SEQ ID NO: 29) as determined by the X-ray diffraction method at high resolution. 4KQZ is receptor binding domain in S1 subunit and consist of 240 amino acid residues. The receptor binding motif is V484-L567 of RBD.

The three dimensional structure of the MERS-CoV S2 fusion protein core is described by PDB 4NJL, which is incorporated by reference. The S2 subunit comprises of the two regions HR1 and HR2 which correspond to the residues E992 to L1040 for HR1 and the residues 11246 to L1286 for HR2 of the sequence of the MERS CoV Spike protein (SEQ ID NO: 28).

The peptides of SEQ ID NOS: 1-27 interact with the 4KQZ structure.

SEQ ID NO: 28 describes the MERS Co-V Spike protein sequence given by UniProtKB K0BRG7.

SEQ ID NO: 29 describes the sequence for PDB 4KQZ chain A.

The peptides of SEQ ID NOS: 30, 32, 34, 35, 36, 37, and 39 are inhibitors for spike protein receptors described by PDB 4NJL.

A model of three-dimension structure of the binding domain can be constructed in silico using the atomic coordinates by well-known methods in the art and described herein below. The binding pocket of the protein was predicted using SiteMap; Halgren, T., *New method for fast and accurate binding-site identification and analysis, Chem. Biol. Drug Des.*, 2007, 69, 146-148]. SiteMap determines primary binding site on a receptor by calculating the sites on protein surface by searching the grid points called site points. Then the contour site maps are generated, producing hydrophobic and hydrophilic map. The experimentally validated binding pocket for receptor binding domain (RBD) is from Val-484 to Leu567 of SEQ ID NO: 28; Wang N, Shi X, Jiang L, et al. *Structure of MERS-CoV spike receptor-binding domain complexed with human receptor DPP4. Cell Research.* 2013; 23(8):986-993. In one embodiment, the binding pocket of the spike protein comprises two or more amino acid residues of Asn-519, Ala-520, Gln-522, Glu-536, Asp-537, Gly-538, Tyr-540, and Arg-542 of SEQ ID NO: 28.

The method as disclosed herein may involve modifying one of the peptides of SEQ ID NO: 1-27 or 30-50 to produce a chemical compound or a peptide with improved binding characteristics. As used herein, the words "design" or "designing" is meant to provide a novel molecular structure of, for example, a compound, such as a small molecule or a substrate analogue of the peptides of SEQ ID NO: 1-27 or 30-50. The resulting molecule may be any chemical entity that binds to the binding site such as but not limited to linear peptides, cyclic peptides, macrolactons, and macrolactams. Suitable computer programs which may be used in the design and identification of potential binding compounds (e.g., by selecting suitable chemical fragments) include, but are not limited to, GRID; Goodford 1985 J. Med. Chem. 28:849 857, MCSS; Miranker, A. and M. Karplus, (1991) *Proteins: Structure. Function and Genetics,* 11:29-34, AUTODOCK, Goodsell, D. S et al (1990) *Proteins: Structure. Function, and Genetics* 8:195 202; and DOCK; Kuntz, I. D. et al. (1982) J Mol. Biol 161:269-288; and Bartlett, (1989) *Molecular Recognition in Chemical and Biological Problems,* Special Pub., Royal Chem. Soc. 78:182-196.

Suitable computer programs which may be used in connecting the individual chemical entities or fragments include, but are not limited to, CAVEAT, Bartlett, (1989) Molecular *Recognition in Chemical and Biological Problems,* Special Pub., Royal Chem. Soc. 78:182-19632); and 3D Database systems such as MACCS-3D by MDL Information Systems, San Leandro, Calif.), HOOK (Molecular Simulations, Burlington, Mass.) and as reviewed by Martin, Y. C, (1992) J Med. Chem, 35:2145 2154. Other suitable computer programs which may be used to modify the peptides of the invention include, but not limited to, LUDI, Bohrn, (1992) J. Comp. Aid Molec. Design 6:61-78, LEGEND, Nishibata et al. (1991) Tetrahedron 47:8985; and LEAPFROG, Tripos Associates, St. Louis, Mo. Also, other molecular modeling techniques may be employed in accordance with this invention, Cohen, N. C. et al. (1990) J Med. Chem. 33: 883-894 incorporated herein by reference in its entirety; and Navia (1992) Current Opinions in Structural Biology 2:202-210 incorporated herein by reference in its entirety.

A potential binding compound has been designed, selected, identified, synthesized, or chosen by the methods described herein, the affinity with which that compound binds to the receptor binding site may be tested and optimized by computational evaluation. A compound designed, or selected, or synthesized, or chosen as potential binding compound or may be further computationally optimized so that in its bound state it would preferably lack repulsive electrostatic interaction with the target site. Such non-complementary (e.g., electrostatic) interactions include repulsive charge-charge, dipole-dipole and charge-dipole interactions. Specifically, the sum of all electrostatic interactions between the potential binding compound and the binding site is neutral or make favorable contribution to the enthalpy of binding. Suitable computer software which may be used to evaluate compound deformation energy and electrostatic interactions, includes, but is not limited to, Gaussian 92, revision C, M. J. Frisch, Gaussian, Inc., (1992) Pittsburgh, Pa.; AMBER, version 4.0, P. A. Kollman, (1994) University of California at San Francisco; QUANTA/CHARMM, Molecular Simulations, Inc., (1994) Burlington, Mass].; and Insight II/Discover, Biosysm Technologies Inc., (1994) San Diego, Calif.

These programs may be implemented, for example, using a Silicon Graphics workstation, IRIS 4D/35 or IBM RISC/6000 workstation model 550. Hardware systems, such as an IBM thinkpad with LINUX operating system or DELL latitude D630 with WINDOWS operating system, may be used. Other hardware systems and software packages will be known to those skilled in the art of which the speed and capacity are continually modified.

As used herein, a "binding compound" refers to a compound which reversibly or irreversibly binds to MERS-CoV receptor binding domain in the 51 subunit of spike (spike binding pocket). In certain embodiments, the binding compound binds in the spike binding pocket. Binding may involve the formation of bonds which may be covalent or non-covalent. Non-covalent bonds may be e.g. hydrogen bonds, ionic bonds or hydrophobic interactions. A binding compound is expected to interfere and inhibit the interaction of between the spike protein and its target cellular receptor DPP4.

A binding compound may be a small molecule. The term "small molecule" as used herein is meant to describe a low molecular weight organic compound which is not a polymer. A small molecule may bind with high or low affinity to a biopolymer such as protein, nucleic acid, or polysaccharide and may in addition alter the activity or function of the biopolymer. The molecular weight of the small organic compound may generally be smaller than about 1500 Da. Small molecules may be smaller than about 1000 Da, smaller than about 800 Da, or smaller than about 500 Da. Small molecules may rapidly diffuse across cell membranes and may have oral bioavailability. These compounds can be natural or synthetic.

It is useful to be able to identify binding molecules that are specific to the spike binding pocket. By specific it is meant that the binding molecule has a preference for binding to the spike binding pocket and does not bind to one or more other biomolecules or shows at least 5, 10, 20, 50, 100, 200, 500, or 1,000 fold reduced affinity to one or more other biomolecules. Binding can be quantitated in accordance with methods well-known in the art and described herein below.

Furthermore, in certain embodiments, the above method further comprises the steps of using a suitable assay, as described herein, to characterize the potential binding compound's ability to bind to spike binding pocket. This may involve directly testing the compound's ability to bind, and/or determining whether the compound has an influence on the binding of the spike protein to its cellular receptor DPP4. To evaluate binding properties of binding compounds, assays may be used. Several assay methods are well-known in the art. The methods include, but not limited to, calorimetric techniques, surface plasmon resonance (SPR, Biacore™), and spectroscopic methods including NMR methods, fluorescence methods and UV-Vis methods.

Calorimetric methods include but not limited to isothermal titration calorimetry and differential scanning calorimetry. SPR is the resonant oscillation of conduction electrons at the interface between negative and positive permittivity material stimulated by incident light. The method involves immobilizing one molecule of a binding pair on the sensor chip surface ("ligand", in Biacore parlance) and injecting a series of concentrations of its partner ("analyte") across the surface. Changes in the index of refraction at the surface where the binding interaction occurs are detected by the hardware and recorded as RU (resonance units) in the control software. Curves are generated from the RU trace and are evaluated by fitting algorithms which compare the raw data to well-defined binding models. These fits allow determination of a variety of thermodynamic constants, including the apparent affinity of the binding interaction. SPR main advantage is that it does not require labeling the protein or the binding compound.

Spectroscopic such as NMR methods and optical spectroscopic methods such as fluorescence, UV-Vis, and Circular Dichroism are well-known method utilized in measuring the interaction between a binding compound and a protein. In the instant case, fluorescence methods are convenient because the binding domain of the spike binding protein comprises two tryptophan residues, i.e., Trp-535 and Trp-553. The binding of a compound to the binding domain should accompanied by fluorescent change in intrinsic protein fluorescence. The fluorescence method is suitable for high throughput screening method amenable to automation in a laboratory environment. Another fluorescence assay method is a competitive displacement assay method. Each of the peptides of SEQ ID NO: 4, 9, 13, 21, and 25 contains a tryptophan residue. The displacement of one of the tryptophan containing peptide by a binding compound from the binding site would be accompanied by change in fluorescence.

The method can involve saturating the spike binding protein with one of the peptides of SEQ ID NO: 4, 9, 13, 21, or 25 and observing the tryptophan fluorescence of the peptide. Adding the compound of interest to spike binding protein/peptide complex and observe the change in fluorescence as a function of the concentration of the protein of interest.

NMR methods may be use to observe the binding of a binding compound and valuable structural information may be obtained in addition to the binding constant. In its simple form, the observation of broadening of an NMR signal as a function of concentration would allow the determination of binding constants. Some other NMR methods may require isotopically labeled binding compounds and/or proteins. Isotopically labelling proteins and binding compounds with $^2H$, $^{13}C$, and $^{15}N$ are well-known in the art, and $^2H$, $^{13}C$, and $^{15}N$ amino acid suitable for peptide synthesis are commercially available.

Sequence Identity/Similarity. While the peptide sequences described by SEQ ID NOS: 1-27 are relatively short, BLASTP can be used to identify amino acid sequences having at least 80%, 85%, 87.5%, 90%, 92.5%, 95%, 97.5%, 98%, 99% sequence identity or similarity to a reference amino acid using a similarity matrix such as BLOSUM45, BLOSUM62 or BLOSUM80 where BLOSUM45 can be used for closely related sequences, BLOSUM62 for mid-range sequences, and BLOSUM80 for more distantly related sequences. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity or similarity to the amino acid sequences disclosed herein are contemplated and encompassed by this disclosure. A representative BLASTP setting that uses an Expect Threshold of 10, a Word Size of 3, BLOSUM 62 as a matrix, and Gap Penalty of 11 (Existence) and 1 (Extension) and a conditional compositional score matrix adjustment. Default settings for BLASTP are described by and incorporated by reference to Blast.cgi?PROGRAM=blastp&PAGE TYPE=BlastSearch& LINK LOC=blasthome (last accessed Mar. 5, 2020).

Example 1

The MERS-CoV receptor-binding domain (RBD) that comprises residues 367-606 of SEQ ID NO: 28, is incorporated by reference to, Lu et al. (2013) Nature 500: 227-231 and Yu et al., Scientific Reports (2015/8/18) 5, 13133.

The protein was expressed in the insect host cells Spodopterafrugipedra Sf9 using a Bac-to-Bac baculovirus expression system.

Sf9 insect cells were maintained in Insect-Xpress-free medium (Lonza) without serum at 27° C.

A cDNA encoding the MERS-CoV RBD was cloned into pFastBoc-Dual vector with an N-terminal gp67 signal peptide to facilitate secretion and C-terminal His-Tag to facilitate purification. The plasmid was transformed into bacterial DH10Bac competent cells, and the extracted bacmid was transfected into Sf9 cells in the presence of Cellfectin II reagent (Invitrogen).

After incubation of the transfected cells at 27° C. for 7 days, the low-titer baculoviruses were harvested by collecting the cell-culture supernatant with centrifugation at 2,000 rpm for 10 minutes.

After two rounds of amplification, the high-titer viruses were used to infect Sf9 cells at a density of $2\times10^6$ cells per milliliter. The cell-culture supernatant containing the MERS-CoV RBD was harvested 60 hours after infection, concentrated, and buffer-exchanged to HBS buffer (10 mM Hepes, pH 7.2, and 150 mM NaCl).

The MERS-CoV RBD was then captured with nickel beads, eluted with 500 mM imidazole in HBS buffer, and purified by gel-filtration chromatography using a Superdex-200 High Performance column (GE Healthcare) with the HBS running buffer.

The purified MERS-CoV RBD was used without any further steps for binding studies.

Alternatively, the protein is treated with endoglycosidase F1 and F3 at room temperature overnight to remove glycosylic groups from the protein followed by further purification using gel-filtration chromatography.

Example 2

In Vitro Binding Assays

Fluorescence binding assay. The binding of the peptides to the receptor binding document or RBD was measured using the change of the intrinsic protein fluorescent upon binding the peptide. A plot of the change of fluorescence vs the peptide concentration produces a sigmoidal curve from which $K_b$ can be calculated.

Surface plasmon resonance binding assay. Real-time binding and analysis by surface plasmon resonance (SPR) was conducted on a BIAcore T200 instrument (GE Healthcare) at 25° C. as described by, and incorporated by reference to, Yu et al., Scientific Reports (2015/8/18) 5, 13133.

A peptide was immobilized on a research-grade CMS sensor chip by the amine-coupling method. A flow cell 1 was left blank as a reference. A peptide (10 µg/mL) in 10 mM sodium acetate pH 5.5 can be immobilized to 400 response units on the flow cell 2.

For the collection of data, MERS-CoV RBD was injected in a buffer of 10 mM Hepes, pH 7.2, 150 mM NaCl, and 0.005% (vol/vol) Tween-20 over the flow cells at various concentrations with a 30 µL/min flow rate. The MERS-CoV RBD and the peptide complex was allowed to associate for 60 seconds and dissociate for 90 seconds. Data were analyzed with the BIAcore T200 evaluation software by fitting to a 1:1 Langmuir binding model.

Example 3

In silico binding of the peptide to RBD. The crystal structure of MERS-CoV receptor binding domain (RBD) subunit of spike protein, PDB accession number 4KQZ, was downloaded from the Protein Data Bank (PDB); Berman et al. The Protein Data Bank. Nucleic Acids Research 2000; 28(1):235-42. The receptor binding domain or RBD in the 51 subunit consists of 240 amino acid residues and the receptor binding motif spans residues V484-L567 of the RBD.

The protein structure was preprocessed using the Protein Preparation Wizard in Maestro (Schrondinger LLC, New York, N.Y., 2017). The steps involved in protein preparation included: (a) preprocessing the protein structure and removing nonessential water molecules and ions (b) deleting unwanted chains and waters and fixing or removing of het groups in the structure, and (c) optimizing and minimizing the energy of the structure during refinement process.

The amino acid sequences of a set of antimicrobial peptides were downloaded from the antimicrobial peptide database (APD), version 3, which is incorporated by reference to Wang et al. *APD3: the antimicrobial peptide database as a tool for research and education*. Nucleic Acids Research 2016; 44(D1):D1087-D93.

A list of small antimicrobial peptides of less than or equal to 12 amino acid residues in length were selected as smaller sequences are easier and cheaper to synthesize than longer peptides. Peptides were also selected based on non-toxicity to mammalian cells.

The active site of RBD (4KQZ) protein was predicted using SiteMap which is incorporated by reference Halgren, T., *New method for fast and accurate binding-site identification and analysis*, Chem. Biol. Drug Des., 2007, 69, 146-148].

SiteMap searches grid points called site points on a protein surface to calculate binding sites thus determining a primary binding site on a receptor. Then contour site maps are generated, producing hydrophobic and hydrophilic maps.

Peptides were docked with optimized MERS-CoV 4KQZ at the active site through the generated grid by Glide peptide docking module in Schrodinger suite. The parameter settings include: centroid docking of selected residues, generation of conformers from sequence using cis-amide bonds and the number of poses to return for each docking run was set to 3. Docked poses of antimicrobial peptides were additionally analyzed using docking score approach Most of the active site residues of RBD made good contacts with selected antimicrobial peptides. As used herein the phrase "aromatic hydrogen bond" means that an aromatic C—H bond acts as hydrogen bond donor to a hydrogen bond acceptor atom such as an oxygen or nitrogen atom. The result of docking the antimicrobial peptides to the binding site is summarized in Table 1 below.

TABLE 1

The list of putative antimicrobial peptides showing the number of hydrogen bonds, salt bridge interactions and aromatic hydrophobic interactions.

| Peptide name | APD ID | SEQ ID NO: | Docking score (Kcal/mol) | H-bonds | Salt Bridge | Aromatic Hydrogen Bond |
|---|---|---|---|---|---|---|
| RYPAVGYT | AP02727 | 1 | -11.736 | 7 | 1 | 3 |
| RYPAVGYN | Synthetic | 2 | -11.291 | 13 | 0 | 1 |
| RYPAQGYT | Synthetic | 3 | -9.691 | 12 | 1 | 2 |
| RYPAWGYT | Synthetic | 4 | -10.138 | 12 | 1 | 2 |
| RYPAKGYT | Synthetic | 5 | -10.044 | 11 | 1 | 3 |
| RRPAVGYDT | Synthetic | 6 | -7.46 | 10 | 2 | 2 |
| RYPAVGYTK | Synthetic | 7 | -8.219 | 9 | 2 | 3 |
| RYPRVGYT | Synthetic | 8 | -9.068 | 7 | 2 | 2 |
| NAGSLLSGWG | AP02345 | 9 | -10.782 | 10 | 0 | 1 |
| PFKLSLHL | AP01210 | 10 | -10.599 | 7 | 1 | 2 |
| RLGDGCTR | AP02340 | 11 | -10.224 | 7 | 3 | 0 |
| ATQSHQ | AP02441 | 12 | -10.08 | 10 | 0 | 1 |
| DEKGPKWKR | AP01301 | 13 | -9.726 | 10 | 2 | 1 |
| TCSYTMEA | AP01344 | 14 | -9.541 | 10 | 0 | 1 |
| QGGQANQ | AP02696 | 15 | -9.488 | 12 | 0 | 0 |
| FFFLSRIF | AP01534 | 16 | -9.466 | 8 | 1 | 4 |
| DDDDDDD | AP00528 | 17 | -9.46 | 10 | 4 | 0 |
| GSEIQPR | AP00995 | 18 | -9.279 | 10 | 0 | 0 |
| KTCENLADTY | AP00553 | 19 | -9.189 | 8 | 1 | 1 |
| GADDDDD | AP02885 | 20 | -9.106 | 7 | 2 | 1 |
| AWKLFDDGV | AP01805 | 21 | -8.903 | 8 | 2 | 3 |
| AAGMGFFGAR | AP01481 | 22 | -8.504 | 8 | 1 | 2 |
| SMSGFSKPHD | AP02768 | 23 | -8.43 | 7 | 1 | 1 |
| RGSALTHLP | AP02691 | 24 | -8.306 | 11 | 1 | 0 |
| NRWCFAGDD | AP02194 | 25 | -8.115 | 5 | 2 | 1 |

TABLE 1 -continued

The list of putative antimicrobial peptides showing the number of hydrogen bonds, salt bridge interactions and aromatic hydrophobic interactions.

| Peptide name | APD ID | SEQ ID NO: | Docking score (Kcal/mol) | H-bonds | Salt Bridge | Aromatic Hydrogen Bond |
|---|---|---|---|---|---|---|
| DEDDD | AP02670 | 26 | −8.022 | 5 | 4 | 0 |
| KIAKVALKAL | AP01814 | 27 | −6.173 | 6 | 3 | 1 |

Other peptides described in U.S. Provisional 62/823,912, filed Mar. 26, 2019 are incorporated by reference. Other peptides (or peptidomimetics) which may be used as disclosed herein, are those that have one or two insertions, substitutions or deletions of residues in any of the peptides described by SEQ ID NOS: 1-27 or 30-50 or are covalently modified versions thereof as described herein, and which have a docking score with the S1 subunit ranging from at least about −6, −7, −8, −9, −10, −11, −12 or <−12; forms from 4, 5, 6, 7, 8, 9, 10, 11, 12, 13, or >13 salt bridges with the S1 subunit; forms from 0, 1, 2, 3, 4 or >4 salt-bridges with the S1 subunit; and/or which forms from 0, 1, 2, 3, 4 or >4 aromatic hydrogen bonds with the S1 subunit.

Table 2 below shows the atomic interactions of each peptide which contains the best functional groups such as —OH, —NH and —NH$_2$ for candidate agents.

TABLE 2

Interactions between 4KQZ receptor binding domain and residues of the top peptides of SEQ ID NOS: 1-27.

| | Interactions between RBD of S Protein and various peptides | | |
|---|---|---|---|
| Peptide | Hydrogen bonds | Hydrophobic residues | Salt bridge interactions |
| RYPAVGYT SEQ ID NO: 1 | Thr-424 [OH]<br>Gln-427: [NH]<br>Phe-473: [NH]<br>Glu-536: [NH, NH2]<br>Asp-537: [NH]<br>Gln-471: [NH] | Phe-473 | Glu-536 |
| RYPAVGYN SEQ ID NO: 2 | Thr-424: [O]<br>Gln-427: [NH]<br>Leu-456: [NH2]<br>Ser-465: [NH2]<br>Tyr-469: [NH2]<br>Gln-471: [OH]<br>Phe-473: [NH, NH]<br>Ala-520: [NH2]<br>Glu-536: [NH, NH2]<br>Arg-542: [O, O] | Ala-520<br>Leu-456<br>Tyr-469<br>Phe-473 | None |
| RYPAQGYT SEQ ID NO: 3 | Asp-422: [NH]<br>Phe-423: [OH, OH]<br>Tyr-469: [OH]<br>Gln-471: [OH, OH]<br>Asp-510: [NH2]<br>Glu-513: [NH2]<br>Arg-542: [O, O, O, O] | Phe-423<br>Tyr-469 | Asp-510 |
| RYPAWGYT SEQ ID NO: 4 | Gln-427: [NH]<br>Lys-453: [OH]<br>Leu-456: [NH]<br>Tyr-469: [OH]<br>Phe-473: [NH]<br>Gly-538: [OH]<br>Asp-537: [NH2]<br>Tyr-540: [NH]<br>Arg-542: [O, O, O] | Phe-473<br>Leu-456<br>Tyr-540<br>Tyr-469 | Asp-537 |
| RYPAKGYT SEQ ID NO: 5 | Ser-426: [NH2]<br>Gln-427: [NH2]<br>Lys-453: [O]<br>Tyr-469: [OH]<br>Gln-471: [OH]<br>Glu-513: [NH, OH]<br>Asp-537: [NH2, NH2]<br>Tyr-540: [O]<br>Arg-542: [OH] | Tyr-540<br>Tyr-469 | Asp-537 |

TABLE 2 -continued

Interactions between 4KQZ receptor binding domain and residues of the top peptides of SEQ ID NOS: 1-27.

| Peptide | Interactions between RBD of S Protein and various peptides | | |
|---|---|---|---|
| | Hydrogen bonds | Hydrophobic residues | Salt bridge interactions |
| RRPAVGYDT<br>SEQ ID NO: 6 | Lys-453: [O]<br>Gln-471: [O, OH]<br>Phe-473: [NH2]<br>Asn-475: [NH2, NH2]<br>Lys-502: [O]<br>Asp-537: [NH2, NH2]<br>Tyr-540: [NH] | Tyr-540<br>Phe-473 | Asp-537<br>Lys-453 |
| RYPAVGYTK<br>SEQ ID NO: 7 | Glu-513: [OH]<br>Asp-422: [NH2]<br>Arg-542: [O, O]<br>Cys-425: [OH]<br>Gln-427: [NH]<br>Lys-453: [O]<br>Gln-471: [OH]<br>Asp-510: [NH] | Cys-425<br>Asp-510 | Asp-422 |
| RYPRVGYT<br>SEQ ID NO: 8 | Asp-510: [NH2]<br>Arg-511: [OH]<br>Glu-513: [NH2, NH]<br>Ser-457: [OH]<br>Arg-542: [O, O] | None | Asp-510<br>Glu-513 |
| NAGSLLSGWG<br>SEQ ID NO: 9 | Asn-421: [NH2]<br>Asp-422: [NH, NH2]<br>Cys-425: [NH]<br>Ser-426: [NH]<br>Gln-427: [O]<br>Ser-457: [O]<br>Lys-453: [O]<br>Arg-542: [O]<br>Gly-538: [OH] | Cys-425 | None |
| PFKLSLHL<br>SEQ ID NO: 10 | Gln-427: [NH]<br>Leu-456: [NH]<br>Gln-471: [NH]<br>Phe-473: [NH]<br>Asp-537: [NH2]<br>Tyr-540: [O]<br>Arg-542: [O] | Tyr-540<br>Phe-473<br>Leu-456 | Asp-537 |
| RLGDGCTR<br>SEQ ID NO: 11 | Thr-424: [OH]<br>Ser-459: [O]<br>Gln-471: [O]<br>Phe-473: [NH]<br>Glu-513: [NH2, NH2]<br>Asp-537: [NH2, NH]<br>Arg-542: [O, O] | Phe-473<br>Asp-537<br>Arg-542 | Glu-513 |
| ATQSHQ<br>SEQ ID NO: 12 | Thr-424: [N]<br>Cys-425: [OH, NH]<br>Gln-427: [O]<br>Lys-453: [OH]<br>Ser-465: [NH2]<br>Arg-542: [O, O, O]<br>Glu-513: [NH2] | Cys-425 | None |
| DEKGPKWKR<br>SEQ ID NO: 13 | Asn-421: [NH2]<br>Asp-422: [NH2]<br>Thr-424: [O]<br>Leu-456: [NH2]<br>Ser-459: [NH]<br>Gln-471: [O]<br>Thr-477: [O]<br>Asp-510: [NH2, NH]<br>Thr-540: [O] | Leu-456<br>Thr-540 | Asp-422<br>Asp-510 |
| TCSYTMEA<br>SEQ ID NO: 14 | Phe-423: [NH]<br>Thr-477: [O]<br>Thr-424: [O]<br>Cys-425: [NH] | Cys-425<br>Ile-428<br>Leu-456<br>Phe-423 | None |

TABLE 2-continued

Interactions between 4KQZ receptor binding domain and residues of the top peptides of SEQ ID NOS: 1-27.

Interactions between RBD of S Protein and various peptides

| Peptide | Hydrogen bonds | Hydrophobic residues | Salt bridge interactions |
| --- | --- | --- | --- |
| | Ile-428: [SH]<br>Gln-427: [NH]<br>Leu-456: [NH]<br>Arg-542: [O, O]<br>Glu-513: [OH] | | |
| QGGQANQ<br>SEQ ID NO: 15 | Asp-422: [NH2]<br>Lys-453: [O]<br>Ser-457: [O]<br>Arg-542: [O, O, O]<br>Tyr-540: [O]<br>Gly-538: [NH2]<br>Glu-513: [NH2]<br>Cys-425: [NH]<br>Gln-427: [O]<br>Gln-471: [O] | Tyr-540<br>Cys-425 | None |
| FFFLSRIF<br>SEQ ID NO: 16 | Ser-426: [NH]<br>Lys-453: [O]<br>Leu-456: [NH]<br>Asp-537: [NH2, NH2]<br>Tyr-540: [O]<br>Arg-542: [O, O] | Tyr-540<br>Leu-456 | Asp-537 |
| DDDDDDD<br>SEQ ID NO: 17 | Cys-425: [NH, O]<br>Gln-427: [O]<br>Ser-465: [O]<br>Thr-477: [O]<br>Arg-542: [O, O, O, O]<br>Thr-424: [O] | Cys-425 | Arg-542<br>Lys-453<br>Arg-542 (2) |
| GSEIQPR<br>SEQ ID NO: 18 | Phe-423: [NH2]<br>Gln-427: [O]<br>Ile-428: [NH]<br>Lys-453: [O]<br>Gln-471: [OH]<br>Glu-513: [NH2]<br>Tyr-540: [O]<br>Arg-542: [O, O]<br>Ser-465: [O] | Tyr-540<br>Ile-428<br>Phe-423 | None |
| KTCENLADTY<br>SEQ ID NO: 19 | Ile-428: [OH]<br>Ser-426: [OH]<br>Ser-454: [NH2]<br>Ser-457: [O]<br>Val-458: [O]<br>Ser-459: [O, NH2] | Val-458<br>Ile-428 | None |
| GADDDDD<br>SEQ ID NO: 20 | Gln-427: [O]<br>Thr-477: [O]<br>Arg-542: [O, O, O]<br>Thr-424: [O]<br>Gln-471: [O] | | Lys-453,<br>Arg-542 |
| AWKLFDDGV<br>SEQ ID NO: 21 | Asn-501: [NH]<br>Asp-510: [NH]<br>Ser-457: [O]<br>Arg-542: [O, O]<br>Tyr-540: [O]<br>Lys-453: [O]<br>Gln-427: [NH2] | Tyr-540 | Arg-542<br>Lys-453 |
| AAGMGFFGAR<br>SEQ ID NO: 22 | Phe-473: [NH]<br>Asp-537: [NH]<br>Gln-427: [NH]<br>Arg-542: [O, O]<br>Ser-457: [NH]<br>Glu-536: [NH2, NH2] | Phe-473 | Glu-536 |

TABLE 2 -continued

Interactions between 4KQZ receptor binding domain and residues of the top peptides of SEQ ID NOS: 1-27.

Interactions between RBD of S Protein and various peptides

| Peptide | Hydrogen bonds | Hydrophobic residues | Salt bridge interactions |
|---|---|---|---|
| SMSGFSKPHD SEQ ID NO: 23 | Cys-425: [O]<br>Ser-426: [OH]<br>Ser-459: [OH]<br>Ser-457: [OH]<br>Lys-453: [OH]<br>Ser-472: [OH] | Cys-425 | None |
| RGSALTHLP SEQ ID NO: 24 | Gly-427: [O]<br>Cys-425: [NH]<br>Val-458: [O]<br>Ser-457: [OH]<br>Tyr-469: [NH2]<br>Gln-471: [NH]<br>Ser-472: [NH] | Val-458<br>Cys-425 | None |
| NRWCFAGDD SEQ ID NO: 25 | Cys-425: [O]<br>Arg-542: [O, O, O]<br>Ser-557: [NH] | Cys-425 | Arg-542<br>Lys-502 |
| DEDDD SEQ ID NO: 26 | Thr-424: [O]<br>Gln-471: [O]<br>Thr-477: [O]<br>Arg-542: [O]<br>Lys-453: [O] | None | Lys-502<br>Arg-542 (2)<br>Lys-453 |
| KIAKVALKAL SEQ ID NO: 27 | Asp-422: [NH2]<br>Phe-423: [NH]<br>Glu-513: [NH2]<br>Asp-537: [NH2, NH2]<br>Tyr-540: [O] | Tyr-540 | Asp-422,<br>Glu-513<br>Asp-537 |

Figure 2:
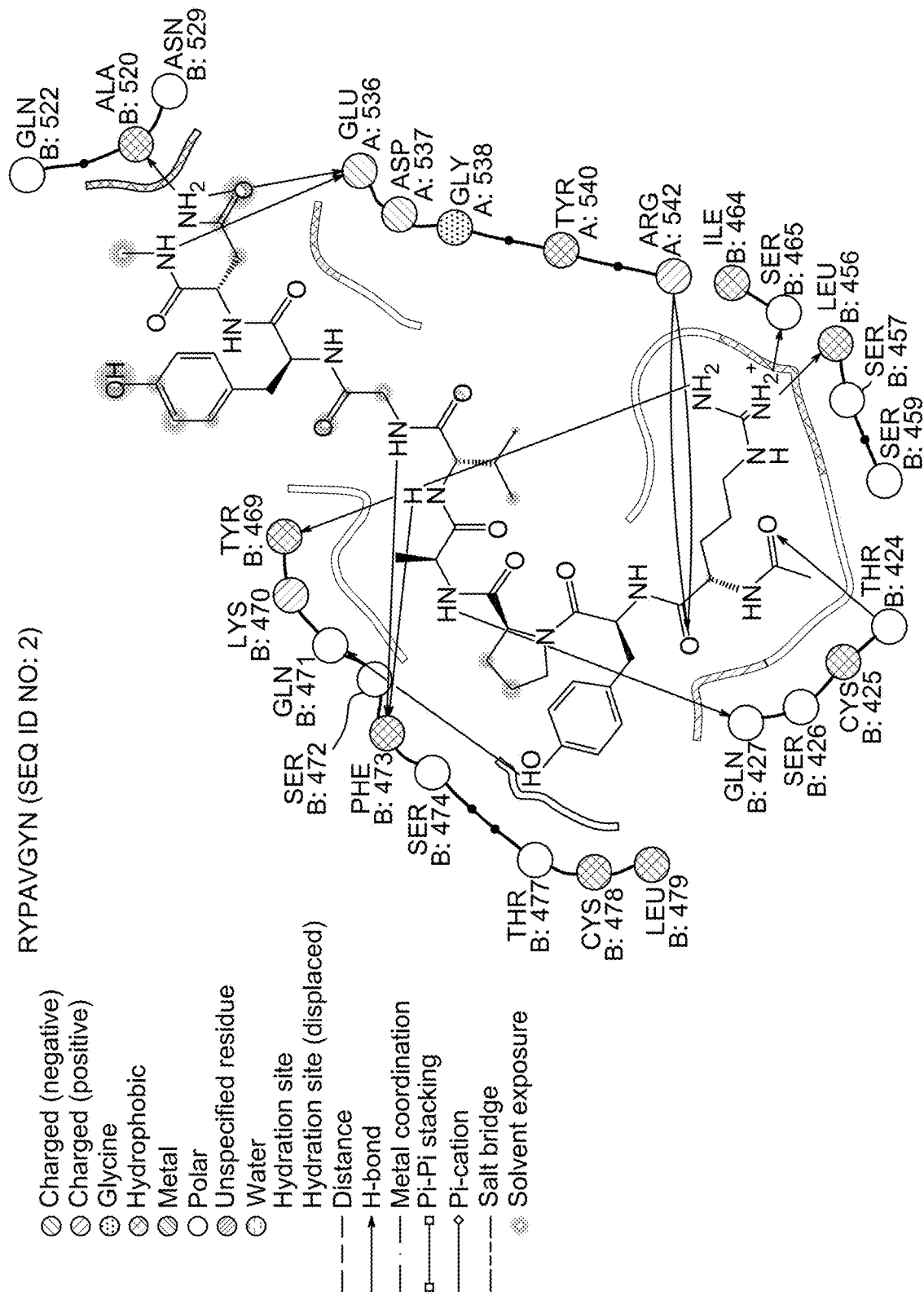
FIG. 2 shows the interactions of a peptide of SEQ ID NO: 2 with MERS-CoV receptor binding domain of spike protein of SEQ ID NO: 28. The peptide forms thirteen hydrogen bonds with Thr-424, Gln-427, Leu-456, Ser-465, Tyr-469, Gln-471, Phe-473, Ala-520, Glu-536, Arg-542), interacts with one aromatic hydrogen bond, and forms dual hydrogen bonds with each of Glu-536 and Arg-542.
Figure 3:
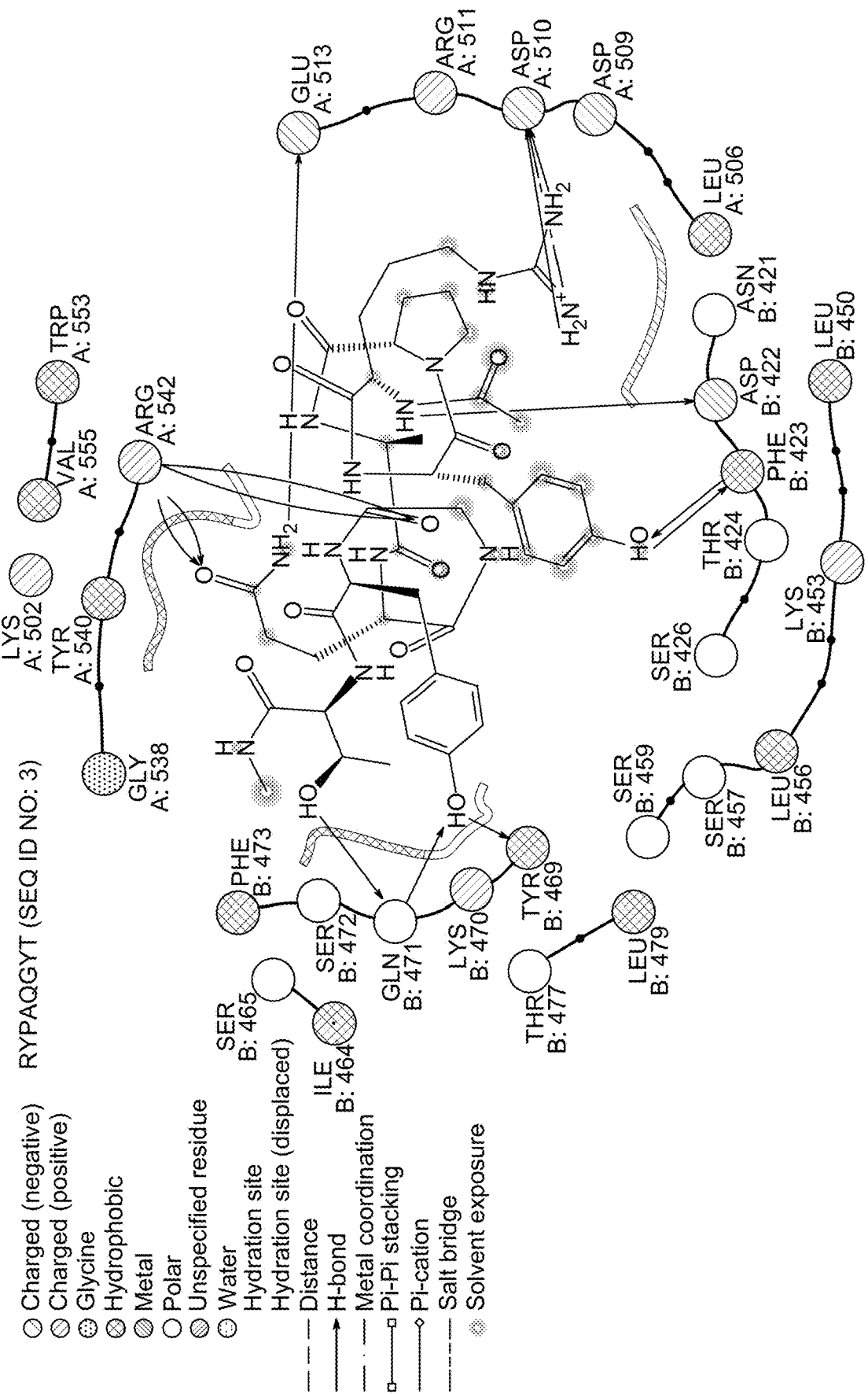
FIG. 3 shows the interactions of a peptide of SEQ ID NO: 3 with MERS-CoV receptor binding domain of spike protein of SEQ ID NO: 28. The peptide forms twelve hydrogen bonds with Asp-422, Phe-423, Tyr-469, Gln-471, Asp-510, Glu-513, Arg-542, interacts with two aromatic hydrogen bonds, and forms dual hydrogen bonds with each of Gln-471 and Phe-423. It also forms four hydrogen bonds with Arg-542 and one hydrogen bond and one salt bridge interaction with Asp-510.
Figure 4:
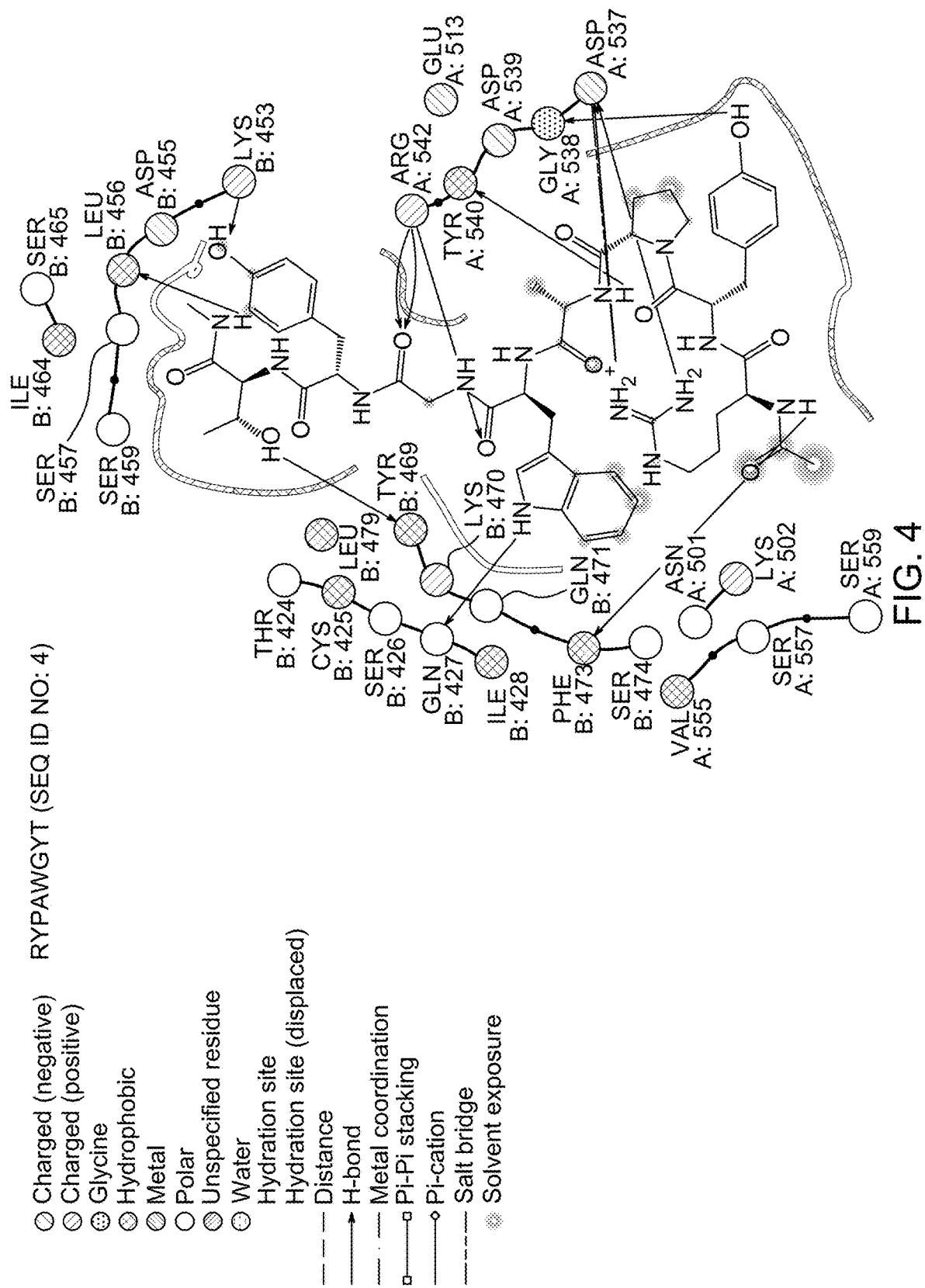
FIG. 4 shows the interactions of a peptide of SEQ ID NO: 4 with MERS-CoV receptor binding domain of spike protein of SEQ ID NO: 28. The peptide forms eleven hydrogen bonds (Gln-427, Lys-453, Leu-456, Tyr-469, Phe-473, Gly-538, Asp-537, Tyr-540, Arg-542) interactions with two aromatic hydrogen bond interactions. Arg-542 forms three hydrogen bonds while Asp-537 forms one hydrogen bond and one salt bridge.
Figure 5:
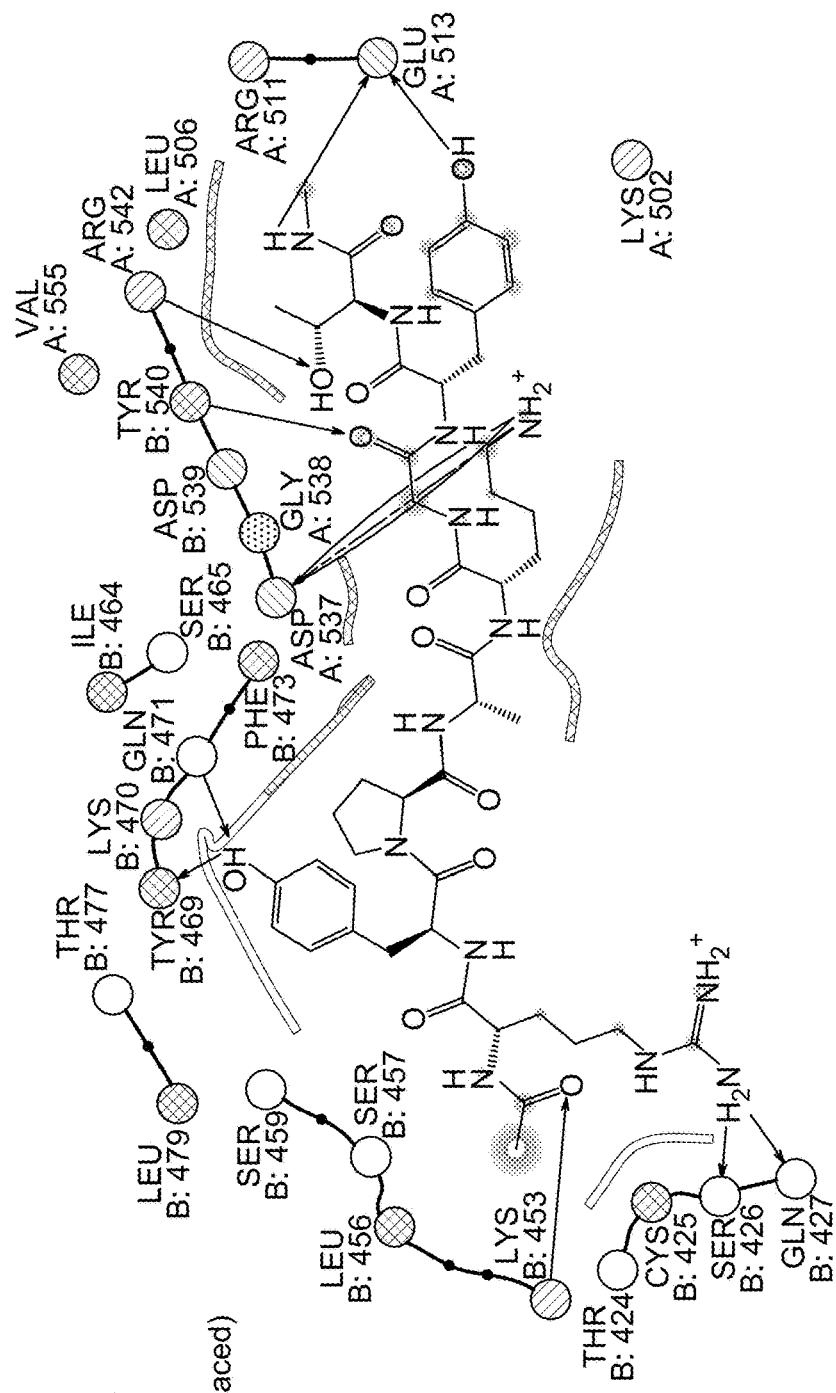
FIG. 5 shows the interactions of a peptide of SEQ ID NO: 5 with MERS-CoV receptor binding domain of spike protein of SEQ ID NO: 28. The peptide forms eleven hydrogen bonds (Ser-426, Gln-427, Lys-453, Tyr-469, Gln-471, Glu-513, Asp-537, Tyr-540, Arg-542) interactions with three aromatic hydrogen bond interactions. Glu-513 forms two hydrogen bonds while Asp-537 forms two hydrogen bonds and one salt bridge.
Figure 6:
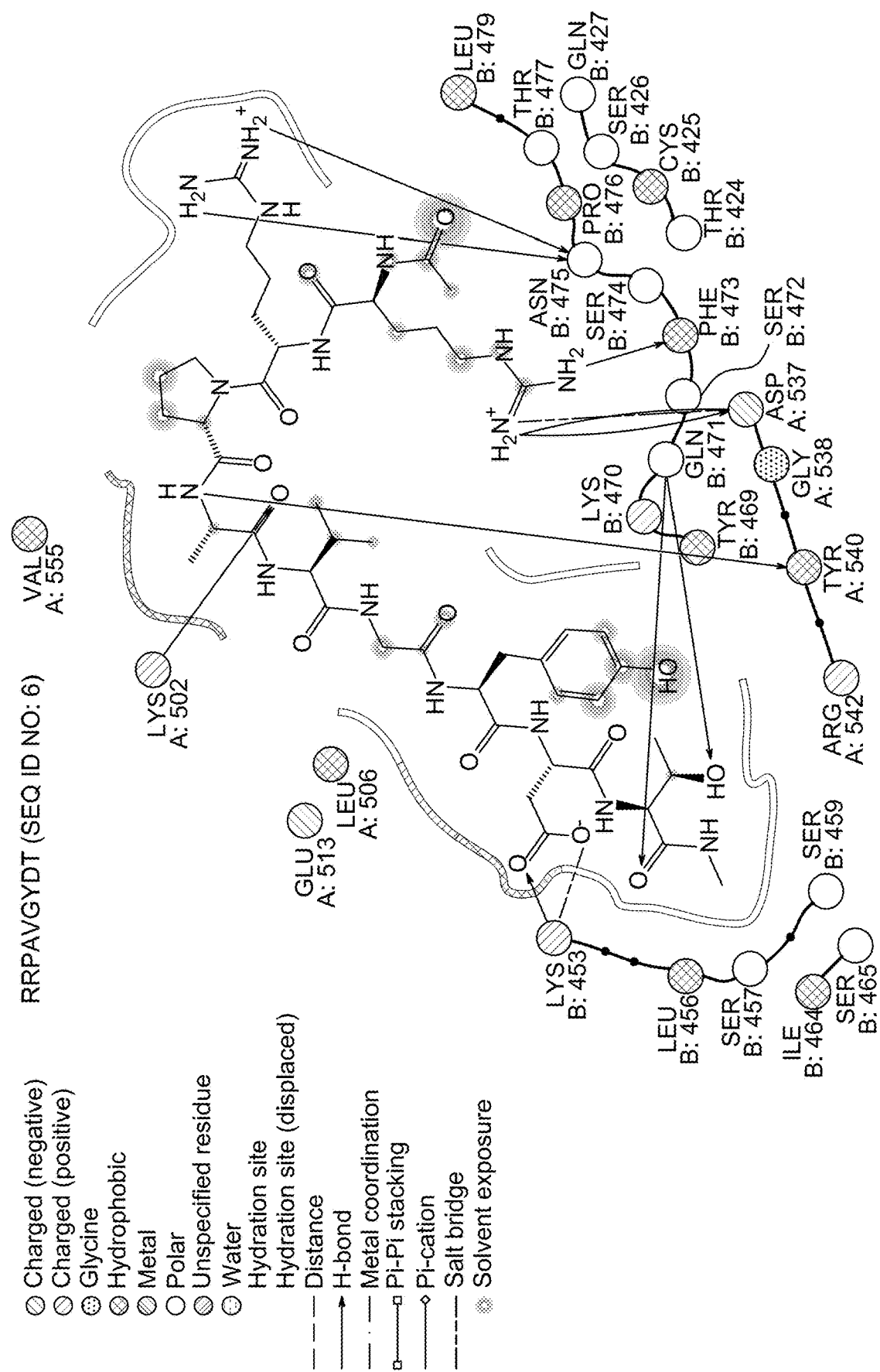
FIG. 6 shows the interactions of a peptide of SEQ ID NO: 6 with MERS-CoV receptor binding domain of spike protein of SEQ ID NO: 28. The peptide forms ten hydrogen bonds (Lys-453, Gln-471, Phe-473, Asn-475, Lys-502, Asp-537, Tyr-540) interactions with two aromatic hydrogen bonds interactions. Lys-453 form one hydrogen bond and one salt bridge, while Asp-537 forms two hydrogen bonds with one salt bridge.
Figure 7:
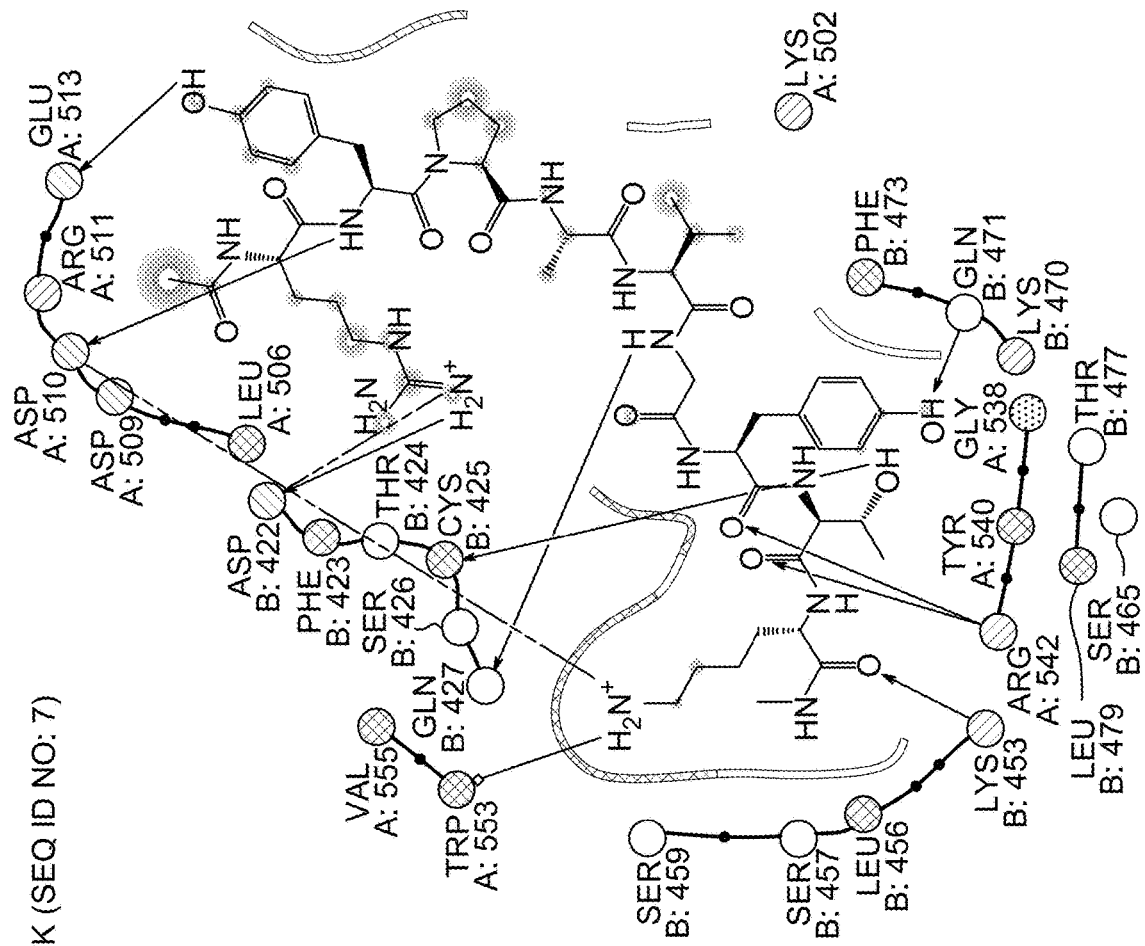
FIG. 7 shows the interactions of a peptide of SEQ ID NO: 7 with MERS-CoV receptor binding domain of spike protein of SEQ ID NO: 28. The peptide forms nine hydrogen bonds (Glu-513, Asp-422, Arg-542, Cys-425, Gln-427, Lys-453, Gln-471, Asp-510) interactions with three aromatic H bonds interactions. Arg-542 forms two hydrogen bonds. Both Asp-422 and Asp-510 form one hydrogen bond and one salt bridge. Trp-553 forms an-cation interaction.
Figure 8:
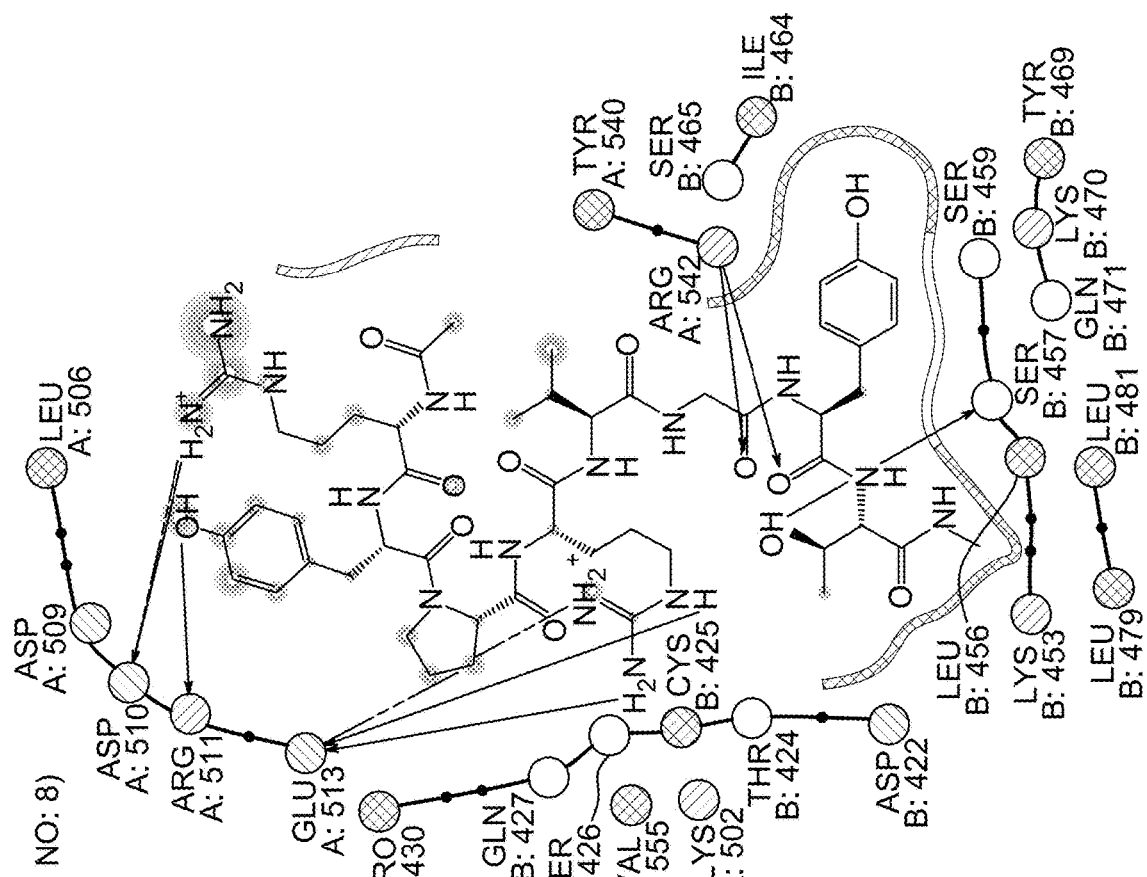
FIG. 8 shows the interactions of a peptide of SEQ ID NO: 8 with MERS-CoV receptor binding domain of spike protein of SEQ ID NO: 28. The peptide forms seven hydrogen bonds (Asp-510, Arg-511, Glu-513, Ser-457, Arg-542) interactions with two aromatic hydrogen bonds interactions. Arg-542 forms two hydrogen bonds. Asp-510 forms one hydrogen bond and one salt bridge, while Glu-513 forms two hydrogen bonds with one salt bridge.
Figure 9:
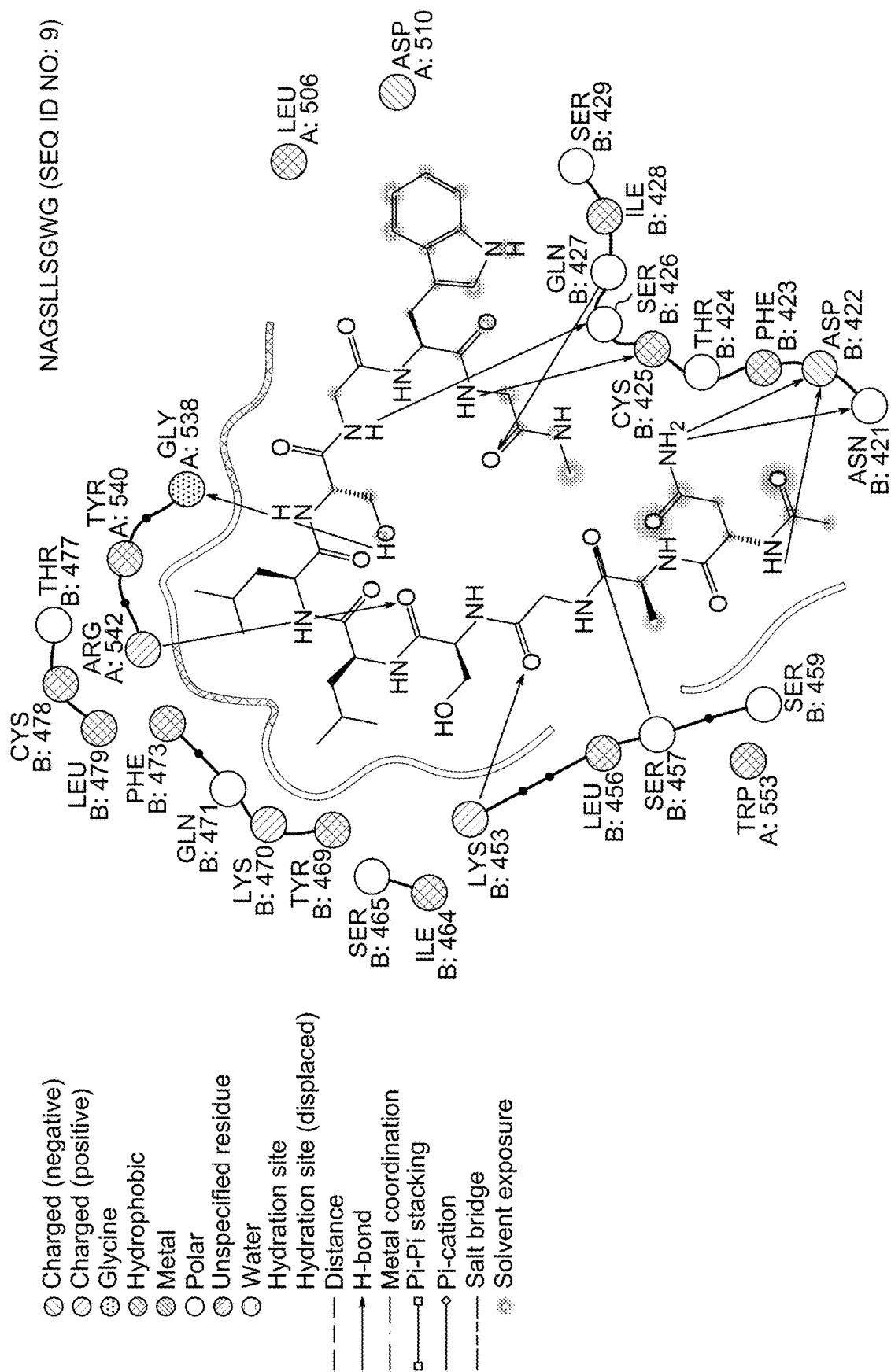
FIG. 9 shows the interactions of a peptide of SEQ ID NO: 9 with MERS-CoV receptor binding domain of spike protein of SEQ ID NO: 28. The peptide forms ten hydrogen bonds to Asn-421, Asp-422, Cys-425, Ser-426, Gln-427, Ser-457, Lys-453, Arg-542, and Gly-538. Asp-422 forms two hydrogen bond interactions.
Figure 10:
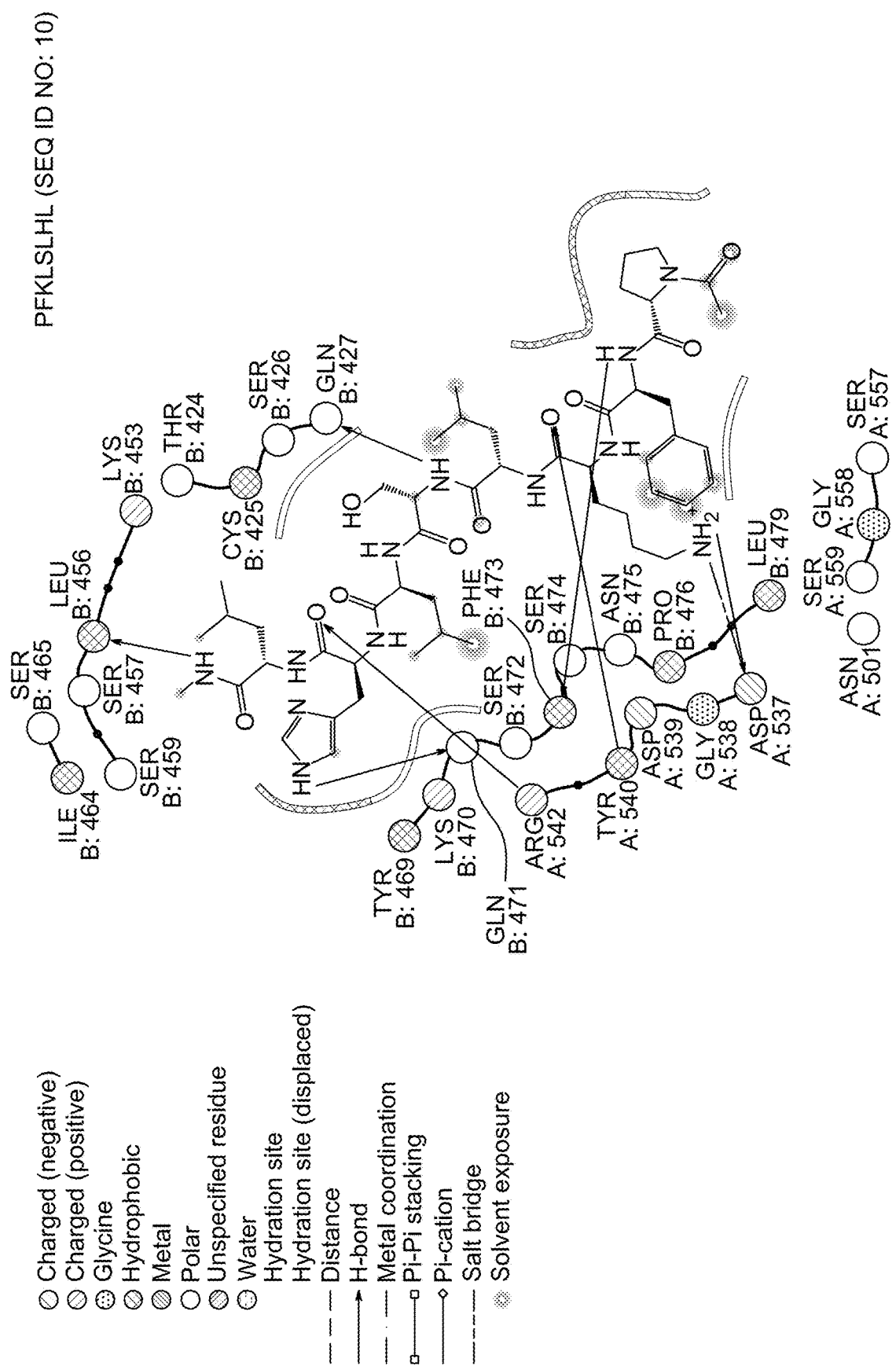
FIG. 10 shows the interactions of a peptide of SEQ ID NO: 10 with MERS-CoV receptor binding domain of spike protein of SEQ ID NO: 28. The peptide forms seven hydrogen bonds to Gln-427, Leu-456, Gln-471, Phe-473, Asp-537, Tyr-540, and Arg-542, and exhibits two aromatic hydrogen interactions. Asp-537 forms one salt bridge interaction.
Figure 11:
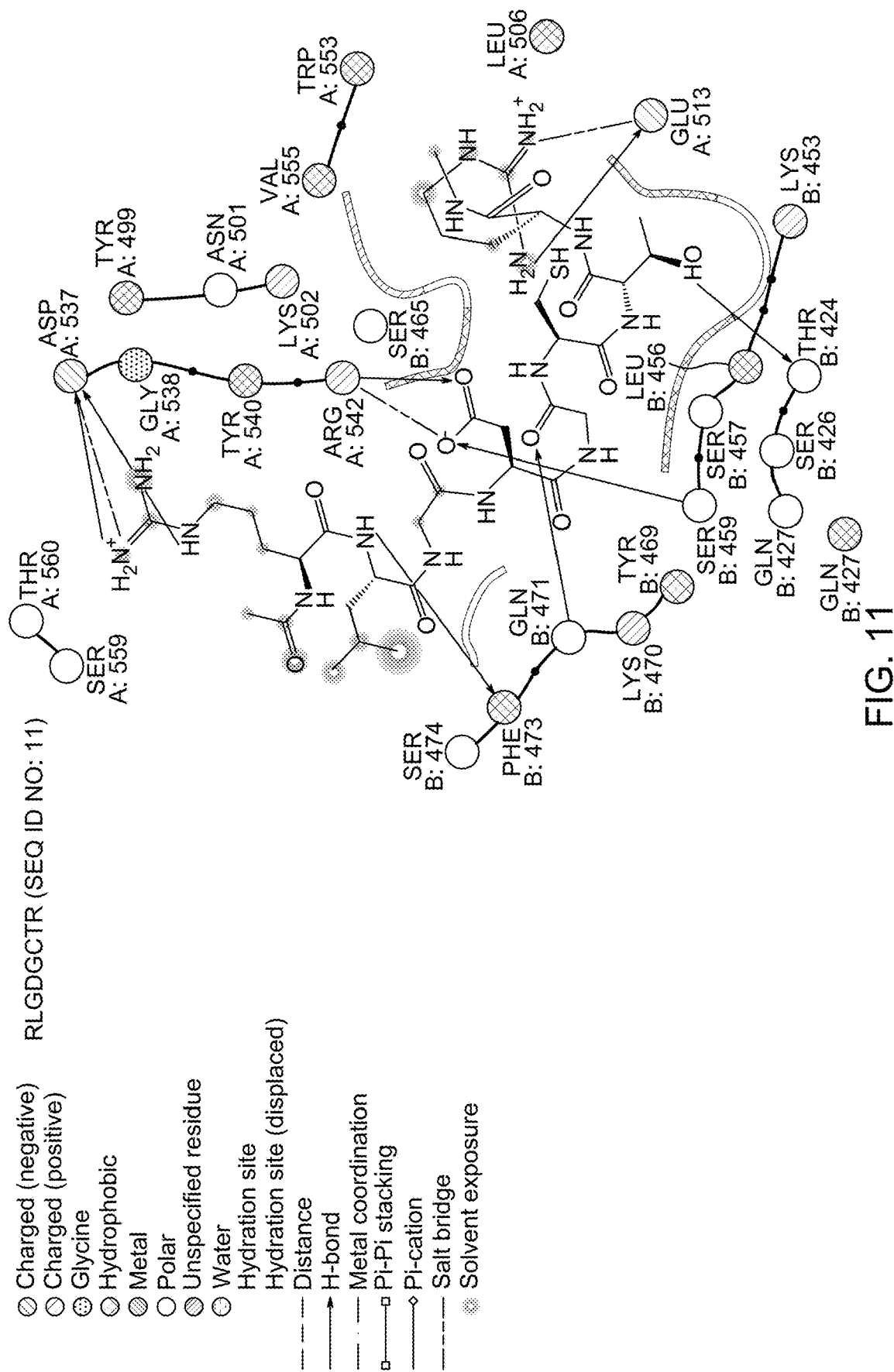
FIG. 11 shows the interactions of a peptide of SEQ ID NO: 11 with MERS-CoV receptor binding domain of spike protein of SEQ ID NO: 28. The peptide forms ten hydrogen bonds to Thr-424, Ser-459, Gln-471, Phe-473, Glu-513, Asp-537, and Arg-542. Glu-513 and Asp-537 and Arg-542, each forms two-hydrogen bonds. Glu-513, Asp-537, and Arg-542, each form a salt bridges.
Figure 12:
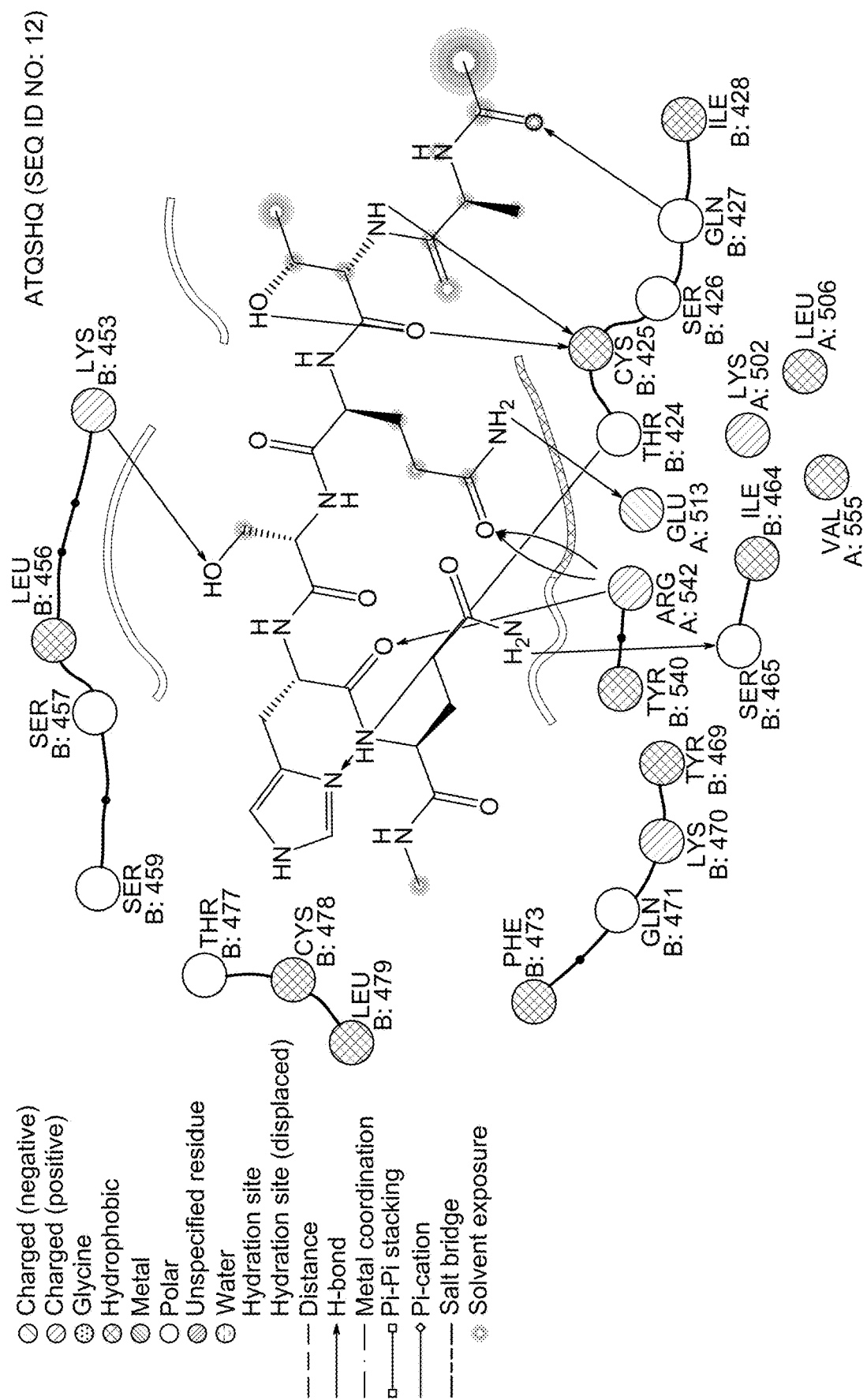
FIG. 12 shows the interactions of a peptide of SEQ ID NO: 12 with MERS-CoV receptor binding domain of spike protein of SEQ ID NO: 28. The peptide forms ten hydrogen bonds at Thr-424, Cys-425, Gln-427, Lys-453, Ser-465, Arg-542, Glu-513 and exhibits one aromatic hydrogen bond. Cys-425 forms two hydrogen bonds. Arg-542 forms three hydrogen bonds.
Figure 13:
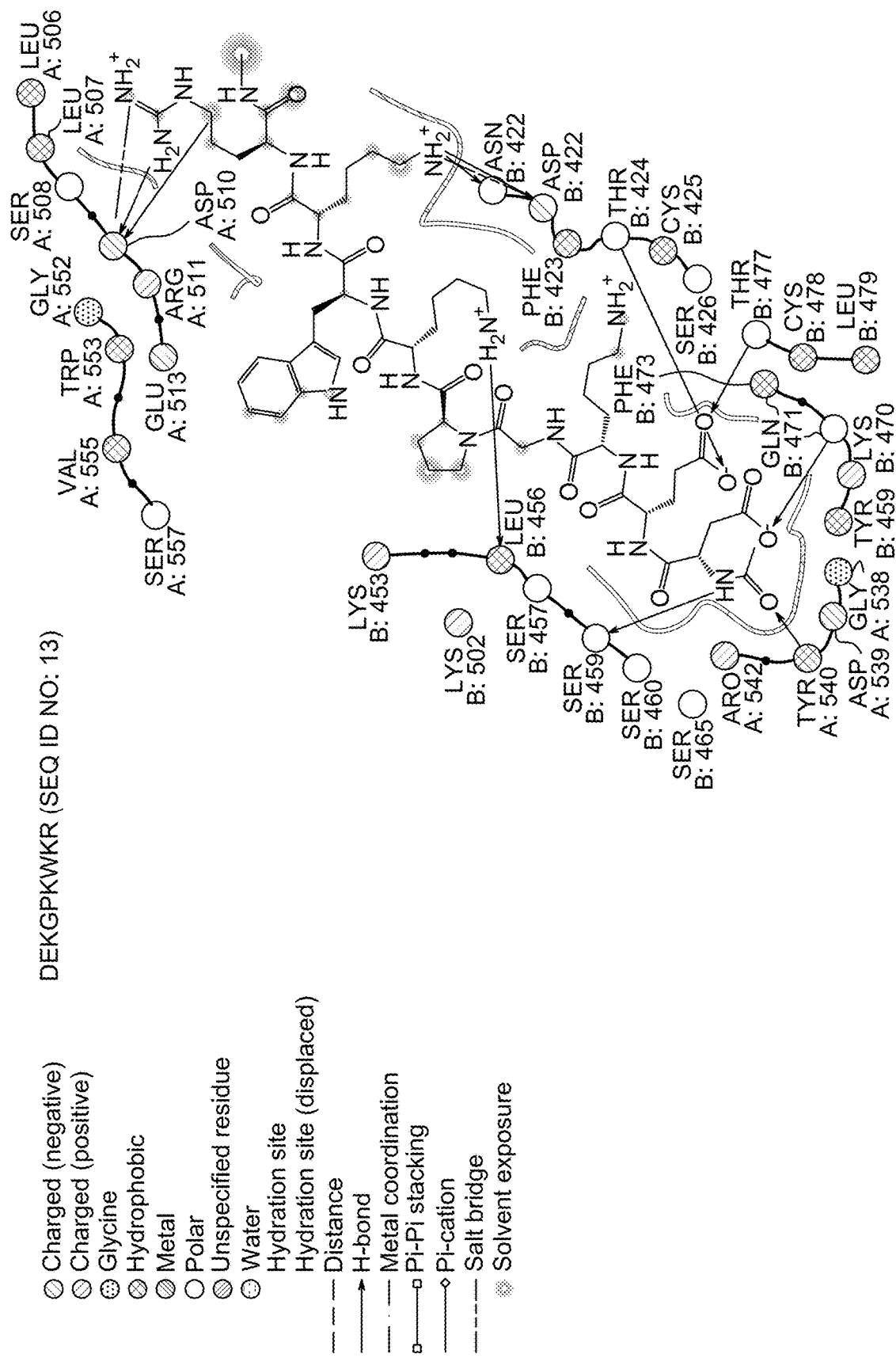
FIG. 13 shows the interactions of a peptide of SEQ ID NO: 13 with MERS-CoV receptor binding domain of spike protein of SEQ ID NO: 28. The peptide forms ten hydrogen bonds to Asn-421, Asn-422, Thr-424, Leu-456, Ser-459, Gln-471, Thr-477, Asp-510, and Thr-540, and exhibits one aromatic hydrogen interaction. Asp-510 forms two hydrogen bonds. Asn-422 and Asp-510 form salt bridges.
Figure 14:
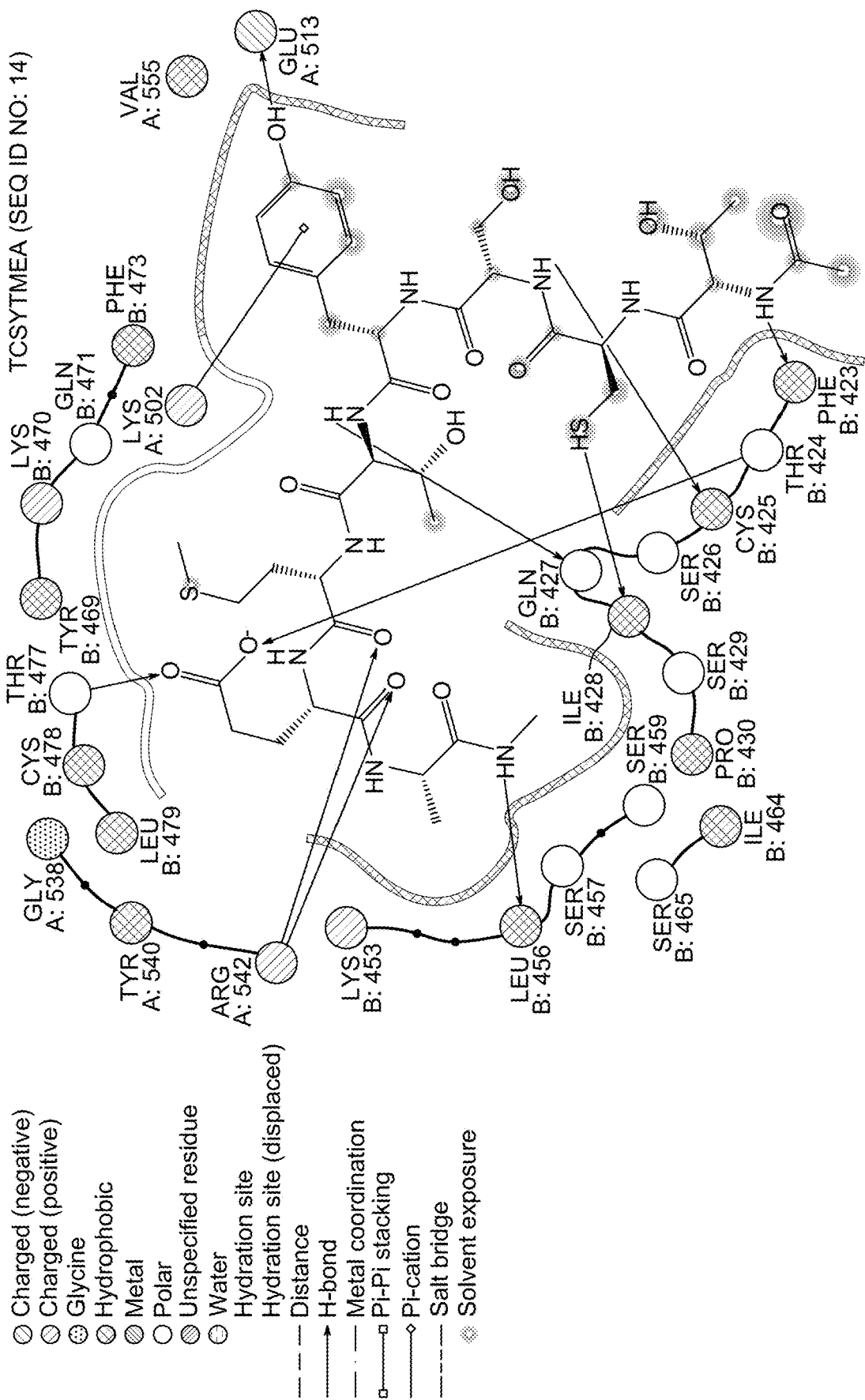
FIG. 14 shows the interactions of a peptide of SEQ ID NO: 14 with MERS-CoV receptor binding domain of spike protein of SEQ ID NO: 28. The peptide forms ten hydrogen bonds to Phe-423, Thr-424, Cys-425, Ile-428, Gln-427, Lys-453, Leu-456, Thr-477, Arg-542, and Glu 513, and exhibits one aromatic hydrogen interaction. Arg-542 forms two hydrogen bonds. Lys 502 forms a cation π-interaction.
Figure 15:
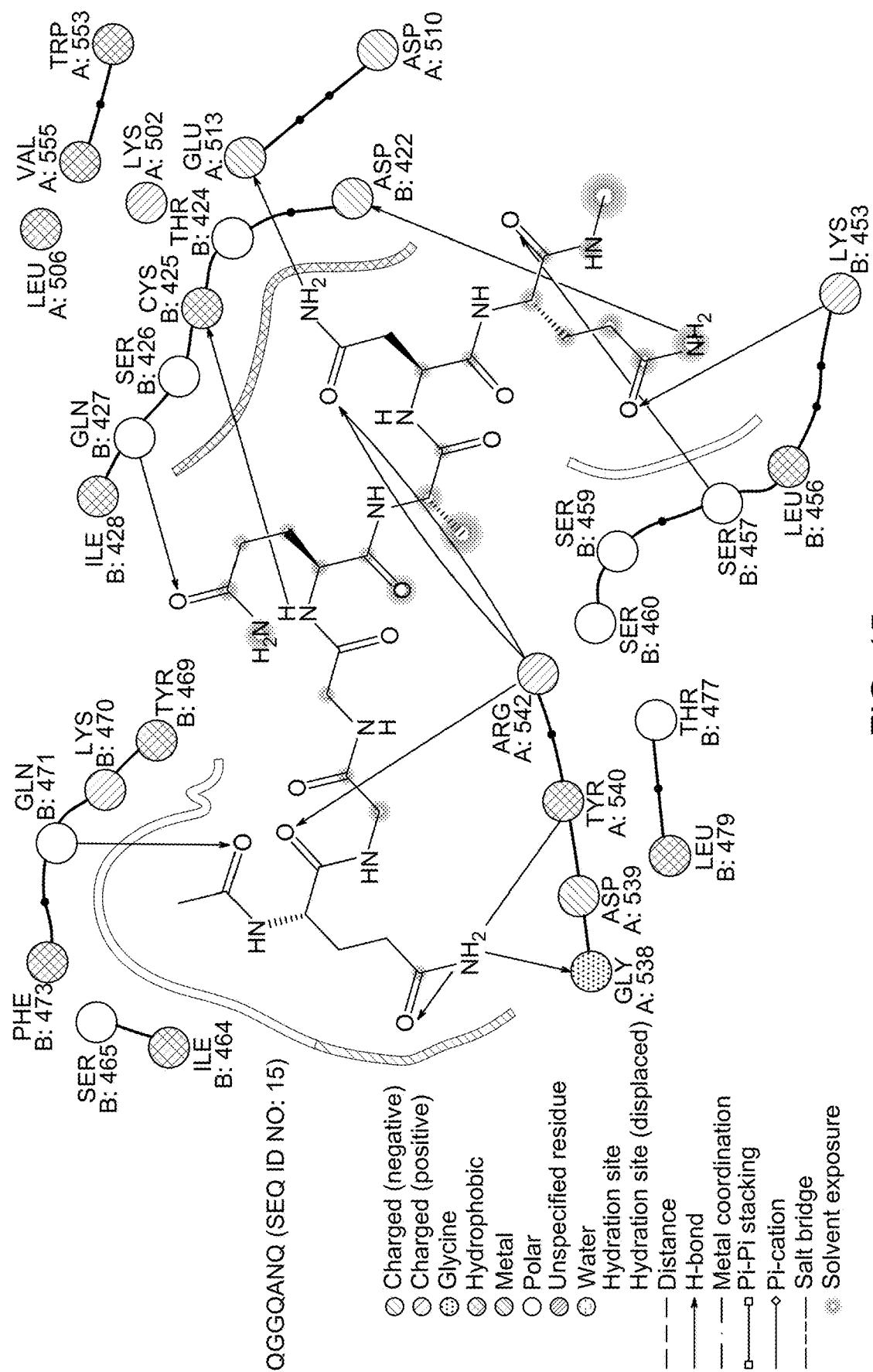
FIG. 15 shows the interactions of a peptide of SEQ ID NO: 15 with MERS-CoV receptor binding domain of spike protein of SEQ ID NO: 28. The peptide forms twelve hydrogen bonds Asp-422, Lys-453, Ser-457, Arg-542, Tyr-540, Gly-538, Glu-513, Cys-425, Gln-427, and Gln-471. Arg-542 forms three hydrogen bonds.
Figure 16:
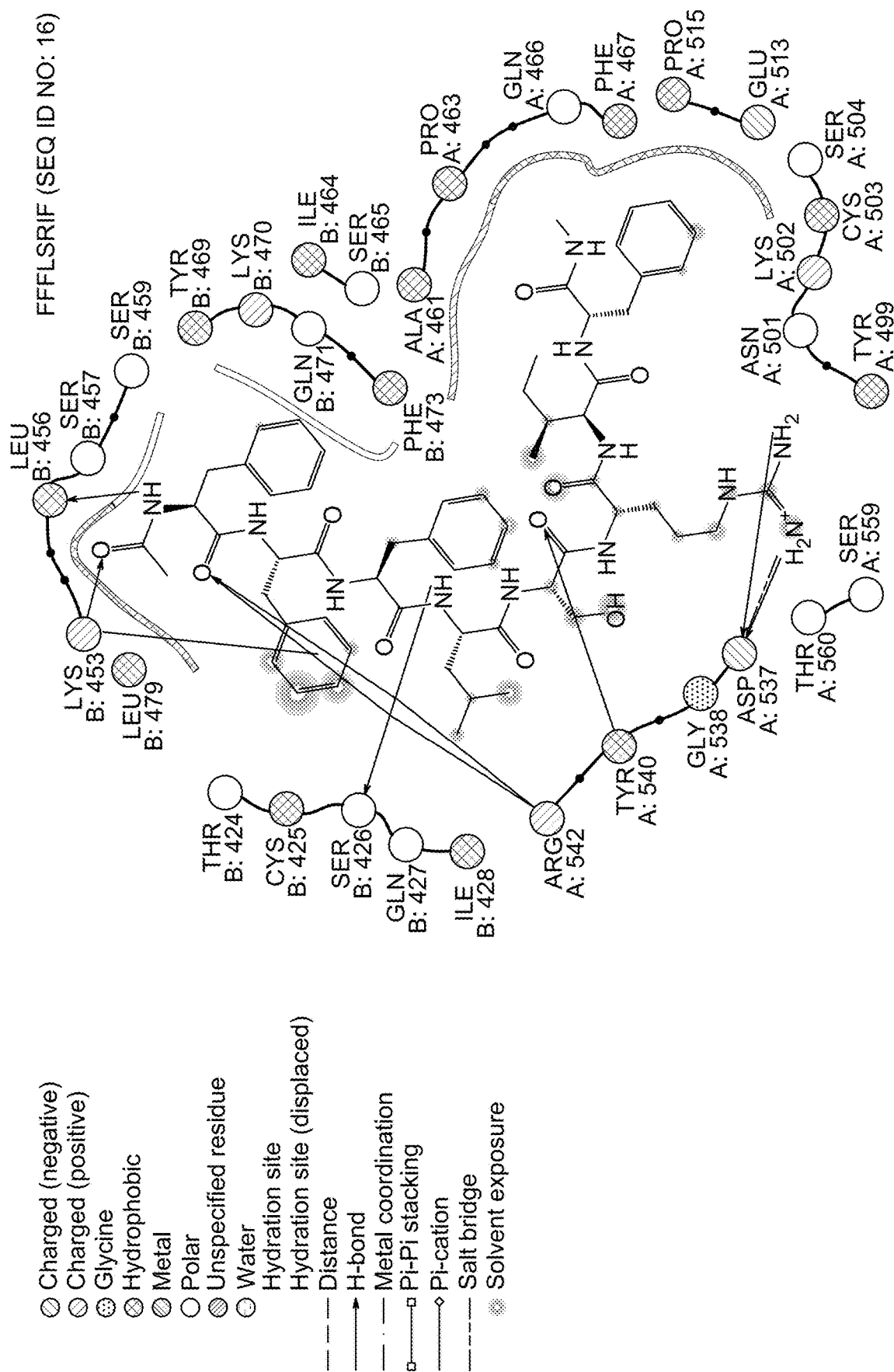
FIG. 16 shows the interactions of a peptide of SEQ ID NO: 16 with MERS-CoV receptor binding domain of spike protein of SEQ ID NO: 28. The peptide forms eight hydrogen bonds Ser-426, Lys-453, Leu-456, Asp-537, Tyr-540, Arg-542, and Asp-537, and exhibits four aromatic hydrogen interactions. Arg-542 and Asp-537 forms two hydrogen bonds each. Asp 537 forms a salt bridge interaction. Lys 453 forms a π-cation interaction.
Figure 17:
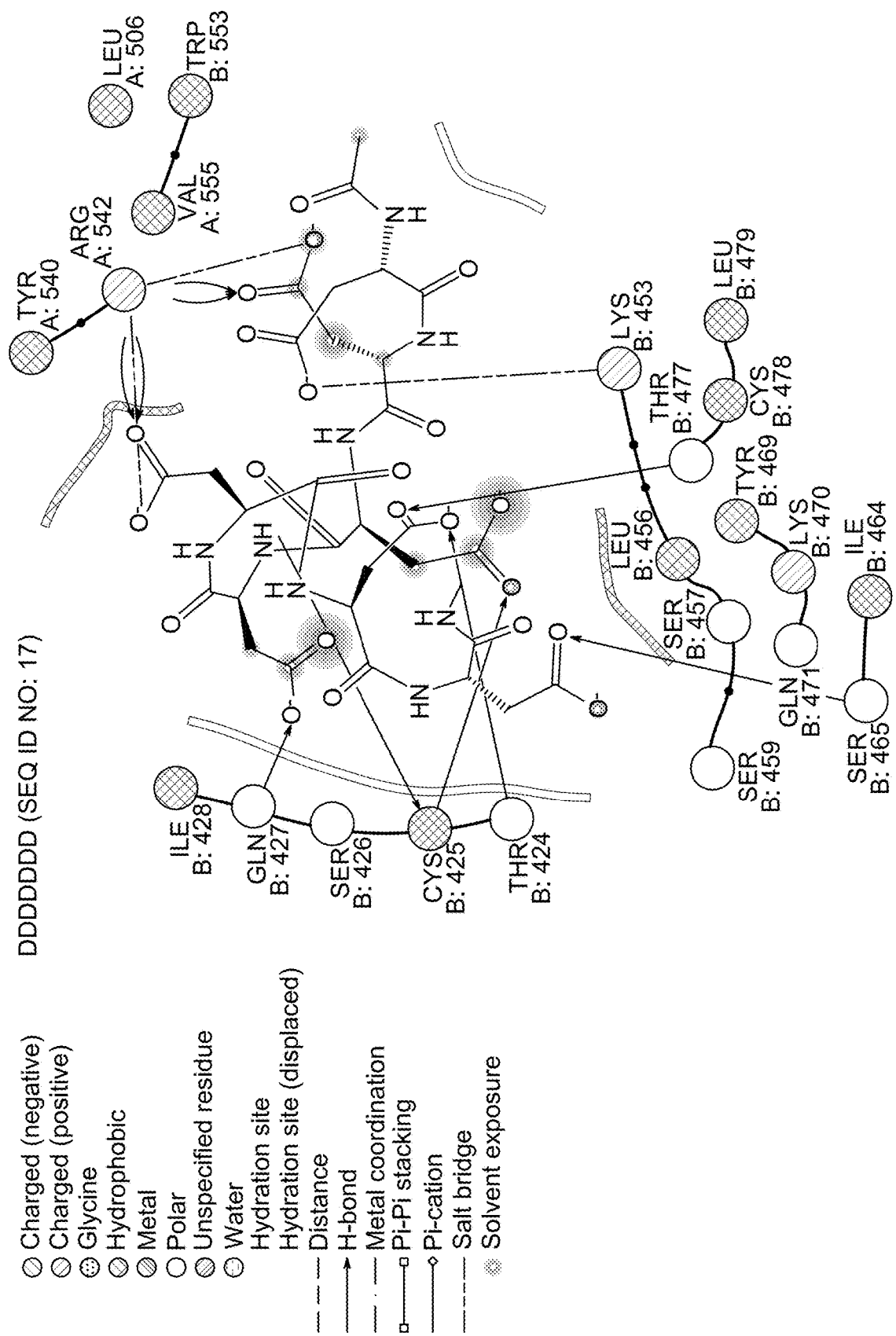
FIG. 17 shows the interactions of a peptide of SEQ ID NO: 17 with MERS-CoV receptor binding domain of spike protein of SEQ ID NO: 28. The peptide forms ten hydrogen bonds (Thr-424, Cys-425, Gln-427, Ser-465, Thr-477, Arg-542) with four aromatic hydrogen bonds. Arg-542 forms four hydrogen bonds. Cys-425 forms 2 hydrogen bonds. Arg-542 forms two salt bridges along with Lys-453.
Figure 18:
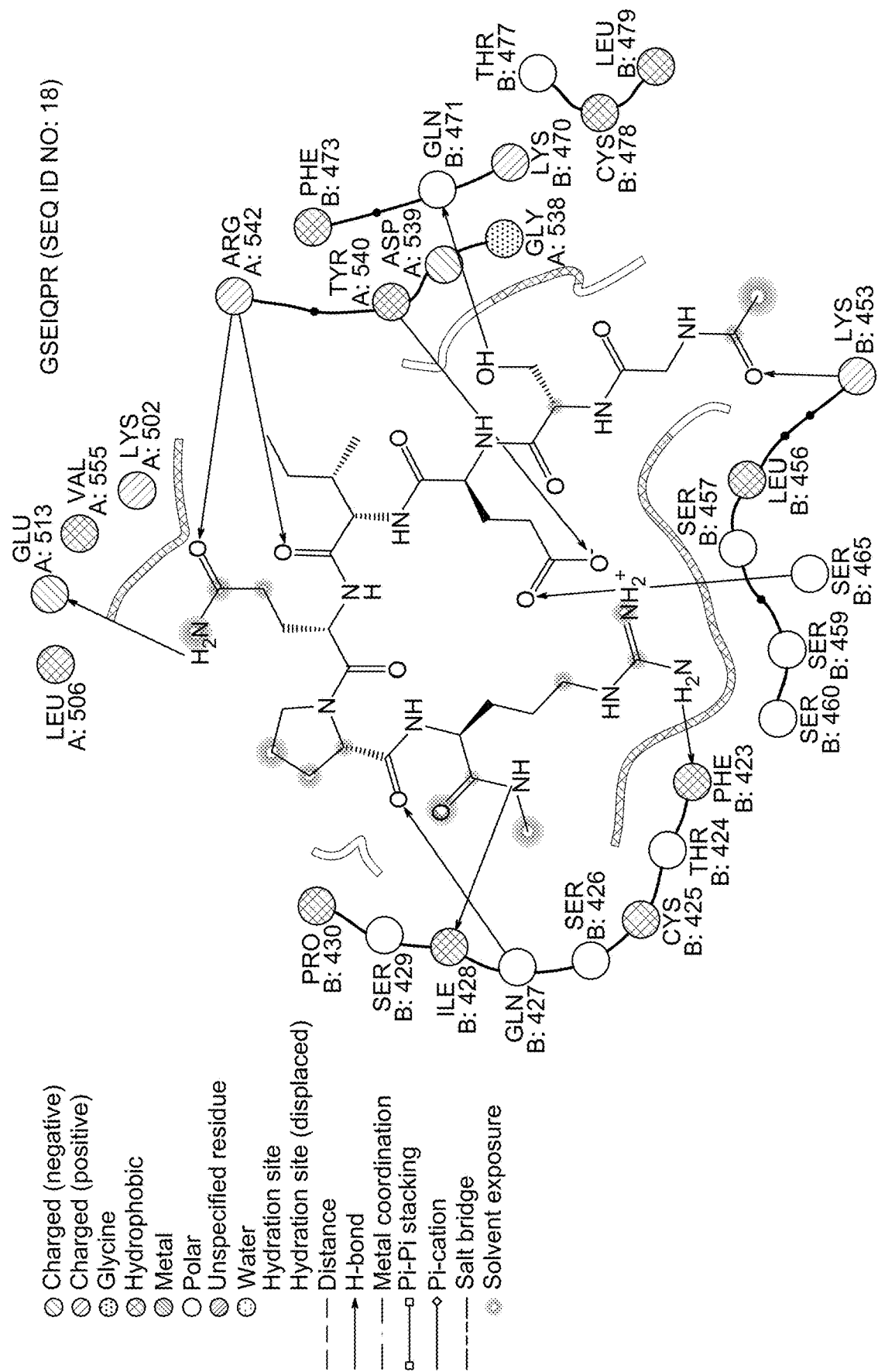
FIG. 18 shows the interactions of a peptide of SEQ ID NO: 18 with MERS-CoV receptor binding domain of spike protein of SEQ ID NO: 28. The peptide forms ten hydrogen bonds to Phe-423, Gln-427, Ile-428, Lys-453, Gln-471, Glu-513, Tyr-540, Arg-542, and Ser-465. Arg-542 forms two hydrogen bonds.
Figure 19:
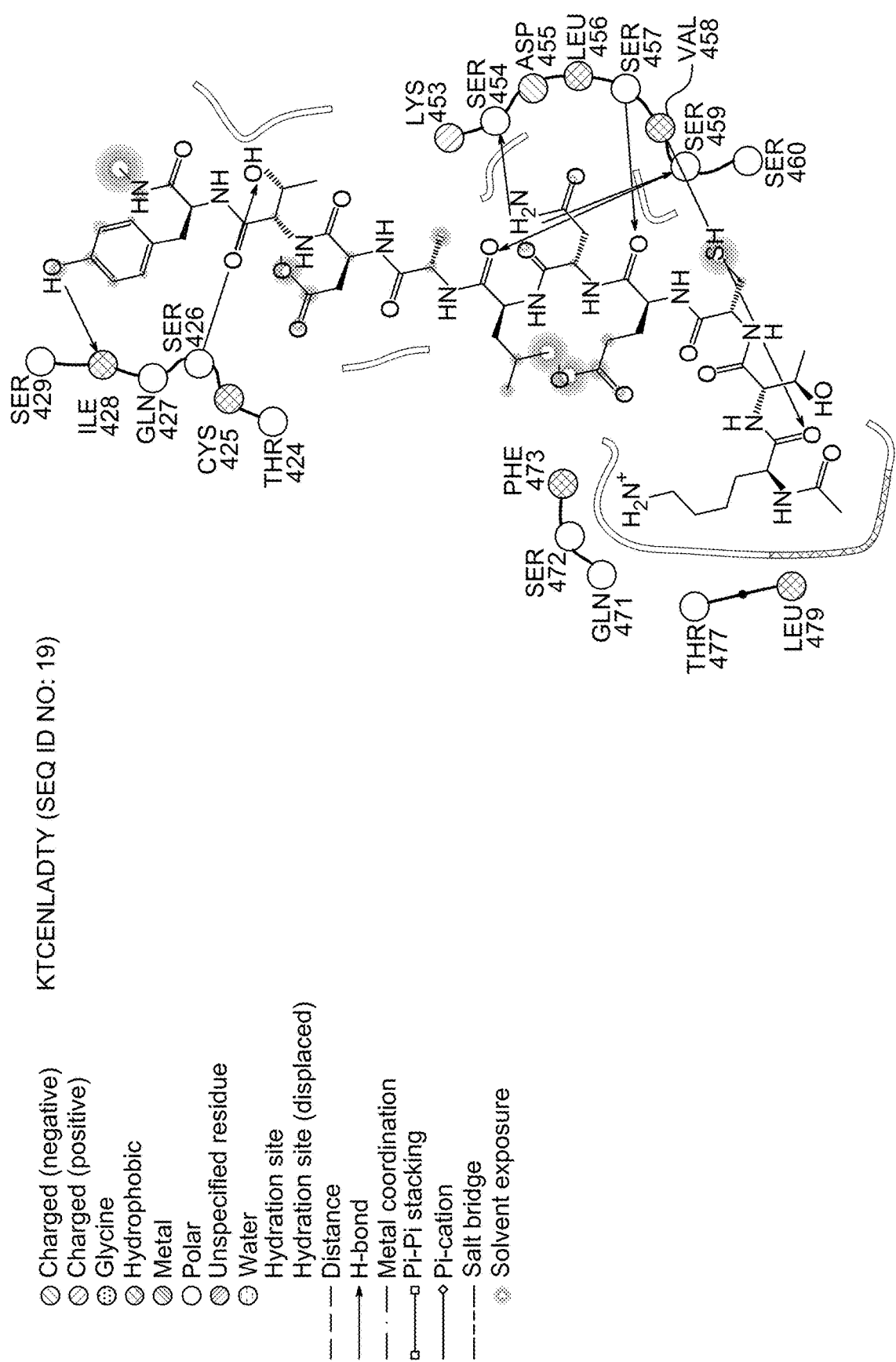
FIG. 19 shows the interactions of a peptide of SEQ ID NO: 19 with MERS-CoV receptor binding domain of spike protein of SEQ ID NO: 28. The peptide forms seven hydrogen bonds to Ile-428, Ser-426, Ser-454, Ser-457, Val-458, and Ser-459. Ser-459 forms two hydrogen bond interactions.
Figure 20:
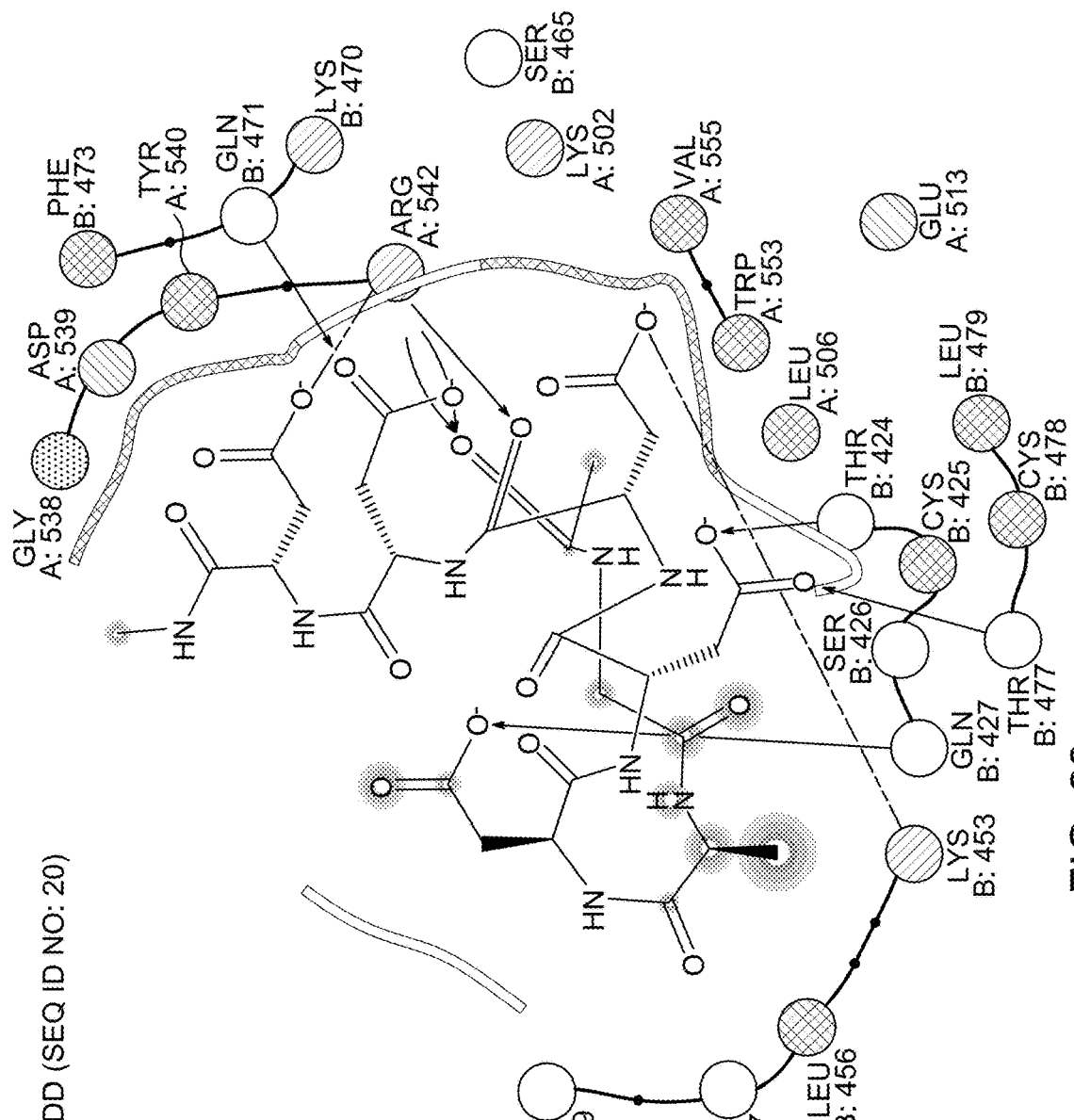
FIG. 20 shows the interactions of a peptide of SEQ ID NO: 20 with MERS-CoV receptor binding domain of spike protein of SEQ ID NO: 28. The peptide forms seven hydrogen bonds (Gln-427, Thr-477, Arg-542, Thr-424, Gln-471) with one aromatic H bond. Arg-542 forms three hydrogen bonds. Lys-453 and Arg-542, each forms one salt bridge interaction.
Figure 21:
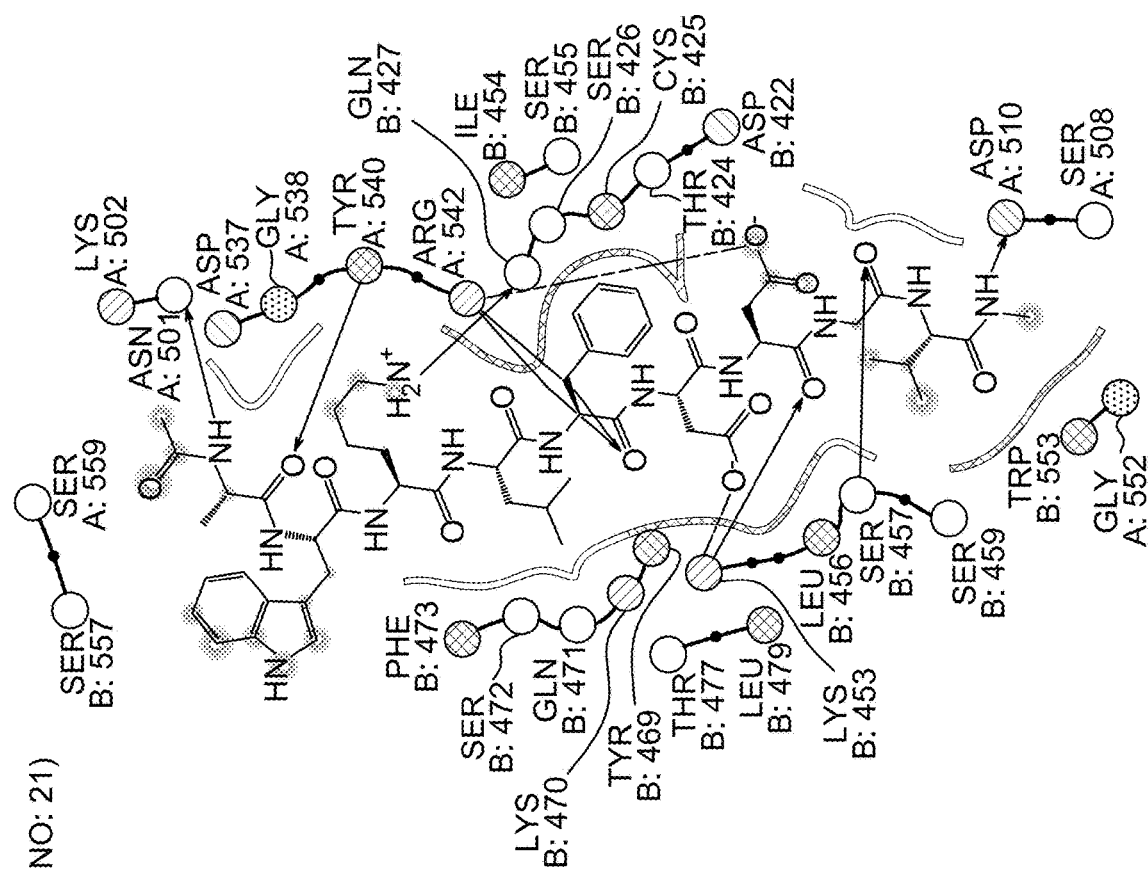
FIG. 21 shows the interactions of a peptide of a peptide of SEQ ID NO: 21 with MERS-CoV receptor binding domain of spike protein of SEQ ID NO: 28. The peptide forms eight hydrogen bonds to Asn-501, Asp-510, Ser-457, Arg-542, Tyr-540, Lys-453, and Gln-427, and exhibits three aromatic hydrogen interactions. Arg-542 forms two hydrogen bonds. Arg-542 and Lys 453 form salt bridge interactions.
Figure 22:
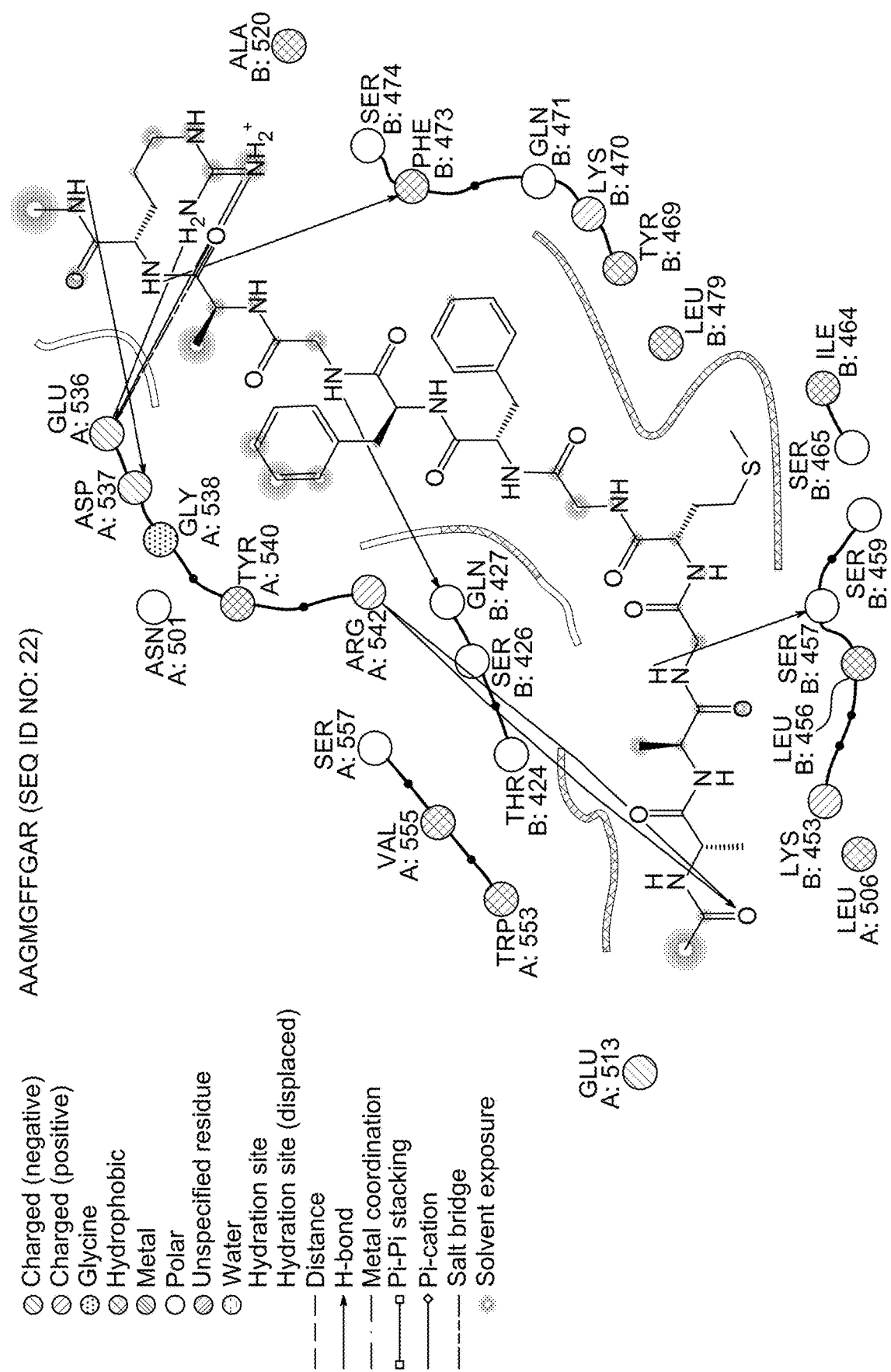
FIG. 22 shows the interactions of a peptide of SEQ ID NO: 22 with MERS-CoV receptor binding domain of spike protein of SEQ ID NO: 28. The peptide forms eight hydrogen bonds to Phe-473, Asp-537, Gln-427, Arg-542, Ser-457, and Glu-536, and exhibits two aromatic hydrogen interactions. Arg-542 and Glu-536 forms two hydrogen bonds each. Glu-536 forms a salt bridge.
Figure 23:
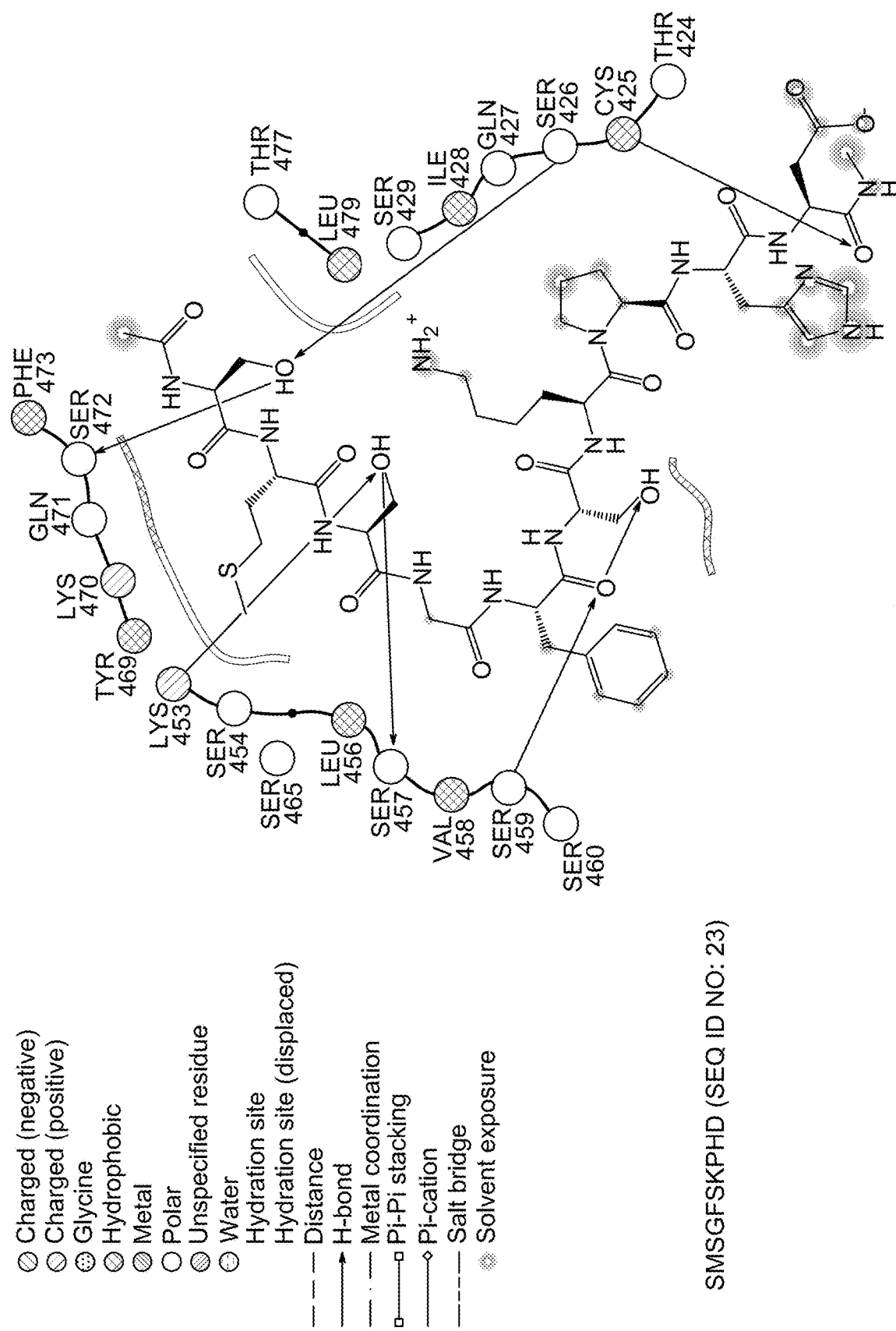
FIG. 23 shows the interactions of a peptide of SEQ ID NO: 23 with MERS-CoV receptor binding domain of spike protein of SEQ ID NO: 28. The peptide forms six hydrogen bonds to Cys-425, Ser-426, Ser-459, Ser-457, Lys-453, and Ser-472.
Figure 24:
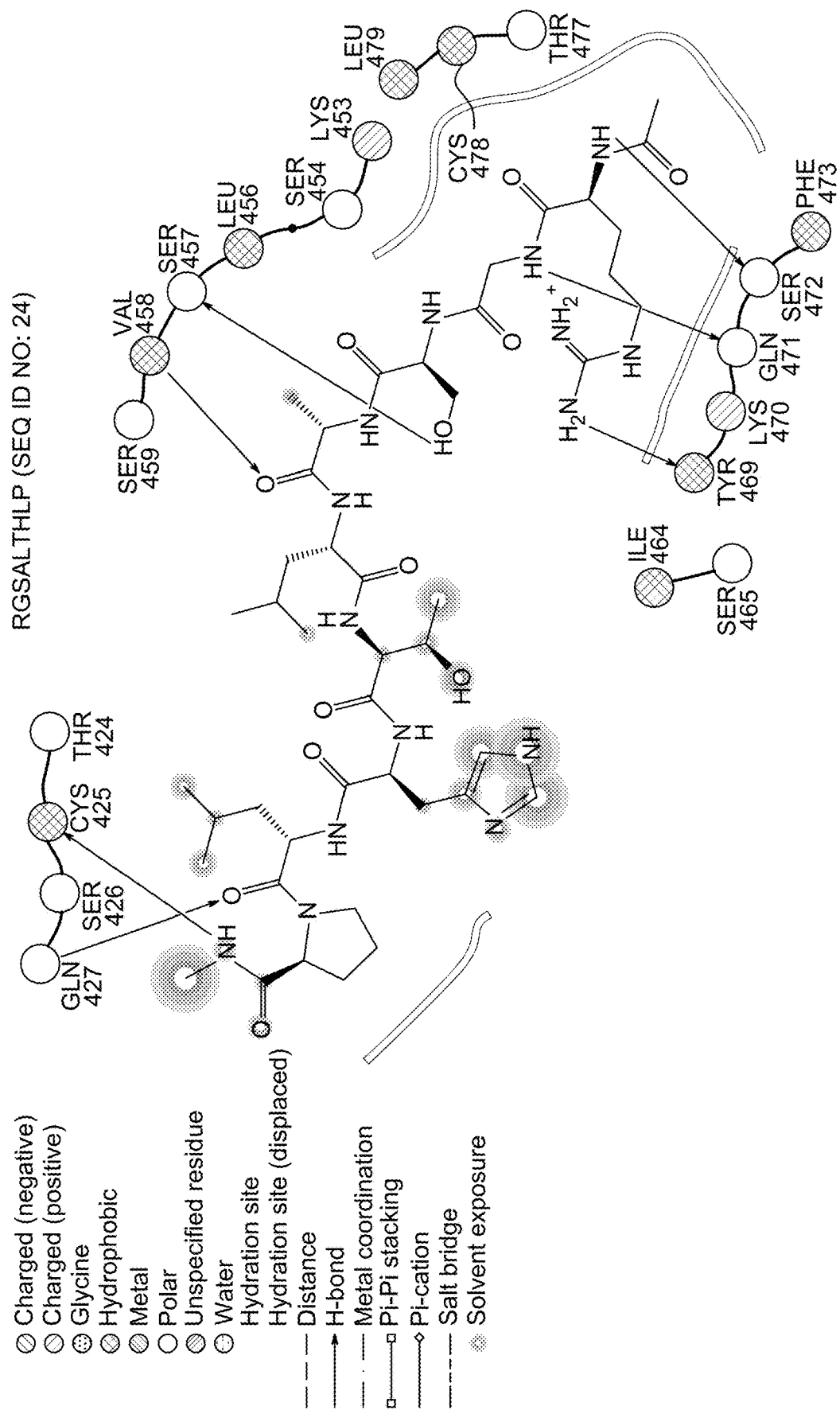
FIG. 24 shows the interactions of a peptide of SEQ ID NO: 24 with MERS-CoV receptor binding domain of spike protein of SEQ ID NO: 28. The peptide forms seven hydrogen bonds to Gly-427, Cys-425, Val-458, Ser-457, Tyr-469, Gln-471, and Ser-472.
Figure 25:
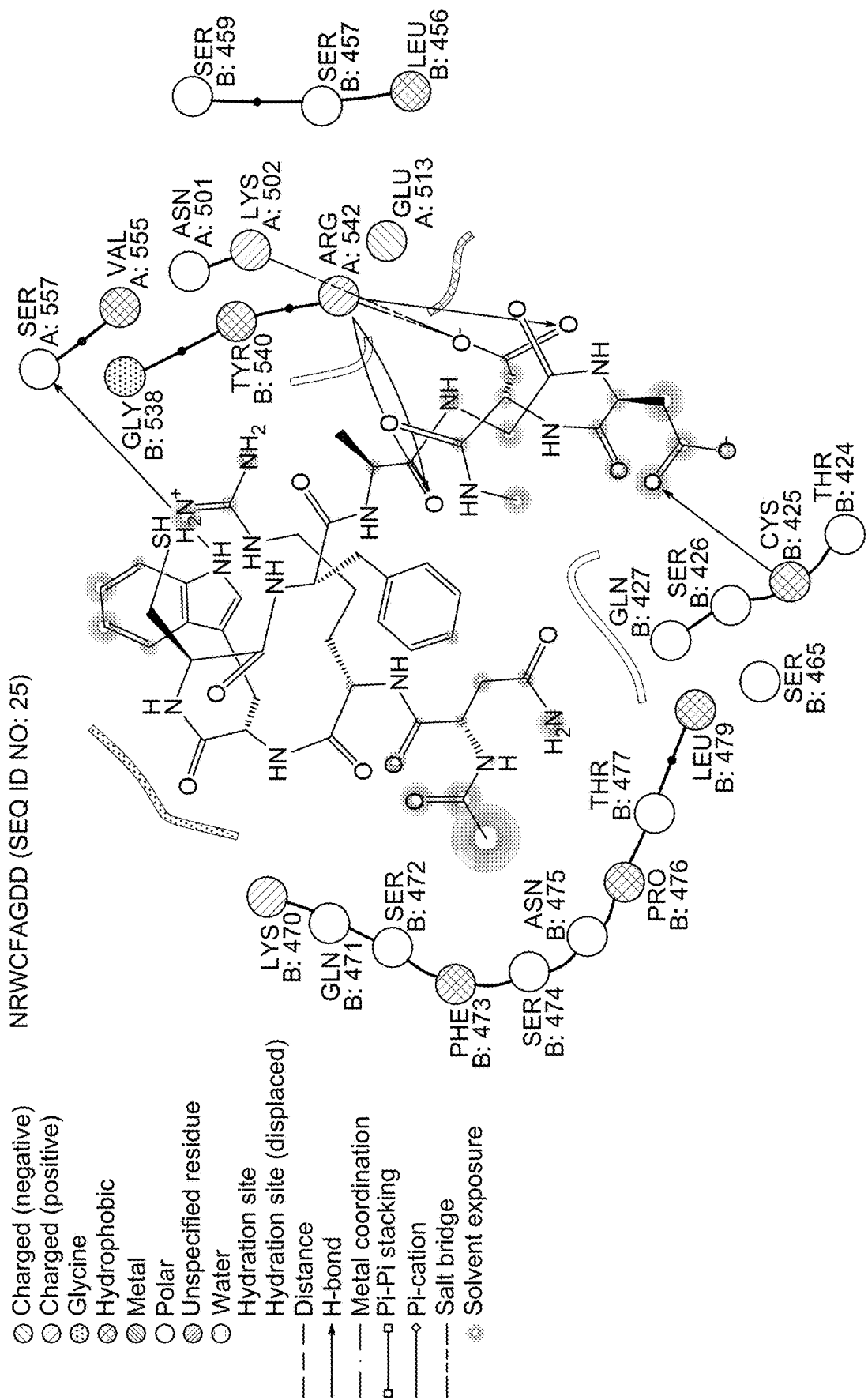
FIG. 25 shows the interactions of a peptide of SEQ ID NO: 25 with MERS-CoV receptor binding domain of spike protein of SEQ ID NO: 28. The peptide forms five hydrogen bonds to Cys-425, Arg-542, and Ser-557, and an aromatic hydrogen interaction. Arg-542 forms two hydrogen bonds. Arg-542 and Lys-502 form two salt bridges with the peptide.
Figure 26:
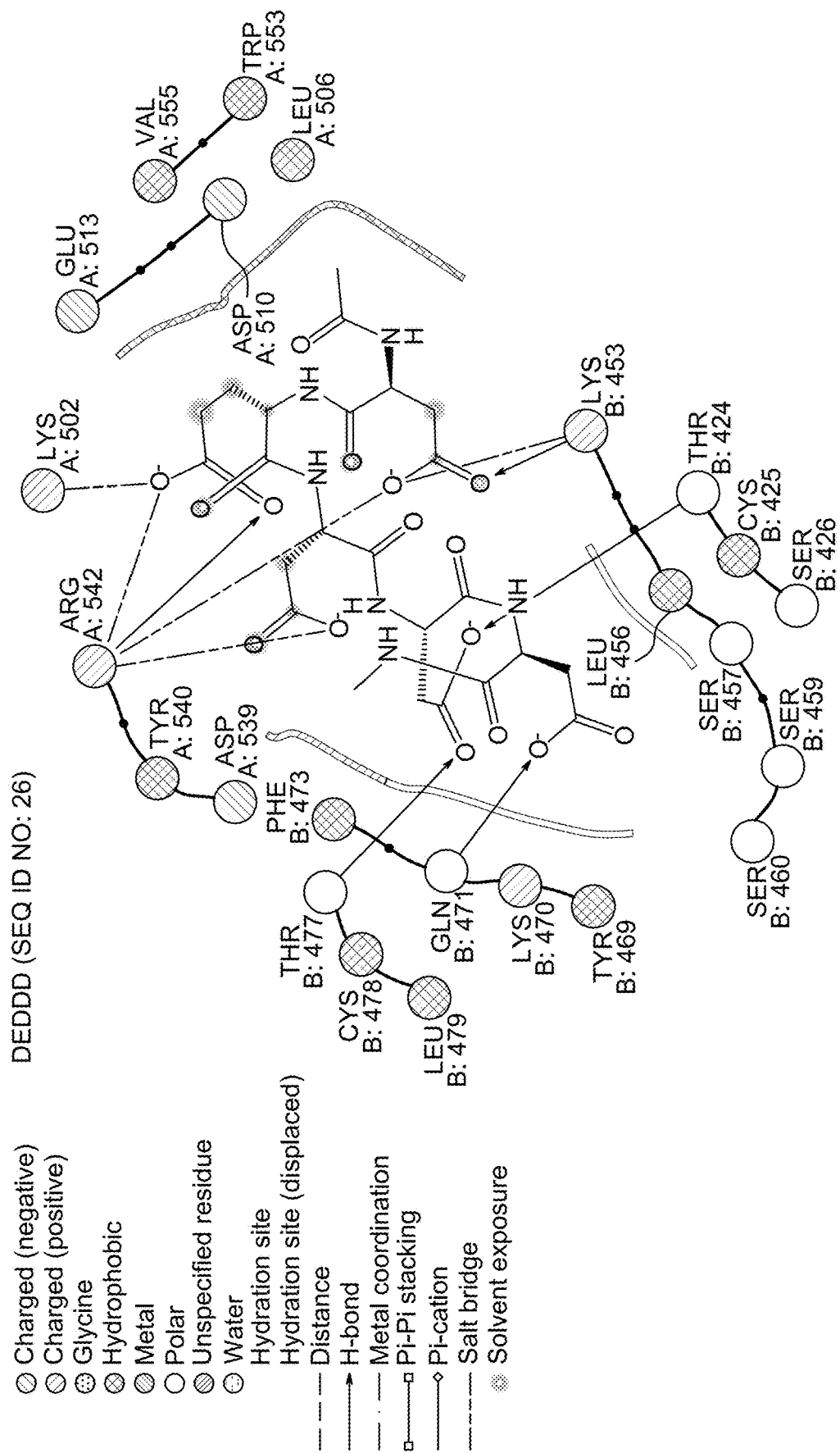
FIG. 26 shows the interactions of a peptide of SEQ ID NO: 26 with MERS-CoV receptor binding domain of spike protein of SEQ ID NO: 28. The peptide forms five hydrogen bonds to Thr-424, Gln-471, Thr-477, Arg-542, Lys-453. Arg-542 forms two salt bridges while Lys 453 and Lys 502, each form one salt bridge.
Figure 27:
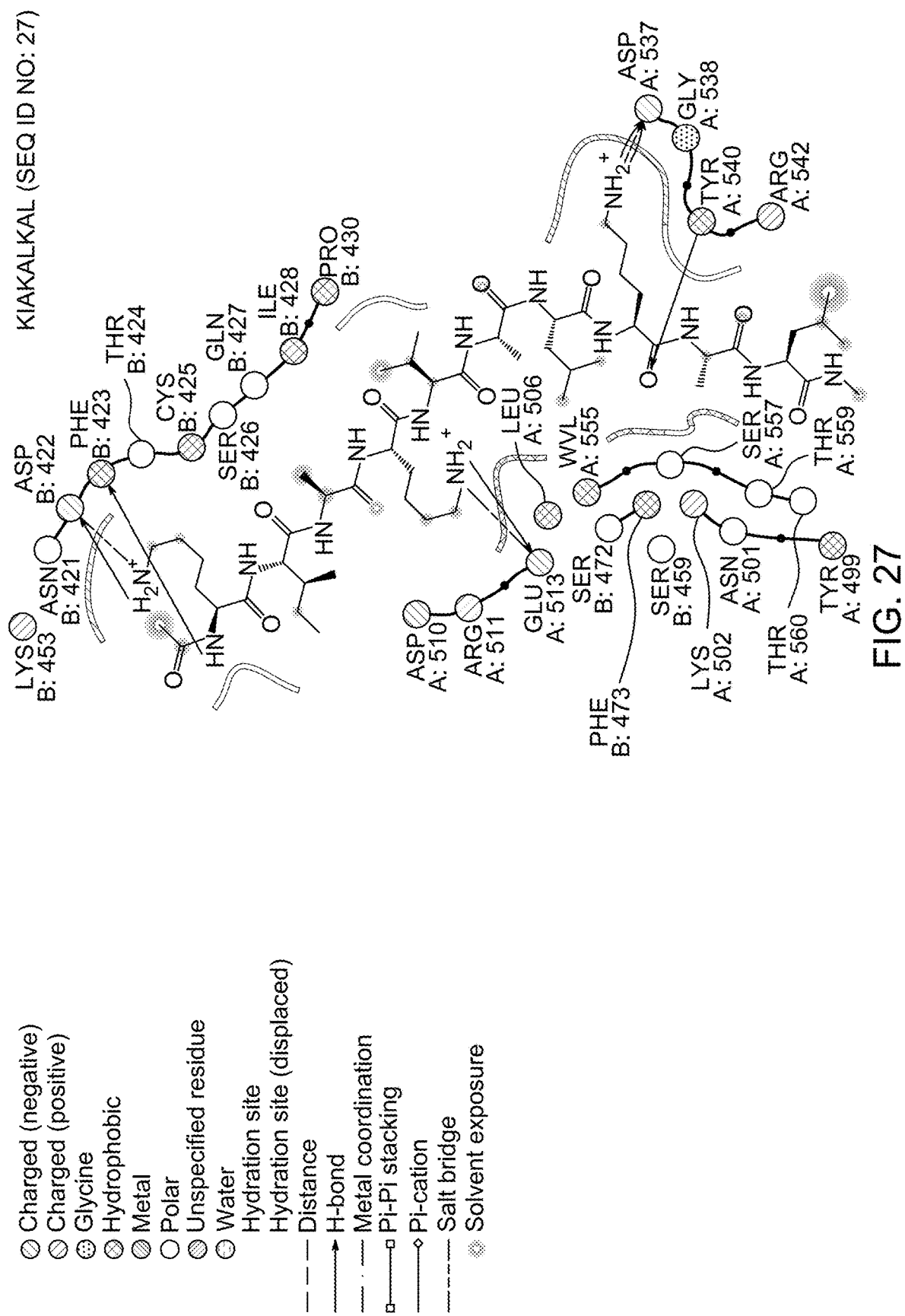
FIG. 27 shows the interactions of a peptide of SEQ ID NO: 27 with MERS-CoV receptor binding domain of spike protein of SEQ ID NO: 28. The peptide forms six hydrogen bonds to Asp-422, Phe-423, Glu-513, Asp-537, Tyr-540, and exhibits an aromatic hydrogen interaction. Asp-537 forms two hydrogen bonds interactions. Asp 422, Glu-513 and Asp 537, each form one salt bridge interaction.

The notation [ ] denotes the specific atoms of the peptide which interact with the RBD, e.g., The [OH] group of the RYPAVGYT (SEQ ID NO: 1) peptide interacts with residue Thr-424 of the RBD.
A more graphic depiction this and other interactions appears in FIGS. 1-27.

Example 4

MERS-CoV pseudovirus production and inhibition viral infection assay. The antibody virus neutralization assay described by Yu et al., Scientific Reports (2015/8/18) 5, 13133, was modified to examine the antiviral activity of the invention. The MERS-CoV pseudoviruses were generated in HEK293T cells by co-transfection of the human immunodeficiency virus backbone expressing firefly luciferase (pNL43R-E-luciferase) and the MERS-CoV spike glycoprotein expression vector (pcDNA3.1+, Invitrogen) into HEK293T cells.

The viral supernatant was harvested 48 hours after transfection and was then normalized using a p24 ELISA kit (Beijing Quantobio Biotechnology Co., LTD, China).

MERS-CoV pseudoviruses bearing wild-type spike glycoprotein were used to infect Huh7 target cells endogenously expressing hDPP4 in the presence of various concentration of the peptide of interest.

The infected Huh7 cells were lysed 48 hours after infection and viral entry efficiency was quantified by comparing the luciferase activities of the pseudoviruses in the presence and absence of the peptide of interest. IC50s were calculated using the dose-response inhibition model in GraphPad Prism (GraphPad Software Inc.).

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

In the event of any ambiguity in an accession number date, the latest version prior to the filing date of the present application should be used.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method for reducing the severity of an infection with Middle East respiratory syndrome-related coronavirus (MERS-CoV), comprising:
administering to a subject in need thereof a composition comprising at least one peptide selected from the group consisting of SEQ ID NOS: 1, 3, 4, 5, 7, and 10 in an amount effective to reduce the severity of infection with MERS-CoV, wherein said peptide binds to MERS-CoV spike (S) protein.

2. The method of claim 1, wherein the peptide consists of SEQ ID NO: 1, 3, 5, 7, or 10.

3. The method of claim 1, wherein the peptide forms hydrogen bonds with Thr-424, Gln-427, Phe-473, Glu-536, Asp-537, and Gln-471 of SEQ ID NO: 28.

4. The method of claim 1, wherein the peptide has a docking score for MERS-CoV S1 subunit of −9 or lower.

5. The method of claim 1, wherein the peptide comprises a chemically modified N-terminus or chemically modified C-terminus or at least one other covalent modification.

6. The method of claim 1, wherein the peptide is covalently bound to polyethylene glycol (PEG) or to a dendritic polymer or is covalently bound to at least one lipid or carbohydrate component.

7. The method of claim 1, wherein the composition further comprises a pharmaceutically acceptable excipient, carrier, or adjuvant.

8. The method of claim 1, wherein the composition comprises a particle having an average diameter ranging from 0.1 to 5 μm which particle contains the peptide.

9. The method of claim 1, wherein the composition comprises a particle having an average diameter of >5 to 10 μm which particle contains the peptide.

10. The method of claim 1, wherein the composition comprises a liposome that has an average diameter ranging from 0.1 to 5 μm which liposome contains the peptide.

11. The method of claim 1, wherein the composition comprises a powder comprising at least one solid excipient which has an average diameter ranging from 0.1 to 5 μm which powder contains the peptide.

12. The method of claim 1, wherein said administering comprises administering the composition via an inhaler or nebulizer to the subject.

13. The method of claim 1, wherein said administering comprises administering the composition orally, intranasally, intraocularly, or into the upper or lower respiratory system of the subject.

14. The method of claim 1, wherein said administering comprises administering the composition parenterally to the subject.

15. The method of claim 1, wherein the subject is a smoker, a vaper, has chronic obstructive pulmonary disease, bronchial asthma, allergy, cystic fibrosis, or influenza, rhinovirus, or another respiratory infection other than MERS-CoV.

16. The method of claim 1, wherein said composition comprises a dosage of said peptide ranging from 0.01, 0.02, 0.05, 0.1, 0.2, 0.5, 1, 2, 5, to 10 mg/kg of body weight of the subject.

17. The method of claim 1, wherein said reducing the severity of infection comprises inhibiting the replication of MERS-CoV.

18. The method of claim 1, wherein said reducing the severity of infection comprises inhibiting attachment or infectivity of MERS-CoV.

19. The method of claim 1, wherein said reducing the severity of infection comprises a delayed onset of clinical symptoms of the disease in a susceptible subject, a reduction in severity of some or all clinical symptoms of the disease, an improvement in the overall health or well-being of the subject; or a slower progression of disease or a reduction in transmission rate.

* * * * *